(12) United States Patent
Poon et al.

(10) Patent No.: US 11,993,626 B2
(45) Date of Patent: May 28, 2024

(54) FUNCTIONALIZED N-ACETYLGALACTOSAMINE ANALOGS

(71) Applicant: Hongene Biotech Corporation, Union City, CA (US)

(72) Inventors: Wing C. Poon, Union City, CA (US); Xiaoyang Guan, Union City, CA (US); David Yu, Union City, CA (US); Ruiming Zou, Union City, CA (US); Xiaojun Li, Union City, CA (US); Michael Su, Union City, CA (US); Gang Zhao, Union City, CA (US); Gengyu Du, Union City, CA (US); Yun-Chiao Yao, Union City, CA (US); Aldrich N. K. Lau, Palo Alto, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 18/065,503

(22) Filed: Dec. 13, 2022

(65) Prior Publication Data

US 2023/0279041 A1    Sep. 7, 2023

Related U.S. Application Data

(60) Provisional application No. 63/290,010, filed on Dec. 15, 2021.

(51) Int. Cl.
*C07H 15/26* (2006.01)
*C07H 21/00* (2006.01)

(52) U.S. Cl.
CPC .......... *C07H 15/26* (2013.01); *C07H 21/00* (2013.01)

(58) Field of Classification Search
None
See application file for complete search history.

(56) References Cited

U.S. PATENT DOCUMENTS

| | | |
|---|---|---|
| 7,037,936 B2 | 5/2006 | McKenna et al. |
| 8,962,580 B2 | 2/2015 | Manoharan et al. |
| 10,016,518 B2 | 7/2018 | Anthony et al. |
| 10,294,474 B2 | 5/2019 | Li et al. |
| 10,662,427 B2 | 5/2020 | Melquist et al. |
| 10,669,301 B2 | 6/2020 | Guzaev et al. |
| 10,781,175 B2 | 9/2020 | Guzaev et al. |
| 11,418,822 B2 | 8/2022 | Weil et al. |
| 11,649,260 B2 | 5/2023 | Guan et al. |
| 2012/0276108 A1 | 11/2012 | Priebe |
| 2016/0266133 A1 | 9/2016 | Levy |
| 2017/0022505 A1 | 1/2017 | Hadwiger et al. |
| 2018/0064819 A1 | 3/2018 | Li et al. |
| 2018/0195070 A1 | 7/2018 | Melquist et al. |
| 2019/0211368 A1 | 7/2019 | Butora et al. |
| 2019/0225644 A1 | 7/2019 | Butora et al. |
| 2019/0247468 A1 | 8/2019 | Mahdavi et al. |
| 2019/0256849 A1 | 8/2019 | Li et al. |
| 2020/0263179 A1 | 8/2020 | Melquist et al. |
| 2020/0270611 A1 | 8/2020 | Gryaznov et al. |
| 2021/0099739 A1 | 4/2021 | Weil et al. |
| 2023/0100220 A1 | 3/2023 | Poon |

FOREIGN PATENT DOCUMENTS

| | | |
|---|---|---|
| EP | 3 677 588 | 7/2020 |
| EP | 3 763 815 | 1/2021 |
| WO | WO 03/039523 | 5/2003 |
| WO | WO 15/066697 | 5/2015 |
| WO | WO 15/105083 | 7/2015 |
| WO | WO 15/168618 | 11/2015 |
| WO | WO 17/066789 | 4/2017 |
| WO | WO 17/177326 | 10/2017 |
| WO | WO 18/044350 | 3/2018 |
| WO | WO 18/067900 | 4/2018 |
| WO | WO 19/051257 | 3/2019 |
| WO | WO 19/053661 | 3/2019 |
| WO | WO 19/075419 | 4/2019 |
| WO | WO 19/211595 | 11/2019 |
| WO | WO 20/093061 | 5/2020 |
| WO | WO 20/093098 | 5/2020 |
| WO | WO 21/037205 | 3/2021 |
| WO | WO 22/055726 | 3/2022 |
| WO | WO 22/076922 | 4/2022 |

OTHER PUBLICATIONS

Carey, 1992, Organic Chemistry, 2d ed., McGraw-Hill, Inc., New York, pp. 328-331.
Craig et al., 2018, Recent preclinical and clinical advances in oligonucleotide conjugates. Expert Opin. Drug. Deliv. 15(6):629-640.
Debacker et al., 2020, Delivery of Oligonucleotides to the Liver with GalNAc: From Research to Registered Therapeutic Drug. Mol. Ther., 8:1759-1771.
Greene et al., 1999, Protective Groups in Organic Synthesis, 3rd Ed., John Wiley & Sons, New York (TOC).
Huang, 2017, Preclinical and Clinical Advances of GalNAc-Decorated Nucleic Acid Therapeutics. Mol. Ther. Nucleic. Acids., 6:116-132.
IUPAC-IUB Commission on Biochemical Nomenclatures, 1972, Abbreviated nomenclature of synthetic polypeptides (polymerized amino acids), revised recommendations (1971), Biochem. 11(5):942-944.

(Continued)

*Primary Examiner* — Layla D Berry
(74) *Attorney, Agent, or Firm* — Knobbe, Martens, Olson & Bear, LLP

(57) ABSTRACT

Embodiments of the present application relate to functionalized N-acetylgalactosamine-analogs, methods of making, and uses of the same. In particular, mono or trivalent N-acetylgalactosamine analogs may be prepared by utilizing a wide variety of linkers containing functional groups. These functionalized N-acetylgalactosamine-analogs may be used in the preparation of targeted delivery of oligonucleotide-based therapeutics.

31 Claims, No Drawings
Specification includes a Sequence Listing.

(56) References Cited

OTHER PUBLICATIONS

Li et al., 2012, Identification of a specific inhibitor of nOGA—a caspase-3 cleaved O-GlcNAcase variant during apoptosis, Biochemistry (Moscow), 77(2):194-200.
McMurry, 2000, Organic Chemistry, 5th ed., Brooks/Cole, Pacific Grove, CA, pp. 398 and 408.
McOmie, ed., 1973, Protective Groups in Organic Chemistry, Plenum Press (TOC).
Roberts et al., 2020, Advances in oligonucleotide drug delivery. Nat. Rev. Drug Discov. 10,:673-694.
Saneyoshi et al., 2017, Alkyne-linked reduction-activated protecting groups for diverse functionalization on the backbone of oligonucleotides, Bioorganic & Medicinal Chemistry, 25(13):3350-3356.
Scheit, 1980, Nucleotide analogs: Synthesis and biological function. New York: John Wiley & Sons (TOC).
Streitwieser et al., 1981, Introduction to Organic Chemistry, 2d ed., Macmillan Publishing Co., Inc., New York, pp. 169-171.
Uhlman et al., Jun. 1990, Antisense oligonucleotides: a new therapeutic principle, Chemical Reviews, 90(4):543-584.
Yamada et al., 2011, Versatile site-specific conjugation of small molecules to siRNA using click chemistry, J. Org. Chem., 76:1198-1211.
International search report and written opinion dated Apr. 17, 2023 in International Application No. PCT/US2022/081413.

```
SEQUENCE LISTING

Sequence total quantity: 1
SEQ ID NO: 1            moltype = DNA   length = 10
FEATURE                 Location/Qualifiers
source                  1..10
                        mol_type = other DNA
                        organism = synthetic construct
SEQUENCE: 1
tttttttttt                                                                10
```

FUNCTIONALIZED N-ACETYLGALACTOSAMINE ANALOGS

FIELD

The present application relates to functionalized N-acetylgalactosamine analogs and their methods of preparation. The functionalized N-acetylgalactosamine analogs disclosed herein may be used for targeted in vivo delivery of oligonucleotide-based therapeutics.

REFERENCE TO SEQUENCE LISTING

The present application is being filed along with a Sequence Listing in electronic format. The Sequence Listing is provided as a file entitled "HGENE.013A_Sequence_Listing.xml" created on Dec. 12, 2022, which is 1.90 KB in size. The information in the electronic format of the Sequence Listing is incorporated herein by reference in its entirety.

BACKGROUND

Description of the Related Art

Oligonucleotide-based drugs have become a powerful epitome having ability to treat various diseases. N-acetylgalactosamine (GalNAc) is a well-defined liver-targeted moiety benefiting from its high affinity with asialoglycoprotein receptor (ASGPR). It can facilitate uptake and clearance of circulating GalNAc-conjugated oligo via clathrin-mediated endocytosis. The strongest attribute of GalNAc conjugates, compared to other oligo conjugates, is the internalization and cellular trafficking efficiency, which enables near-complete mRNA knockdown at exceedingly low doses in preclinical species and human subjects. This differentiating factor is related to the high membrane density of the ASGPR on hepatocytes and the rapid cycle in which it internalizes and recycles back to the cell surface. Only 15 mins are required for ASGPR internalization and recycling to the cell surface.

ASGPR consists of two homologous subunits, designated H1 and H2 in the human system, which form a non-covalent heterooligomeric complex with estimated ratios of 2:1 and 5:1, respectively. Both subunits are single-spanning membrane proteins with a calcium-dependent Gal/GalNAc recognition domain (CRDs). On the native receptor on the hepatocyte surface these binding sites are 25-30 Å apart. All conjugations of mono-, di-, tri-, or tetra-GalNAc sugars can enhance the delivery efficiency of oligonucleotides to hepatocytes. Binding hierarchy of polyvalent ligands is: tetraantennary>triantennary>>diantennary>>monoantennary. Since the fourth GalNAc moiety present in the tetraantennary ligand does not markedly enhance the affinity, it was presumed that the binding requirements of the cell-surface receptor are largely saturated by the triantennary structure. Scientists have reached a consensus that triantennary GalNAc analogs with a mutual distance of 20 Å exhibit the highest affinity with ASGPR.

Trivalent and monovalent GalNAc analogs have been previously reported. Oligonucleotide therapeutics have pharmacological challenges including susceptibility to nuclease-mediated degradation, rapid elimination, poor biodistribution, insufficient membrane permeability, immune stimulation, and potentially significant off-target effects.

Accordingly, a need exists for preparing novel functionalized GalNAc analogs to improve drug delivery.

SUMMARY

Some aspect of the present disclosure relates to compounds of Formula (I):

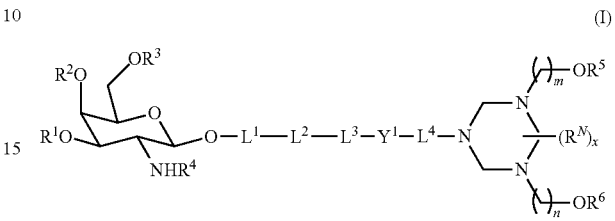

or a pharmaceutically acceptable salt thereof; wherein
each of $R^1$, $R^2$, and $R^3$ is independently hydrogen, benzyl, or —C(=O)$R^8$;
$R^4$ is —C(=O)$C_{1-6}$ alkyl or —C(=O)$C_{1-6}$ haloalkyl;
$R^5$ is a hydroxy protecting group;
$R^6$ is hydrogen, a phosphoramidite moiety, —C(=O)CH$_2$CH$_2$C(=O)$R^{6A}$, or —P(O$R^{6B}$)N$R^{6C}R^{6D}$;
$Y^1$ is N$R^7$, N$R^7$C(=O), O, C(=O)O, or a bond;
each of $L^1$, $L^2$, and $L^3$ is independently a bond, —C(=O)—, —C(=S)—, —S(=O)$_2$—, —C(=O)N$R^9$—, —C(=S)N$R^9$—, —C(=O)O—, —C(=S)O—, —N$R^9$C(=O)N$R^9$—, —N$R^9$C(=S)N$R^9$—, —OP(=O)(OH)O—, —OP(=S)(OH)O—, —O—, —S—, —N$R^9$—, optionally substituted $C_{1-10}$ alkylene, optionally substituted $C_{6-10}$ arylene, optionally substituted $C_{3-10}$ cycloalkylene, optionally substituted 5-10 membered hetetroarylene, optionally substituted 5 to 10 membered heterocyclylene, or optionally substituted 2 to 15 membered heteroalkylene wherein one or more carbon atoms are replaced with C(=O), O, S or N, provided that at least one of $L^1$, $L^2$, and $L^3$ is not a bond;
$L^4$ is a bond or an optionally substituted $C_{1-8}$ alkylene;
each of $R^7$ and $R^9$ is independently hydrogen, unsubstituted $C_{1-6}$ alkyl, or substituted $C_{1-6}$ alkyl;
each $R^8$ is independently $C_{1-6}$ alkyl, $C_{1-6}$ haloalkyl, or optionally substituted phenyl;
$R^{6A}$ is —OH, —O$R^{10}$ or —N$R^{11}R^{12}$.
each of $R^{6B}$, $R^{6C}$ and $R^{6D}$ is independently H, $C_{1-6}$ haloalkyl, or unsubstituted or substituted $C_{1-6}$ alkyl;
$R^{10}$ is unsubstituted or substituted $C_{1-6}$ alkyl, or a hydroxy protecting group;
each of $R^{11}$ and $R^{12}$ is independently H, unsubstituted or substituted $C_{1-6}$ alkyl, or an amino protecting group; and
each of m and n is independently 1, 2, 3, 4, 5 or 6
x is 0, 1, 2, 3, 4, 5 or 6; and
each $R^N$ is independently halo, cyano, hydroxy, amino, unsubstituted $C_{1-6}$ alkyl, substituted $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl, or two adjacent $R^N$ attached to the same carbon atom form oxo (=O).
In some embodiments of the compound described herein, compounds of Formula (I) may have the structure of Formula (Ia):

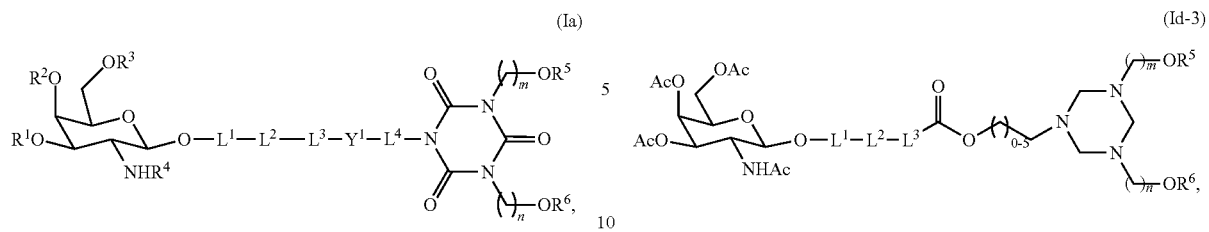

(Ia)

or a pharmaceutically acceptable salt thereof.

In some further embodiments, compounds of Formula (I) may have the structure of Formula (Ib):

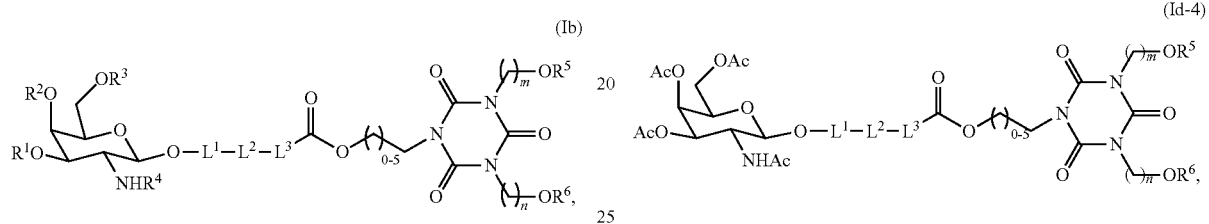

(Ib)

or a pharmaceutically acceptable salt thereof.

In some further embodiments, compounds of Formula (I) may have the structure of Formula (Ic):

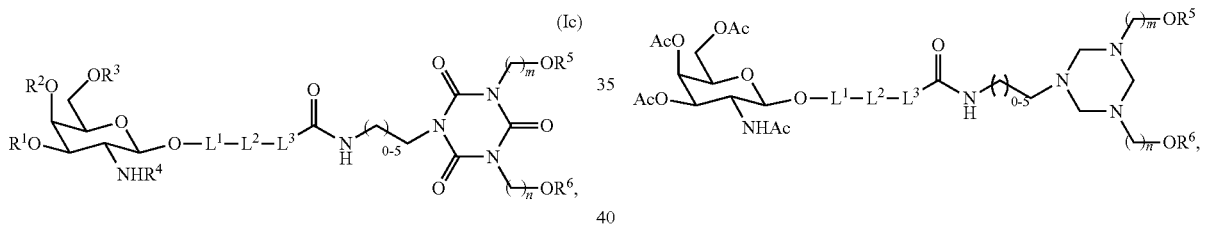

(Ic)

or a pharmaceutically acceptable salt thereof.

In some embodiments, compounds of Formula (I) may have the structure selected from the group consisting of:

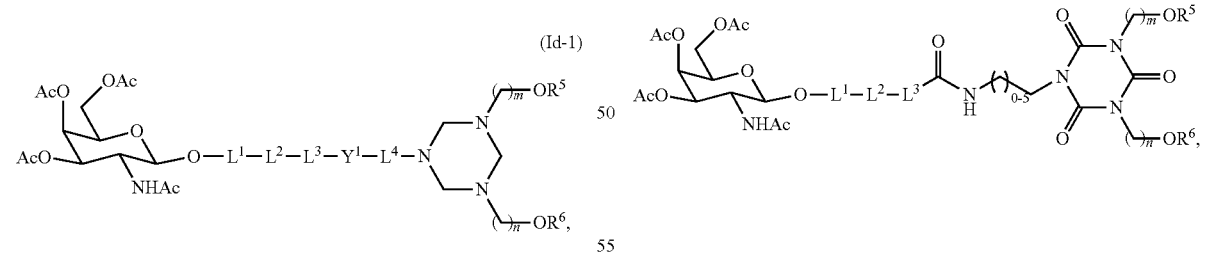

-continued (Id-8)

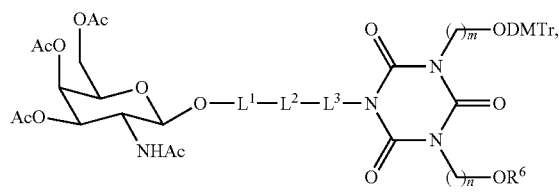

and pharmaceutically acceptable salts thereof, wherein Ac is —C(O)CH$_3$, each of m and n is independently 1 or 2; and R$^6$ is —C(=O)CH$_2$CH$_2$C(=O)OH or

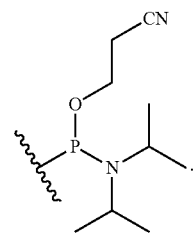 [SMILES: *P(OCCC#N)N(C(C)C)C(C)C]

In some further embodiments, each of L$^1$, L$^2$ and L$^3$ is independently a bond, C$_{1-10}$ alkylene, 3 to 15 membered heteroalkylene where one or more carbon atoms are replaced with C(=O), O or N, or a PEG linker comprising one to five —OCH$_2$CH$_2$— repeating units.

Some aspect of the present disclosure relates to compounds of Formula (II):

each of X$^1$, X$^2$ and X$^3$ is independently —O(CH$_2$)$_{1-3}$—, —NH(CH$_2$)$_{1-3}$—, —C(=O)(CH$_2$)$_{1-3}$— or —NHC(=O)(CH$_2$)$_{1-3}$—;

each of L$^{1a}$, L$^{1b}$, L$^{1c}$, L$^{2a}$, L$^{2b}$, L$^{2c}$, L$^{3a}$, L$^{3b}$, and L$^{3c}$ is independently a bond, —C(=O)—, —C(=S)—, —S(=O)$_2$—, —C(=O)NR$^9$—, —C(=S)NR$^9$—, —C(=O)O—, —C(=S)O—, —NR$^9$C(=O)NR$^9$—, —NR$^9$C(=S)NR$^9$—, —OP(=O)(OH)O—, —OP(=S)(OH)O—, —O—, —S—, —NR$^9$—, optionally substituted C$_{1-10}$ alkylene, optionally substituted C$_{6-10}$ arylene, optionally substituted C$_{3-10}$ cycloalkylene, optionally substituted 5-10 membered hetetroarylene, optionally substituted 5 to 10 membered heterocyclylene, or optionally substituted 2 to 15 membered heteroalkylene wherein one or more carbon atoms are replaced with C(=O), O, S or N, provided that at least one of L$^{1a}$, L$^{1b}$ and L$^{1c}$ is not a bond, at least one of L$^{2a}$, L$^{2b}$ and L$^{2c}$ is not a bond, and at least one of L$^{3a}$, L$^{3b}$ and L$^{3c}$ is not a bond;

L$^4$ is a bond, optionally substituted C$_{1-8}$ alkylene or —(CH$_2$)$_{1-3}$(OCH$_2$CH$_2$)$_{1-5}$OCH$_2$—;

L$^5$ is a bond, optionally substituted C$_{1-10}$ alkylene, or optionally substituted 2 to 15 membered heteroalkylene wherein one or more carbon atoms are replaced with C(=O), O, S or N;

each of R$^7$ and R$^9$ is independently hydrogen, unsubstituted C$_{1-6}$ alkyl, or substituted C$_{1-6}$ alkyl;

each R$^8$ is independently C$_{1-6}$ alkyl, C$_{1-6}$ haloalkyl, or optionally substituted phenyl;

R$^{6A}$ is —OH, —OR$^{10}$ or —NR$^{11}$R$^{12}$.

each of R$^{6B}$, R$^{6C}$ and R$^{6D}$ is independently H, C$_{1-6}$ haloalkyl, or unsubstituted or substituted C$_{1-6}$ alkyl;

(II)

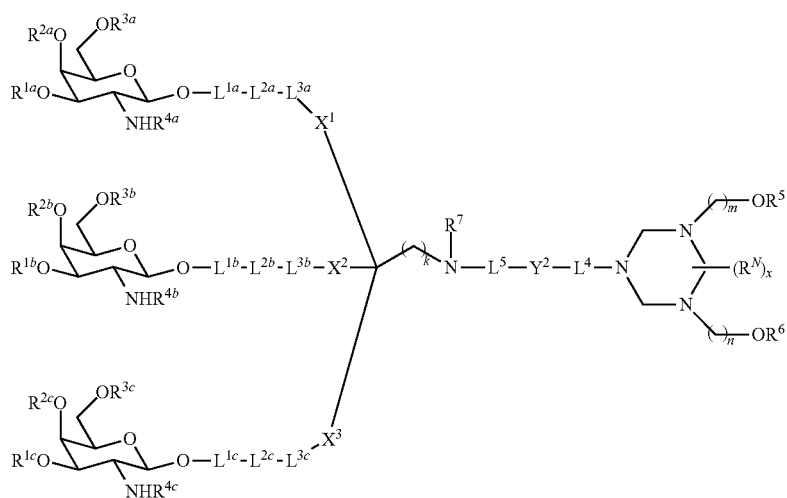

or a pharmaceutically acceptable salt thereof, wherein each of R$^{1a}$, R$^{1b}$, R$^{1c}$, R$^{2a}$, R$^{2b}$, R$^{2c}$, R$^{3a}$, R$^{3b}$, and R$^{3c}$ is independently hydrogen, benzyl, or —C(=O)R$^8$;

each of R$^{4a}$, R$^{4b}$ and R$^{4c}$ is independently —C(=O)C$_{1-6}$ alkyl or —C(=O)C$_{1-6}$ haloalkyl;

R$^5$ is a hydroxy protecting group;

R$^6$ is hydrogen, a phosphoramidite moiety, —C(=O)CH$_2$CH$_2$C(=O)R$^{6A}$, or —P(OR$^{6B}$)NR$^{6C}$R$^{6D}$;

Y$^2$ is a bond, NR$^7$, NR$^7$C(=O), C(=O)O, or O;

R$^{10}$ is unsubstituted or substituted C$_{1-6}$ alkyl, or a hydroxy protecting group;

each of R$^{11}$ and R$^{12}$ is independently H, unsubstituted or substituted C$_{1-6}$ alkyl, or an amino protecting group;

each of m and n is independently 1, 2, 3, 4, 5 or 6;

k is 0 or 1;

x is 0, 1, 2, 3, 4, 5 or 6; and each R$^N$ is independently halo, cyano, hydroxy, amino, unsubstituted C$_{1-6}$ alkyl, substituted C$_1$-C$_6$ alkyl, C$_1$-C$_6$ haloalkyl, hydroxy(C$_1$-C$_6$ alkyl), amino(C$_1$-C$_6$ alkyl), (C$_1$-C$_6$ alkyl)amino, C$_1$-C$_6$ alkoxy, C$_1$-C$_6$ haloalkoxy, ($C_1$-$C_6$ alkoxy)$C_1$-$C_6$ alkyl, or —O($C_1$-$C_6$ alkoxy)$C_1$-$C_6$ alkyl, or two adjacent $R^N$ attached to the same carbon atom form oxo (=O).

In some embodiments, compounds of Formula (II) may have the structure of Formula (IIa):

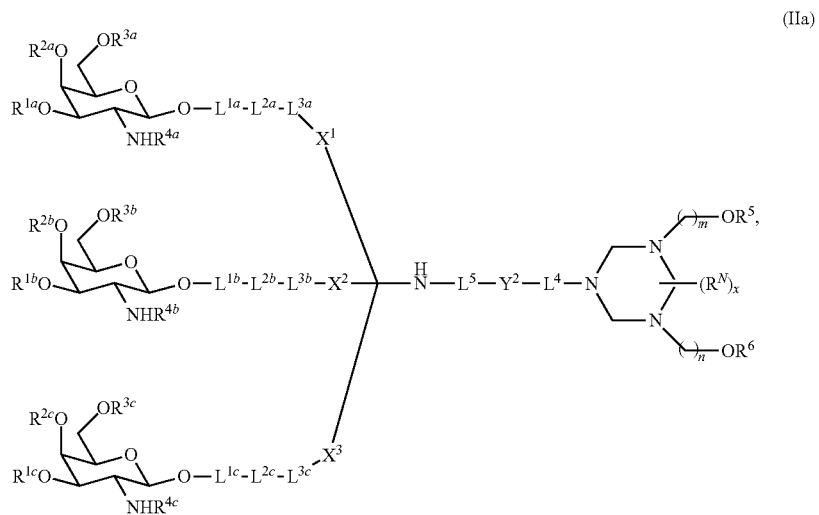

(IIa)

or a pharmaceutically acceptable salt thereof.

In some embodiments, compounds of Formula (II) may have the structure of Formula (IIb):

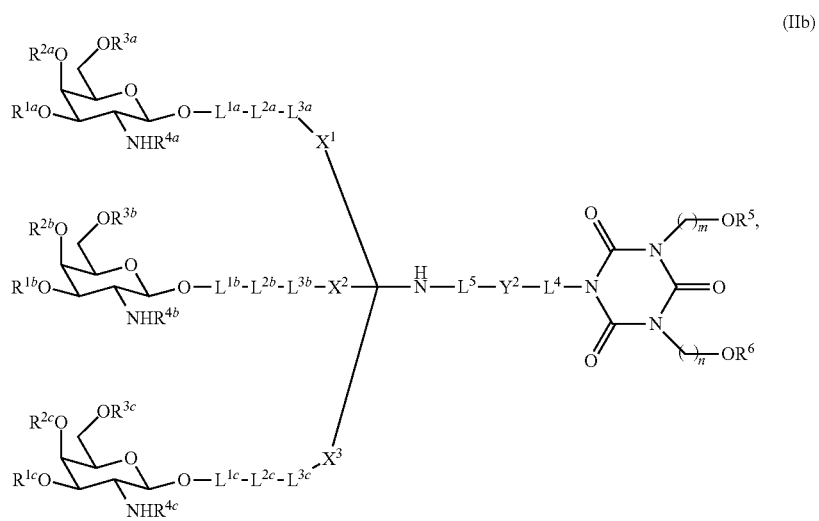

(IIb)

or a pharmaceutically acceptable salt thereof.

In some embodiments, compounds of Formula (II) may have the structure of Formula (IIc):
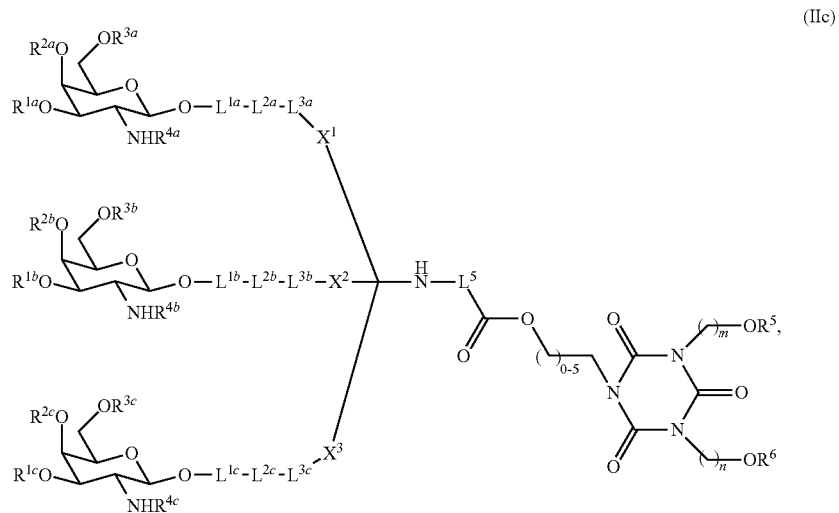
(IIc)
or a pharmaceutically acceptable salt thereof.
In some embodiments, compounds of Formula (II) may have the structure of Formula (IId):
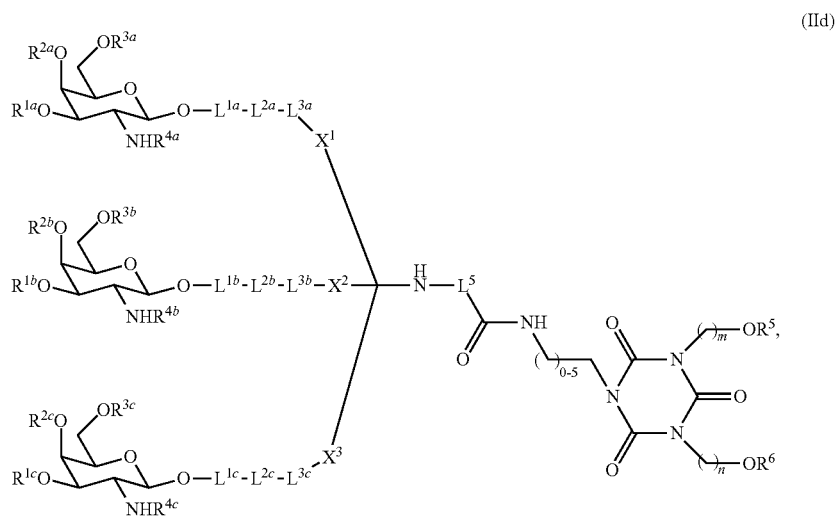
(IId)
or a pharmaceutically acceptable salt thereof.

In some embodiments, compounds of Formula (I) may have the structure selected from the group consisting of:
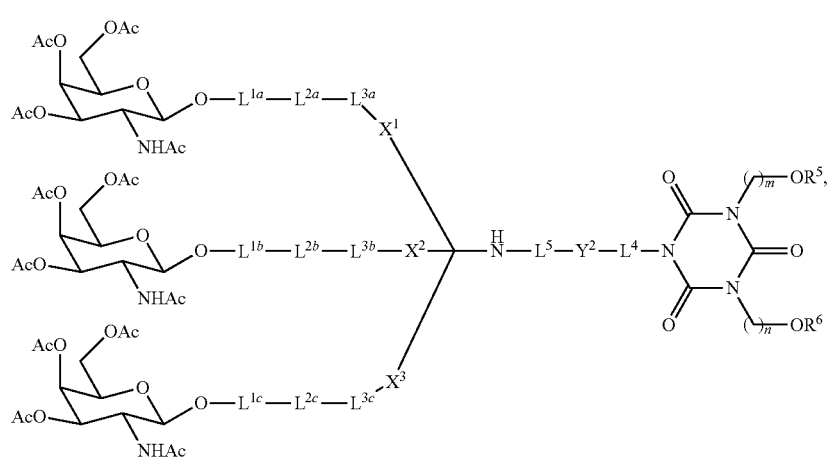
(IIe-1)
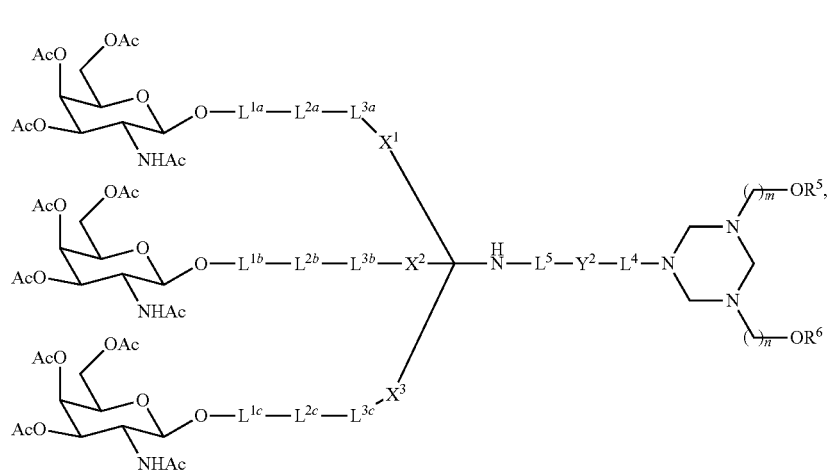
(IIe-2)
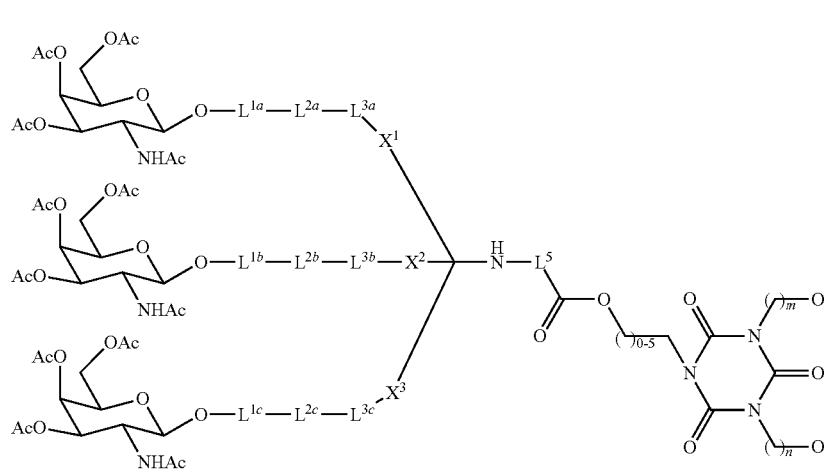
(IIe-3)

-continued
(IIe-4)
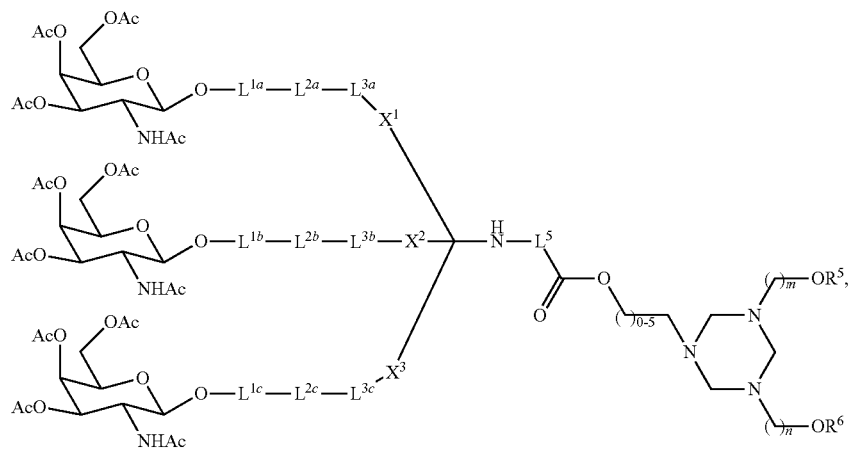
(IIe-5)
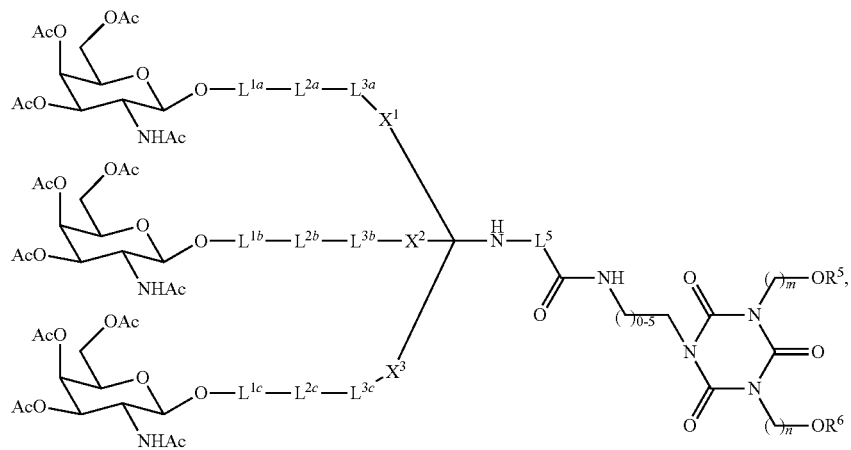
(IIe-6)
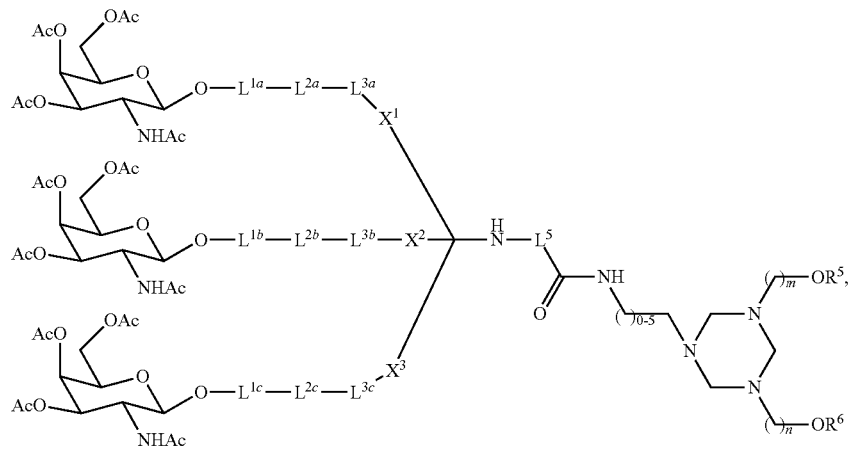

-continued

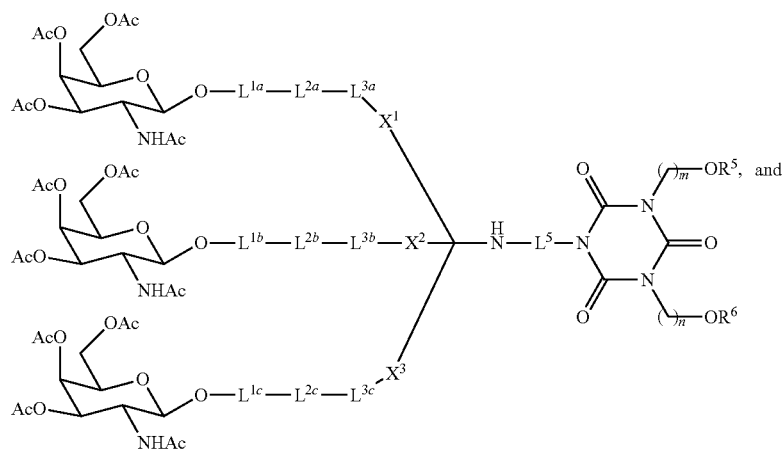

(IIe-7)

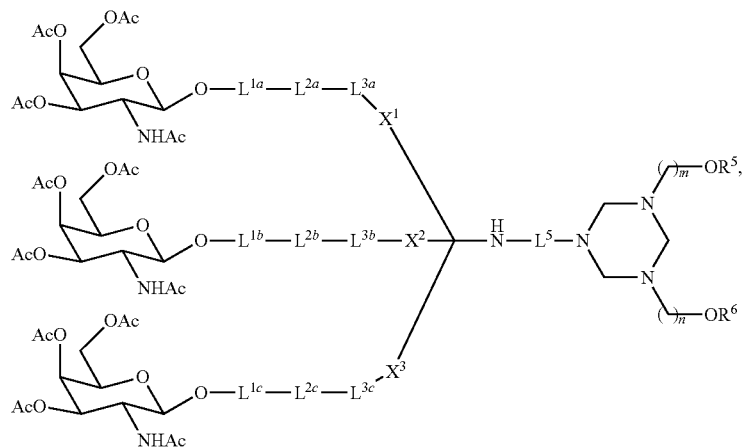

(IIe-8)

and pharmaceutically acceptable salts thereof, wherein
each of $X^1$, $X^2$ and $X^3$ is —OCH$_2$—, —NHCH$_2$—, —C(=O)CH$_2$CH$_2$—, —C(=O)CH$_2$—, —NHC(=O)CH$_2$CH$_2$— or —NHC(=O)CH$_2$—, or each of $X^1$ and $X^3$ is —C(=O)CH$_2$CH$_2$—, and $X^2$ is —C(=O)CH$_2$—, or each of $X^1$ and $X^3$ is —NHC(=O)CH$_2$CH$_2$—, and $X^2$ is —NHC(=O)CH$_2$—;
Ac is —C(O)CH$_3$;
each of m and n is independently 1 or 2;
$R^5$ is DMTr; and
$R^6$ is —C(=O)CH$_2$CH$_2$C(=O)OH or

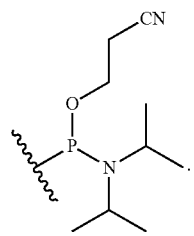 [SMILES: *P(OCCC#N)N(C(C)C)C(C)C]

Additional aspects of the present disclosure relate to a method of preparing a synthetic oligonucleotide, comprising reacting a compound described herein of Formula (I), (Ia), (Ib), (Ic), (Id-1), (Id-2), (Id-3), (Id-4), (Id-5), (Id-6), (Id-7), (Id-8), (II), (IIa), (IIb), (IIc), (IId), (IIe-1), (IIe-2), (IIe-3), (IIe-4), (IIe-5), (IIe-6), (IIe-7) or (IIe-8) with an oligonucleotide. In some embodiments, the oligonucleotide may have a 1 to 100 nucleobase length. In some embodiments, the reaction may be conducted on a solid support. Additional aspect of the present disclosure relates to synthetic oligonucleotide prepared by the method described herein.

DETAILED DESCRIPTION

The compounds disclosed herein relate to novel functionalized GalNAc analogs to provide novel methods for oligonucleotide delivery. In some embodiments, the functionalized GalNAc analogs disclosed herein may contain a phosphoramidite moiety that allows for the incorporation of the GalNAc analogs to the 5' end or any internal position of an oligonucleotide. In some other embodiments, the functionalized GalNAc analogs disclosed herein may contain a succinate moiety that allows for the incorporation of the GalNAc analogs on a solid support, which can introduce GalNAc analogs described herein to the 3' end of oligonucleotide.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^a$ and $R^b$, and the atom to which it is attached, are indicated to be "taken together" or "joined together" it means that they are covalently bonded to one another to form a ring:

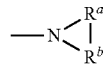

Whenever a group is described as being "optionally substituted" that group may be unsubstituted or substituted with one or more of the indicated substituents. Likewise, when a group is described as being "substituted", the substituent may be selected from one or more of the indicated substituents. If no substituents are indicated, it is meant that the indicated "optionally substituted" or "substituted" group may be one or more group(s) individually and independently selected from alkyl (e.g., $C_1$-$C_6$ alkyl); alkenyl (e.g., $C_2$-$C_6$ alkenyl); alkynyl (e.g., $C_2$-$C_6$ alkynyl); $C_3$-$C_8$ carbocyclyl (for example, $C_3$-$C_8$ cycloalkyl, $C_3$-$C_8$ cycloalkenyl, or $C_3$-$C_8$ cyclalkynyl, each may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); ($C_3$-$C_7$ carbocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heterocyclyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heterocyclyl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); aryl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (aryl)$C_1$-$C_6$ alkyl (may further be optionally substituted, for example, with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); 5-10 membered heteroaryl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); (5-10 membered heteroaryl)$C_1$-$C_6$ alkyl (may further be optionally substituted with halo, $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl); halo (e.g., fluoro, chloro, bromo, iodo); cyano; hydroxy; protected hydroxy; alkoxy (e.g., $C_1$-$C_6$ alkoxy); haloalkyl (e.g., $C_1$-$C_6$ haloalkyl, such as —$CF_3$); haloalkyl (e.g., $C_1$-$C_6$ haloalkoxy such as —$OCF_3$); ($C_1$-$C_6$ alkoxy)$C_1$-$C_6$ alkyl; —O($C_1$-$C_6$ alkoxy)$C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy; sulfhydryl (mercapto); alkylthio (e.g., $C_1$-$C_6$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (for example, NH($C_1$-$C_6$ alkyl); di-substituted amino (for example, N($C_1$-$C_6$ alkyl)$_2$); oxo (=O); and thioxo (=S).

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl, aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 20 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 20 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro [3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene (—$CH_2CH_2$—), propylene (—$CH_2CH_2CH_2$—), butylene (—$CH_2CH_2CH_2CH_2$—), and pentylene (—$CH_2CH_2CH_2CH_2CH_2$—).

As used herein, "alkenylene" refers to a straight or branched chain di-radical chemical group containing only carbon and hydrogen and containing at least one carbon-carbon double bond that is attached to the rest of the molecule via two points of attachment. The alkenylene group may be designated as "$C_2$-$C_{10}$ alkenylene" or similar designations. By way of example only, "$C_2$-$C_{10}$ alkenylene" indicates that there are two to ten carbon atoms in the alkenylene chain.

As used herein, "alkynylene" refers to a straight or branched chain di-radical chemical group containing only carbon and hydrogen and containing at least one carbon-carbon triple bond that is attached to the rest of the molecule via two points of attachment. The alkynylene group may be designated as "$C_2$-$C_{10}$ alkenylene" or similar designations. By way of example only, "$C_2$-$C_{10}$ alkynylene" indicates that there are two to ten carbon atoms in the alkynylene chain.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom (N), oxygen atom (S) or sulfur atom (S)). For example, a —$CH_2$— may be replaced with —O—, —S—, or —NH—. Heteroalkylene groups include, but are not limited to ether, thioether, amino-alkylene, and alkylene-amino-alkylene moieties. In some embodiments, the heteroalkylene may include one, two, three, four, or five —$CH_2CH_2O$— unit(s). Alternatively and/or additionally, one or more carbon atoms can also be substituted with an oxo (=O) to become a carbonyl. For example, a —$CH_2$— may be replaced with —C(=O)—. It is understood that when a carbon atom is replaced with a carbonyl group, it refers to the replacement of —$CH_2$— with —C(=O)—. When a carbon atom is replaced with a nitrogen atom, it refers to the replacement of —CH— with —N—. When a carbon atom is replaced with an oxygen or sulfur atom, it refers to the replacement of —$CH_2$— with —O— or —S—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylallyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl group, as defined herein. A non-limiting list of alkoxy group includes methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —$NH_2$ group. The term "mono-substituted amino group" as used herein refers to an amino (—$NH_2$) group where one of the hydrogen atom is replaced by a substituent. The term "di-substituted amino group" as used herein refers to an amino (—$NH_2$) group where each of the two hydrogen atoms is replaced by a substituent. The term "optionally substituted amino," as used herein refer to a —$NR_AR_B$ group where $R_A$ and $R_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a —$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups.

As used herein, "aminoalkyl" or "(amino)alkyl" refers to an alkyl group in which one or more of the hydrogen atoms are replaced by an amino group or "—$NR_AR_B$" group as defined herein. The alkyl portion of the aminoalkyl, includes, for example, $C_1$-$C_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy) alkyl" refers to an alkoxy group connected via an —O-(alkylene) group, such as —O—($C_1$-$C_6$ alkoxy)$C_1$-$C_6$ alkyl, for example, —O—$(CH_2)_{1-3}$—$OCH_3$.

As used herein, "aryloxy" and "arylthio" refers to RO— and RS—, in which R is an aryl, as defined above, such as but not limited to phenyl. Both an aryloxy and arylthio may be substituted or unsubstituted.

A "sulfenyl" group refers to an "—SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(═O)O—" group in which R can be hydrogen, alkyl, alkenyl, alkynyl, carbocyclyl, aryl, heteroaryl, heterocyclyl, aralkyl, or heterocyclyl (alkyl), as defined herein. An O-carboxy may be substituted or unsubstituted.

The terms "ester" and "C-carboxy" refer to a "—C(═O) OR" group in which R can be the same as defined with respect to O-carboxy. An ester or C-carboxy may be substituted or unsubstituted.

A "trihalomethanesulfonyl" group refers to an "$X_3CSO_2$—" group wherein X is a halogen.

A "trihalomethanesulfonamido" group refers to an "$X_3CS(O)_2N(R)$—" group wherein X is a halogen and R is hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—$SO_2N(R_AR_B)$" group in which $R_A$ and $R_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(═O)N ($R_AR_B$)" group in which $R_A$ and $R_B$ can be the same as defined with respect to S-sulfonamido. An O-carbamyl may be substituted or unsubstituted.

An "N-carbamyl" group refers to an "ROC(═O)N ($R_A$)—" group in which R and $R_A$ can be the same as defined with respect to N-sulfonamido. An N-carbamyl may be substituted or unsubstituted.

An "O-thiocarbamyl" group refers to a "—OC(═S)—N ($R_AR_B$)" group in which $R_A$ and $R_B$ can be the same as defined with respect to S-sulfonamido. An O-thiocarbamyl may be substituted or unsubstituted.

An "N-thiocarbamyl" group refers to an "ROC(═S)N ($R_A$)—" group in which R and $R_A$ can be the same as defined with respect to N-sulfonamido. An N-thiocarbamyl may be substituted or unsubstituted.

A "C-amido" group refers to a "—C(═O)N($R_AR_B$)" group in which $R_A$ and $R_B$ can be the same as defined with respect to S-sulfonamido. A C-amido may be substituted or unsubstituted.

An "N-amido" group refers to a "RC(═O)N($R_A$)—" group in which R and $R_A$ can be the same as defined with respect to N-sulfonamido. An N-amido may be substituted or unsubstituted.

Where the numbers of substituents is not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

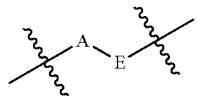

includes the substituent being oriented such that the A is attached at the leftmost attachment point of the molecule as well as the case in which A is attached at the rightmost attachment point of the molecule. In addition, if a group or substituent is depicted as

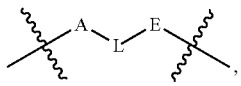

and when L is defined as a bond or absent; such group or substituent is equivalent to

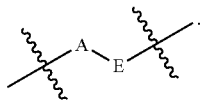

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(═O)CH$_3$ or Ac), or isobutyryl (iBu); arylalkylcarbonyls (e.g., benzyloxycarbonyl or benzoyl (i.e., —C(═O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3- dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

Examples of hydroxy protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl) xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of protecting groups commonly used to protect phosphate and phosphorus hydroxy groups include without limitation, methyl, ethyl, benzyl (Bn), phenyl, isopropyl, tert-butyl, allyl, cyclohexyl (cHex), pivaloyloxymethyl (—CH$_2$—O—C(=O)C(CH$_3$)$_3$, or POM), 4-methoxybenzyl, 4-chlorobenzyl, 4-nitrobenzyl, 4-acyloxybenzyl, 2-methylphenyl, 2,6-dimethylphenyl, 2-chlorophenyl, diphenylmethyl, 4-methylthio-1-butyl, 2-(S-Acetylthio) ethyl (SATE), 2-cyanoethyl, 2-cyano-1,1-dimethylethyl (CDM), 4-cyano-2-butenyl, 2-(trimethylsilyl)ethyl (TSE), 2-(phenylthio)ethyl, 2-(triphenylsilyl)ethyl, 2-(benzylsulfonyl)ethyl, 2,2,2-trichloroethyl, 2,2,2-tribromoethyl, 2,3-dibromopropyl, 2,2,2-trifluoroethyl, thiophenyl, 2-chloro-4-tritylphenyl, 2-bromophenyl, 2-[N-isopropyl-N-(4-methoxybenzoyl)amino]ethyl, 4-(N-trifluoroacetylamino) butyl, 4-oxopentyl, 4-tritylaminophenyl, 4-benzylaminophenyl and morpholino. Wherein more commonly used phosphate and phosphorus protecting groups include without limitation, methyl, ethyl, benzyl (Bn), phenyl, isopropyl, tert-butyl, 4-methoxybenzyl, 4-chlorobenzyl, 2-chlorophenyl, 2-cyanoethyl and POM.

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the compounds described herein may be in the form of a trifluoroacetate salt.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

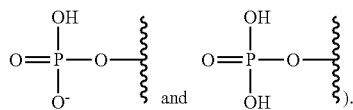

As used herein, the terms "monophosphate," "diphosphate," and "triphosphate" are used in their ordinary sense as understood by those skilled in the art, and include protonated forms.

Monovalent GalNAc Analogs of Formula (I)

Some embodiments of the present disclosure provide a compound of Formula (I), or a pharmaceutically acceptable salt thereof as described herein:

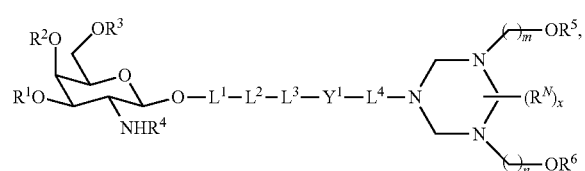

wherein each of $R^1$, $R^2$, and $R^3$ is independently hydrogen, benzyl, or —C(=O)$R^8$;
$R^4$ is —C(=O)$C_{1-6}$ alkyl or —C(=O)$C_{1-6}$ haloalkyl;
$R^5$ is a hydroxy protecting group;
$R^6$ is hydrogen, a phosphoramidite moiety, —C(=O)CH$_2$CH$_2$C(=O)$R^{6A}$, or —P(O$R^{6B}$)N$R^{6C}R^{6D}$;
$Y^1$ is N$R^7$, N$R^7$C(=O), O, C(=O)O, or a bond;
each of $L^1$, $L^2$, and $L^3$ is independently a bond, —C(=O)—, —C(=S)—, —S(=O)$_2$—, —C(=O)N$R^9$—, —C(=S)N$R^9$—, —C(=O)O—, —C(=S)O—, —N$R^9$C(=O)N$R^9$—, —N$R^9$C(=S)N$R^9$—, —OP(=O)(OH)O—, —OP(=S)(OH)O—, —O—, —S—, —N$R^9$—, optionally substituted $C_{1-10}$ alkylene, optionally substituted $C_{6-10}$ arylene, optionally substituted $C_{3-10}$ cycloalkylene, optionally substituted 5-10 membered hetetroarylene, optionally substituted 5 to 10 membered heterocyclylene, or optionally substituted 2 to 15 membered heteroalkylene wherein one or more carbon atoms are replaced with C(=O), O, S or N, provided that at least one of $L^1$, $L^2$, and $L^3$ is not a bond;
$L^4$ is a bond or an optionally substituted $C_{1-8}$ alkylene;
each of $R^7$ and $R^9$ is independently hydrogen, unsubstituted $C_{1-6}$ alkyl, or substituted $C_{1-6}$ alkyl;
each $R^8$ is independently $C_{1-6}$ alkyl, $C_{1-6}$ haloalkyl, or optionally substituted phenyl;
$R^{6A}$ is —OH, —O$R^{10}$ or —N$R^{11}R^{12}$.
each of $R^{6B}$, $R^{6C}$ and $R^{6D}$ is independently H, $C_{1-6}$ haloalkyl, or unsubstituted or substituted $C_{1-6}$ alkyl;
$R^{10}$ is unsubstituted or substituted $C_{1-6}$ alkyl, or a hydroxy protecting group;
each of $R^{11}$ and $R^{12}$ is independently H, unsubstituted or substituted $C_{1-6}$ alkyl, or an amino protecting group; and
each of m and n is independently 1, 2, 3, 4, 5 or 6;
x is 0, 1, 2, 3, 4, 5 or 6; and
each $R^N$ is independently halo, cyano, hydroxy, amino, unsubstituted $C_{1-6}$ alkyl, substituted $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl, or two adjacent $R^N$ attached to the same carbon atom form oxo (=O).

In some embodiments of the compounds of Formula (I), x is 0. In some embodiments, x is 1. In some embodiments, x is 2. In such embodiments, two adjacent $R^N$ attached to the same carbon atom form oxo (=O). In some embodiments, x is 3. In some embodiments, x is 4. In such embodiments, a first pair of two adjacent $R^N$ attached to a first carbon atom forms a first oxo (=O) group and a second pair of two adjacent $R^N$ attached to a second carbon atom forms a second oxo (=O) group. In some embodiments, x is 5. In some embodiments, x is 6. In such embodiments, a first pair of two adjacent $R^N$ attached to a first carbon atom forms a first oxo (=O) group, a second pair of two adjacent $R^N$ attached to a second carbon atom forms a second oxo (=O) group, and a third pair of two adjacent $R^N$ attached to a third carbon atom forms a third oxo (=O) group.

In some embodiments of the compounds of Formula (I), and the compound is also represented by Formula (Ia):

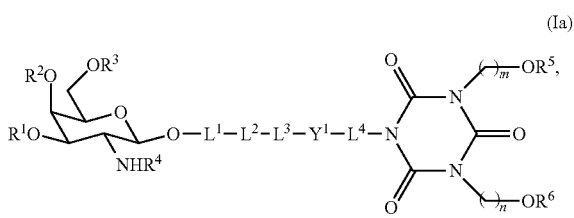

or a pharmaceutically acceptable salt thereof.

In some embodiments of the compounds of Formula (I) or (Ia), $Y^1$ is $NR^7$. In some embodiments, $Y^1$ is $NR^7C(=O)$. In such embodiments, $R^7$ is H. In other such embodiments, $R^7$ is $C_{1-4}$ alkyl, such as methyl, ethyl, n-propyl, isopropyl, n-butyl, or t-butyl. In some embodiments, $Y^1$ is O. In some embodiments, $Y^1$ is $C(=O)O$. In some embodiments, $Y^1$ is a bond.

In some embodiments of Formula (I) or (Ia), $L^4$ is $C_{1-6}$ alkylene. In such embodiments, $L^4$ is —$CH_2$—, —$(CH_2)_2$—, —$(CH_2)_3$—, —$(CH_2)_4$—, —$(CH_2)_5$— or —$(CH_2)_6$—. In some other embodiments, $L^4$ is a bond.

In some embodiments of the compounds of Formula (I) or (Ia), $Y^1$ is $C(=O)O$, $L^4$ is $C_{1-6}$ alkylene, and the compound is also represented by Formula (Ib):

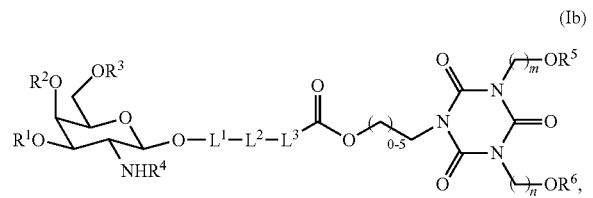

(Ib)

or a pharmaceutically acceptable salt thereof.

In some embodiments of the compounds of Formula (I) or (Ia), $Y^1$ is $NHC(=O)$, $L^4$ is $C_{1-6}$ alkylene, and the compound is also represented by Formula (Ic):

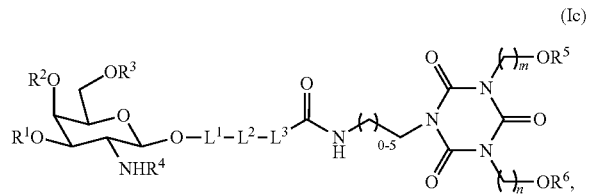

(Ic)

or a pharmaceutically acceptable salt thereof.

In some embodiments of the compounds of Formula (I), (Ia), (Ib) or (Ic), each of $R^1$, $R^2$ and $R^3$ is independently hydrogen, benzyl, or —$C(=O)R^8$, wherein $R^8$ is $C_{1-6}$ alkyl, $C_{1-6}$ haloalkyl, or optionally substituted phenyl. In some embodiments, $R^1$ is $C(=O)CH_3$. In some embodiments, $R^1$ is $C(=O)Ph$. In some embodiments, $R^2$ is $C(=O)CH_3$. In other embodiments, $R^2$ is $C(=O)Ph$. In some embodiments, $R^3$ is $C(=O)CH_3$. In other embodiments, $R^3$ is $C(=O)Ph$. In some embodiments, each of $R^1$, $R^2$ and $R^3$ is $C(=O)CH_3$. In some other embodiments, each of $R^1$, $R^2$ and $R^3$ is H. In some other embodiments, each of $R^1$, $R^2$ and $R^3$ is $C(=O)Ph$. In some embodiments, $R^4$ is —$C(=O)C_{1-6}$ alkyl. In other embodiments, $R^4$ is —$C(=O)C_{1-6}$ haloalkyl. In one embodiment, $R^4$ is —$C(=O)CH_3$. In another embodiment, $R^4$ is —$C(=O)CF_3$.

In some embodiments of the compounds of Formula (I), (Ia), (Ib) or (Ic), $R^5$ is a trityl type hydroxy protecting group. In one embodiment, $R^5$ is (4-methoxyphenyl)diphenylmethyl (i.e., monomethoxytrityl (MMTr)). In another embodiment, $R^5$ is bis(4-methoxyphenyl)phenylmethyl (i.e., 4,4'-dimethoxytrityl (DMTr)). In yet another embodiment, $R^5$ is tris(4-methoxyphenyl)methyl (i.e., 4,4',4''-trimethoxytrityl (TMTr)). In further embodiments, $R^5$ is 9-phenylxanthen-9-yl or 9-(4-methoxyphenyl)xanthen-9-yl.

In some embodiments of the compounds of Formula (I), (Ia), (Ib) or (Ic), $R^6$ is hydrogen. In other embodiments, $R^6$ is a phosphoramidite moiety. In yet other embodiments, $R^6$ is —$C(=O)CH_2CH_2C(=O)R^{6A}$, wherein $R^{6A}$ is —OH, —$OR^{10}$ or —$NR^{11}R^{12}$. In some embodiments, each of $R^{11}$ and $R^{12}$ is independently H, optionally substituted $C_{1-6}$ alkyl, or an amino protecting group. In other embodiments, $R^6$ is —$P(OR^{6B})NR^{6C}R^{6D}$, wherein each of $R^{6B}$, $R^{6C}$ and $R^{6D}$ is independently H, $C_{1-6}$ haloalkyl, or optionally substituted $C_{1-6}$ alkyl. In one embodiment, $R^6$ is —$C(=O)CH_2CH_2C(=O)OH$. In another embodiment, $R^6$ is

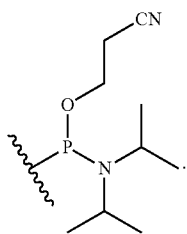 [SMILES: *P(OCCC#N)N(C(C)C)C(C)C]

In some embodiments of the compounds of Formula (I), (Ia), (Ib) or (Ic), each $L^1$, $L^2$, and $L^3$ is independently a bond, —$C(=O)$—, —$C(=S)$—, —$S(=O)_2$—, —$C(=O)NR^9$—, —$C(=S)NR^9$—, —$C(=O)O$—, —$C(=S)O$—, —$NR^9C(=O)NR^9$—, —$NR^9C(=S)NR^9$—, —$OP(=O)(OH)O$—, —$OP(=S)(OH)O$—, —O—, —S—, —$NR^9$—, optionally substituted $C_{1-10}$ alkylene, or optionally substituted 2 to 15 membered heteroalkylene wherein one or more carbon atoms (together with the hydrogen(s) attached to the carbon) are replaced with $C(=O)$, O, S or N, provided that at least one of $L^1$, $L^2$, and $L^3$ is not a bond. In some such embodiments, $R^9$ is H, unsubstituted or substituted $C_{1-6}$ alkyl, for example, methyl or trifluoromethyl. In some further embodiments, $L^1$ is a bond, $C_{1-10}$ alkylene, or 2 to 15 membered heteroalkylene, wherein one or more carbon atoms (i.e., $CH_2$) are replaced with $C(=O)$, O or N. In some embodiments, $L^1$ is a $C_{1-5}$ alkylene. In other embodiments, $L^1$ is 3 to 15 membered heteroalkylene comprising 1-5 units of PEG (i.e., $L^1$ is —$(CH_2CH_2O)$—$_{1-5}$). In such embodiments, $L^1$ is —$(CH_2CH_2O)_{1-5}(CH_2)_{1-5}$— such as —$(CH_2CH_2O)_2(CH_2)_2$—. In some other embodiments, $L^1$ is 2 to 10 or 2 to 6 membered straight heteroalkylene where one, two or three carbon atoms is replaced by N or $C(=O)$. In further embodiments, $L^1$ is a 2 to 6 membered heteroalkylene where one carbon is replaced by $C(=O)$ or N. In some embodiments, $L^2$ is —$C(=O)$—, —$C(=O)NR^9$—, —$NR^9$—, or 2 to 15 membered heteroalkylene, wherein one or more carbon atoms are replaced with $C(=O)$, 0 or N. In some such embodiments, $R^9$ is H or methyl. In other embodiments, $L^2$ is 3 to 15 membered heteroalkylene comprising 1-5 units of PEG (i.e., $L^2$ is —$(CH_2CH_2O)$—$_{1-5}$). In some other embodiments, $L^2$ is 2 to 10 or 2 to 6 membered straight heteroalkylene where one, two or three carbon atoms is replaced by N or $C(=O)$. In further embodiments, $L^2$ is a 2 to 6 membered heteroalkylene where one carbon is replaced by $C(=O)$ or N. In some further embodiments, $L^3$ is a bond, $C_{1-10}$ alkylene, or 2 to 15 membered heteroalkylene, wherein one or more carbon atoms are replaced with $C(=O)$, O or N. In some embodiments, $L^3$ is a $C_{1-5}$ alkylene for example, $C_1$, $C_2$, $C_3$, $C_4$ or $C_5$ alkylene. In such embodiments, $L^3$ is —$(CH_2)$—, —$(CH_2)_2$—, —$(CH_2)_3$—, or —$(CH_2)_4$—. In other embodiments, $L^3$ is 3 to 15 membered heteroalkylene comprising 1-5 units of PEG (i.e., $L^3$ is —$(CH_2CH_2O)$—$_{1-5}$). In some other embodiments, $L^3$ is 2 to 10 or 2 to 6 membered straight heteroalkylene where one, two or three carbon atoms is replaced by nitrogen or C(=O). In further embodiments, $L^3$ is a 2 to 6 membered heteroalkylene where one carbon is replaced by C(=O) or N. In some embodiments, only $L^1$ is a bond. In some embodiments, only $L^2$ is a bond. In some embodiments, only $L^3$ is a bond. In other embodiments, two of $L^1$, $L^2$ and $L^3$ are each a bond. In other embodiments, at least one of $L^1$, $L^2$, and $L^3$ is a ring or ring system including optionally substituted $C_{6-10}$ arylene (e.g., phenylene), optionally substituted $C_{3-10}$ cycloalkylene (e.g., $C_{3-7}$ cycloalkylene), optionally substituted 5-10 membered heteroarylene (e.g., 5 or 6 membered heteroarylene containing one, two or three heteroatoms selected from O, N or S), and optionally substituted 5 to 10 membered heterocyclylene (e.g., five or six membered heterocyclylene such as piperidylene, piperazinylene or morpholinylene). Non-limiting examples of -$L^1$-$L^2$-$L^3$- include: —(CH$_2$CH$_2$O)—$_{1-10}$, —(CH$_2$)$_{0-6}$—(CH$_2$CH$_2$O)$_{1-8}$—(CH$_2$)$_{0-6}$—, —(CH$_2$CH$_2$O)$_2$—(CH$_2$)$_2$—, —(CH$_2$CH$_2$O)$_3$—(CH$_2$)$_2$—,

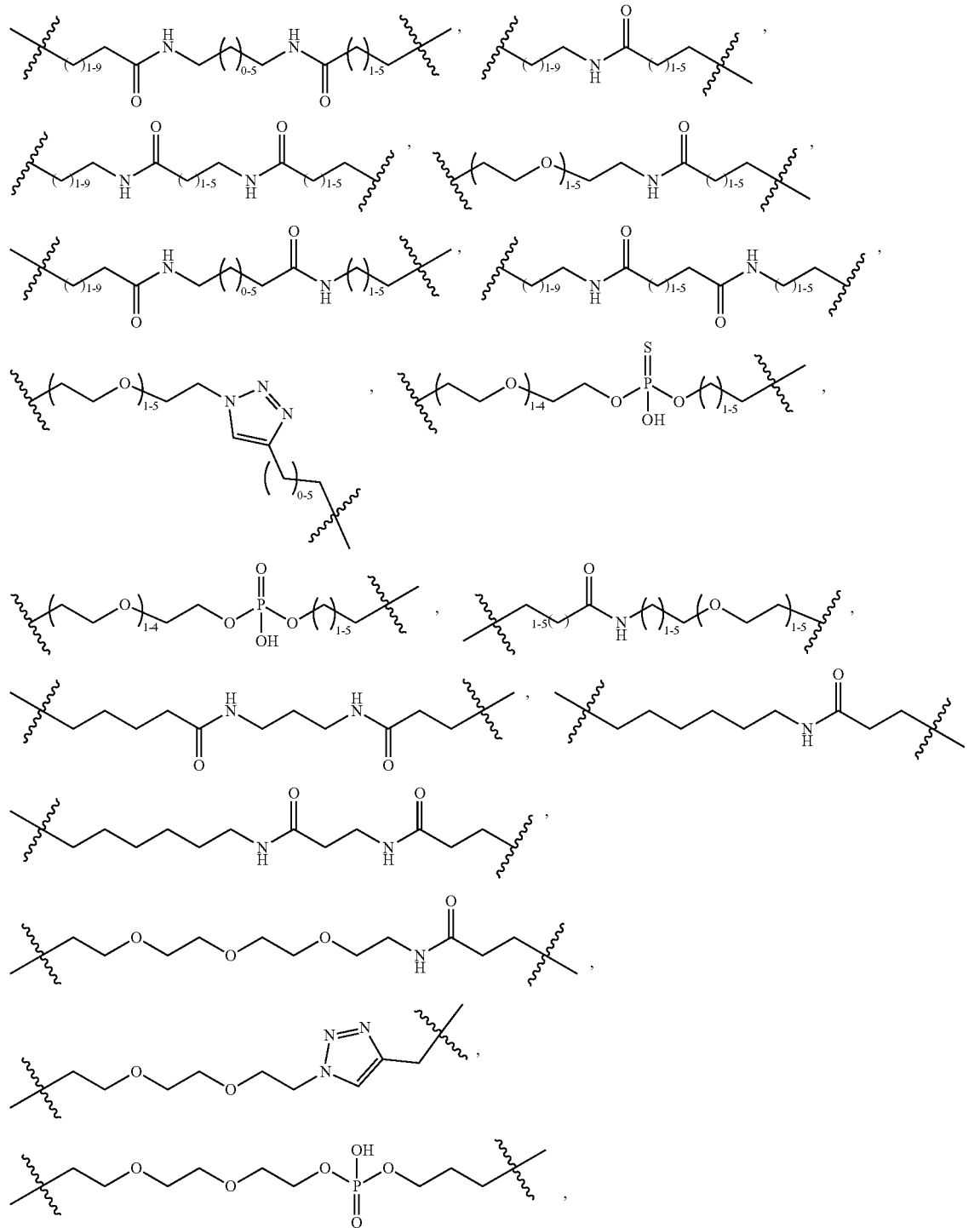

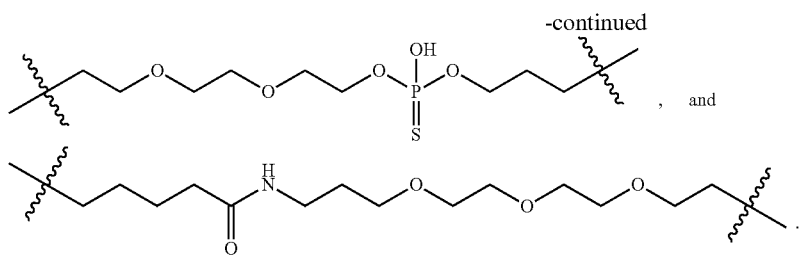

, and

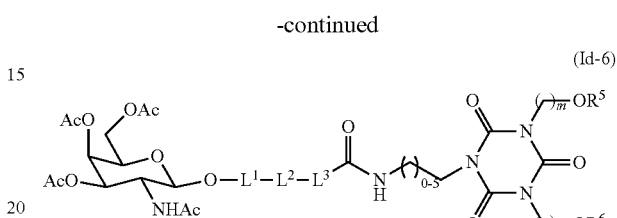

.

In some embodiments of the compounds of Formula (I), (Ia) or (Ib), m is 1 and n is 2. In other embodiments, m is 2 and n is 1. In other embodiments, both m and n are 1. In other embodiments, both m and n are 2. In other embodiments, both m and n are 3.

Further embodiments of the compounds of Formula (I) include:

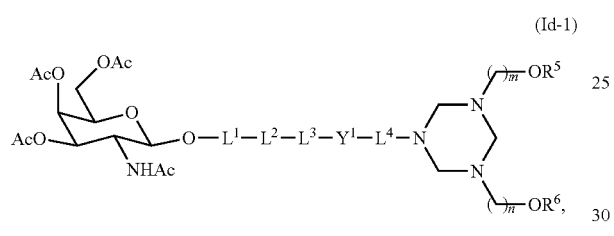
(Id-1)

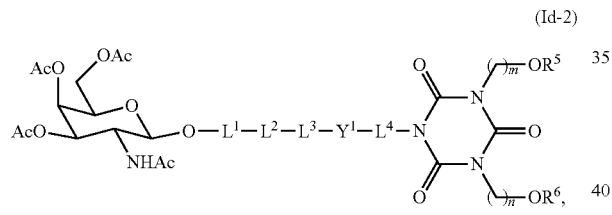
(Id-2)

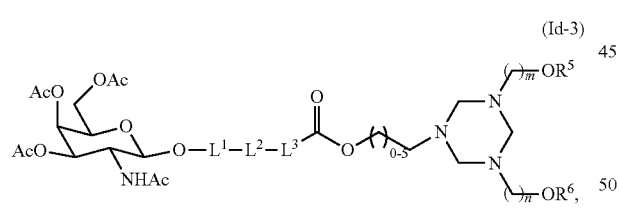
(Id-3)

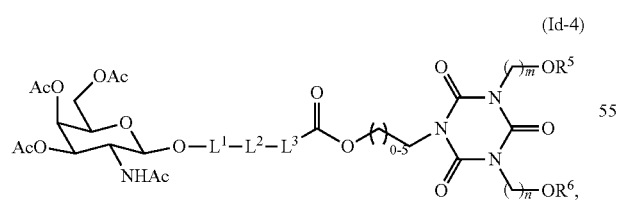
(Id-4)

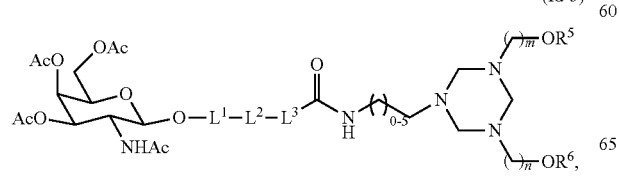
(Id-5)

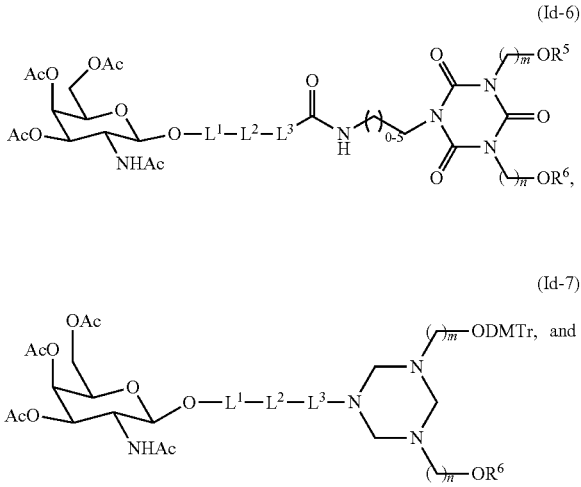
(Id-6), (Id-7), (Id-8)

and pharmaceutically acceptable salts thereof, wherein $L^1$, $L^2$ and $L^3$ are defined herein, Ac is —C(O)CH$_3$, each of m and n is independently 1 or 2, and $R^6$ is —C(=O)CH$_2$CH$_2$C(=O)OH or

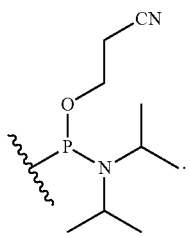 [SMILES: *P(OCCC#N)N(C(C)C)C(C)C]

In further embodiments, each of $L^1$, $L^2$ and $L^3$ is independently a bond, $C_{1-10}$ alkylene, 3 to 15 membered heteroalkylene where one or more carbon atoms are replaced with C(=O), O or N, or a PEG linker comprising one to five —OCH$_2$CH$_2$— repeating unit.

Additional non-limiting examples of the compounds of Formula (I) include:
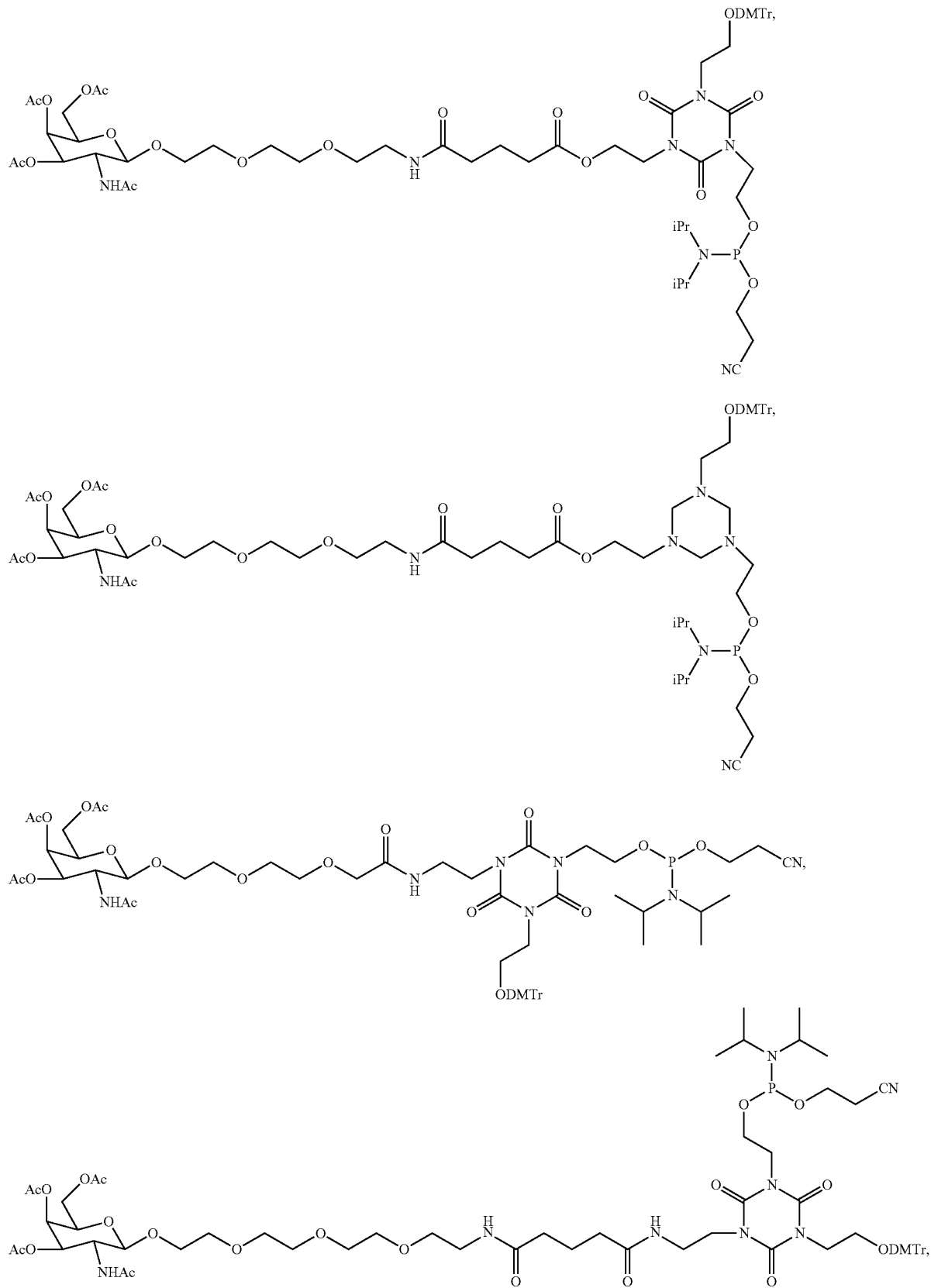

-continued
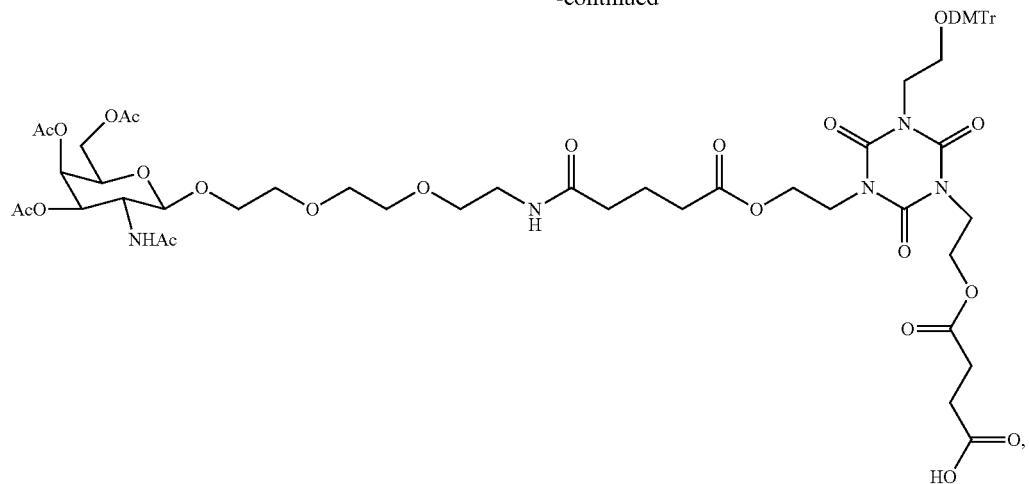
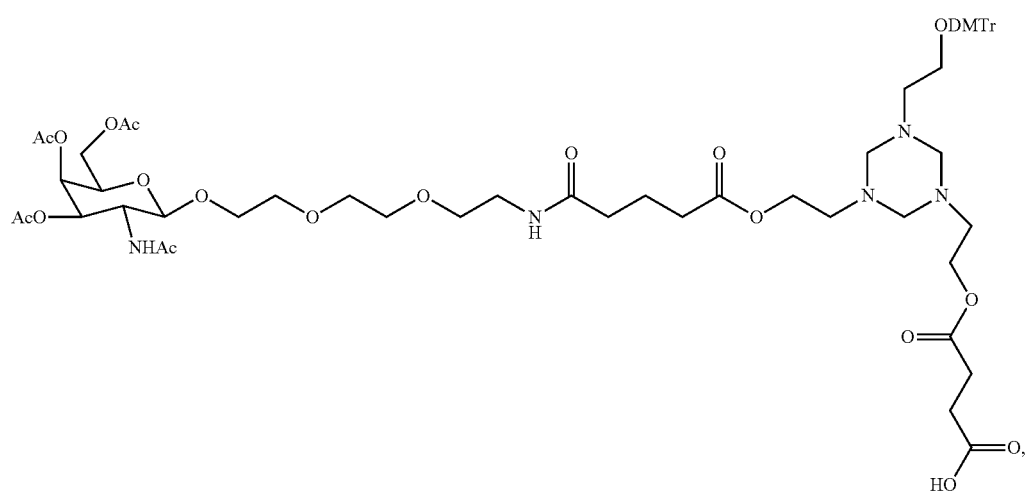
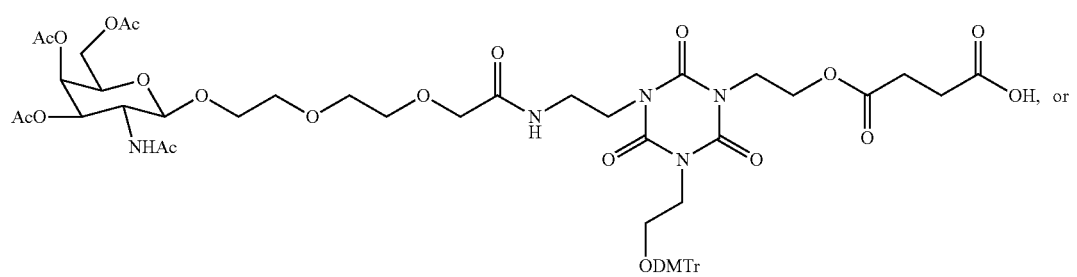
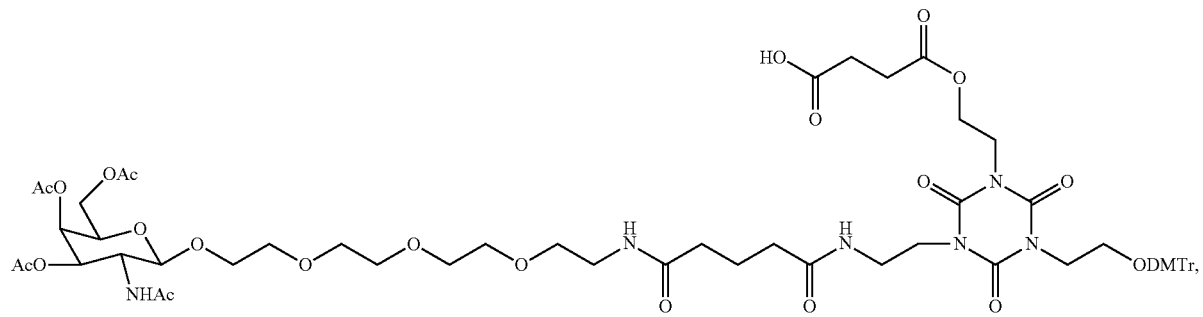
or a pharmaceutically acceptable salt thereof.

Trivalent GalNAc Analogs of Formula (II)

Some embodiments provide a compound of Formula (II), or a pharmaceutically acceptable salt thereof as described herein:

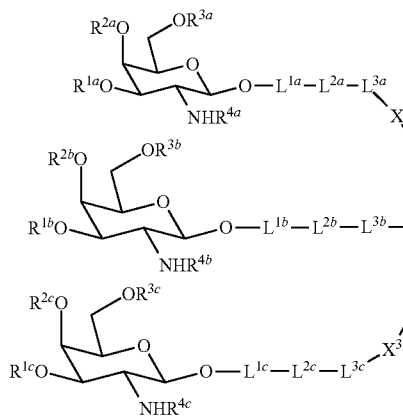 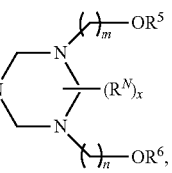

(II)

or a pharmaceutically acceptable salt thereof, wherein
each of $R^{1a}$, $R^{1b}$, $R^{1c}$, $R^{2a}$, $R^{2b}$, $R^{2c}$, $R^{3a}$, $R^{3b}$, and $R^{3c}$ is independently hydrogen, benzyl, or —C(=O)$R^8$;

each of $R^{4a}$, $R^{4b}$ and $R^{4c}$ is independently —C(=O)$C_{1-6}$ alkyl or —C(=O)$C_{1-6}$ haloalkyl;

$R^5$ is a hydroxy protecting group;

$R^6$ is hydrogen, a phosphoramidite moiety, —C(=O)CH$_2$CH$_2$C(=O)$R^{6A}$, or —P(O$R^{6B}$)N$R^{6C}R^{6D}$;

$Y^2$ is a bond, N$R^7$, N$R^7$C(=O), C(=O)O, or O;

each of $X^1$, $X^2$ and $X^3$ is independently —O(CH$_2$)$_{1-3}$—, —NH(CH$_2$)$_{1-3}$—, —NHC(=O)(CH$_2$)$_{1-3}$—, or —C(=O)(CH$_2$)$_{1-3}$—;

each of $L^{1a}$, $L^{1b}$, $L^{1c}$, $L^{2a}$, $L^{2b}$, $L^{2c}$, $L^{3a}$, $L^{3b}$, and $L^{3c}$ is independently a bond, —C(=O)—, —C(=S)—, —S(=O)$_2$—, —C(=O)N$R^9$—, —C(=S)N$R^9$—, —C(=O)O—, —C(=S)O—, —N$R^9$C(=O)N$R^9$—, —N$R^9$C(=S)N$R^9$—, —OP(=O)(OH)O—, —OP(=S)(OH)O—, —O—, —S—, —N$R^9$—, optionally substituted $C_{1-10}$ alkylene, optionally substituted $C_{6-10}$ arylene, optionally substituted $C_{3-10}$ cycloalkylene, optionally substituted 5-10 membered hetetroarylene, optionally substituted 5 to 10 membered heterocyclylene, or optionally substituted 2 to 15 membered heteroalkylene wherein one or more carbon atoms are replaced with C(=O), O, S or N, provided that at least one of $L^{1a}$, $L^{1b}$ and $L^{1c}$ is not a bond, at least one of $L^{2a}$, $L^{2b}$ and $L^{2c}$ is not a bond, and at least one of $L^{3a}$, $L^{3b}$ and $L^{3c}$, is not a bond;

$L^4$ is a bond, optionally substituted $C_{1-8}$ alkylene or —(CH$_2$)$_{1-3}$(OCH$_2$CH$_2$)$_{1-5}$OCH$_2$—;

$L^5$ is a bond, optionally substituted $C_{1-10}$ alkylene, or optionally substituted 2 to 15 membered heteroalkylene wherein one or more carbon atoms are replaced with C(=O), O, S or N;

each of $R^7$ and $R^9$ is independently hydrogen, unsubstituted $C_{1-6}$ alkyl, or substituted $C_{1-6}$ alkyl;

each $R^8$ is independently $C_{1-6}$ alkyl, $C_{1-6}$ haloalkyl, or optionally substituted phenyl;

$R^{6A}$ is —OH, —O$R^{10}$ or —N$R^{11}R^{12}$.

each of $R^{6B}$, $R^{6C}$ and $R^{6D}$ is independently H, $C_{1-6}$ haloalkyl, or unsubstituted or substituted $C_{1-6}$ alkyl;

$R^{10}$ is unsubstituted or substituted $C_{1-6}$ alkyl, or a hydroxy protecting group;

each of $R^{11}$ and $R^{12}$ is independently H, unsubstituted or substituted $C_{1-6}$ alkyl, or an amino protecting group;

each of m and n is independently 1, 2, 3, 4, 5 or 6;

k is 0 or 1;

x is 0, 1, 2, 3, 4, 5 or 6; and each $R^N$ is independently halo, cyano, hydroxy, amino, unsubstituted $C_{1-6}$ alkyl, substituted $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl, or two adjacent $R^N$ attached to the same carbon atom form oxo (=O).

In some embodiments of the compounds of Formula (II), k is 0. In some embodiments, k is 1. In some embodiments, $R^7$ is hydrogen. In other embodiments, $R^7$ is $C_{1-4}$ alkyl, such as methyl, ethyl, n-propyl, isopropyl, n-butyl, or t-butyl.

In some embodiments of the compounds of Formula (II), k is 0, $R^7$ is H, and the compound is also represented by Formula (IIa):

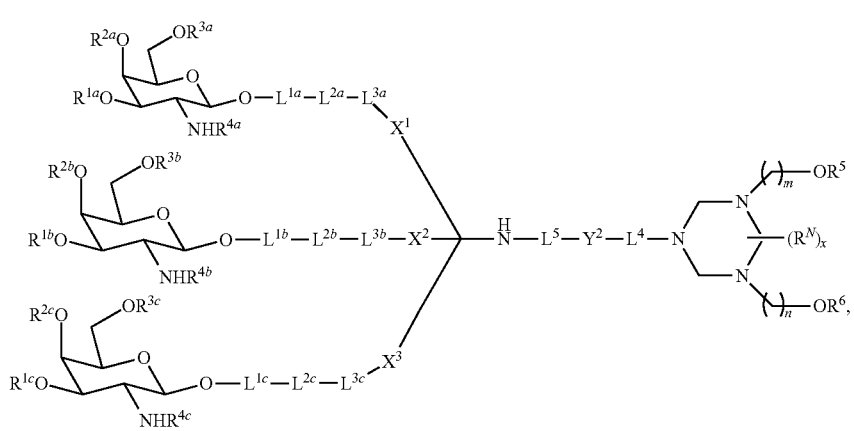

(IIa)

or a pharmaceutically acceptable salt thereof.

In some embodiments of the compounds of Formula (II) or (IIa), x is 0. In some embodiments, x is 1. In some embodiments, x is 2. In such embodiments, two adjacent $R^N$ attached to the same carbon atom form oxo (═O). In some embodiments, x is 3. In some embodiments, x is 4. In such embodiments, a first pair of two adjacent $R^N$ attached to a first carbon atom forms a first oxo (═O) group and a second pair of two adjacent $R^N$ attached to a second carbon atom forms a second oxo (═O) group. In some embodiments, x is 5. In some embodiments, x is 6. In such embodiments, a first pair of two adjacent $R^N$ attached to a first carbon atom forms a first oxo (═O) group, a second pair of two adjacent $R^N$ attached to a second carbon atom forms a second oxo (═O) group, and a third pair of two adjacent $R^N$ attached to a third carbon atom forms a third oxo (═O) group.

In some embodiments of the compounds of Formula (II), k is 0, $R^7$ is H, and the compound is also represented by Formula (IIb):

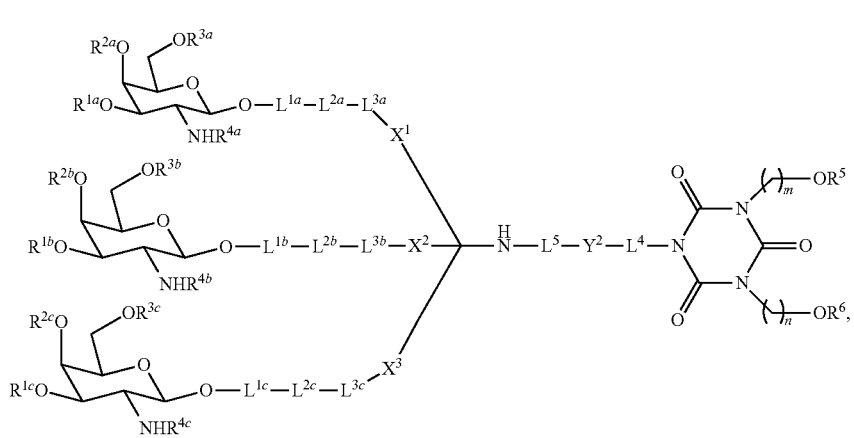

(IIb)

or a pharmaceutically acceptable salt thereof.

In some embodiments of the compounds of Formula (II), (IIa) or (IIb), $Y^2$ is $NR^7$. In some embodiments, $Y^2$ is $NR^7C(═O)$. In such embodiments, $R^7$ is H. In other such embodiments, $R^7$ is $C_{1-4}$ alkyl, such as methyl, ethyl, n-propyl, isopropyl, n-butyl, or t-butyl. In some embodiments, $Y^2$ is C(═O)O. In some embodiments, $Y^2$ is O. In some embodiments, $Y^2$ is a bond.

In some embodiments of the compounds of Formula (II), (IIa) or (IIb), $L^4$ is a straight chain unsubstituted $C_{1-6}$ alkylene, for example, $C_1$, $C_2$, $C_3$, $C_4$ or $C_5$ alkylene. In such embodiments, $L^4$ is —(CH$_2$)—, —(CH$_2$)$_2$—, —(CH$_2$)$_3$—, or —(CH$_2$)$_4$—. In some other embodiments, $L^4$ is a bond.

In some embodiments of the compounds of Formula (II), k is 0, $R^7$ is H, $Y^2$ is C(═O)O, and the compound is also represented by Formula (IIc):

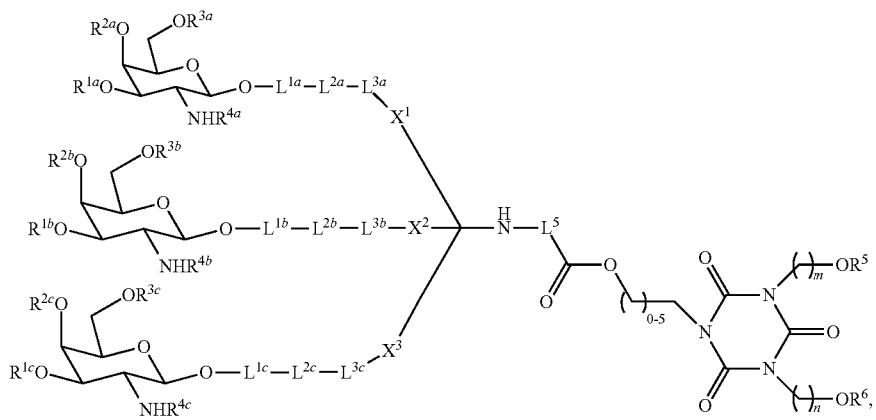

(IIc)

or a pharmaceutically acceptable salt thereof.

In some embodiments of the compounds of Formula (II), k is 0, $R^7$ is H, $Y^2$ is NHC(=O), and the compound is also represented by Formula (IId):

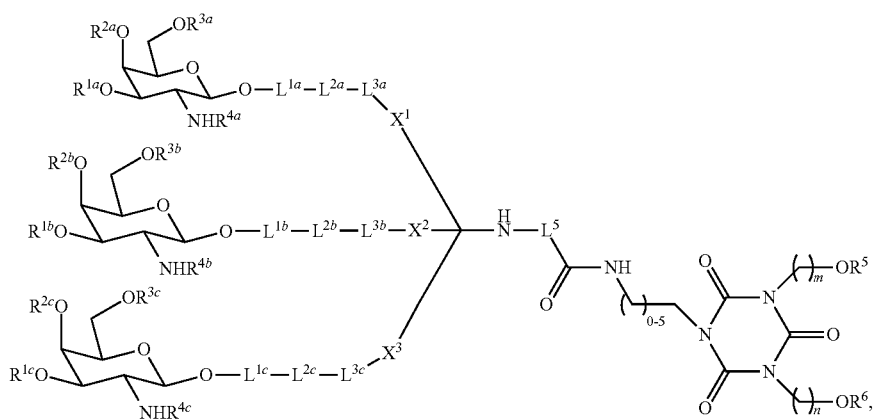

(IId)

or a pharmaceutically acceptable salt thereof.

In some embodiments of the compounds of Formula (II), (IIa), (IIb), (IIc) or (IId), $L^5$ is 2 to 15 membered heteroalkylene where one or more carbon atoms are replaced with C(=O), O or N. In such embodiments, $L^5$ is —C(=O)—(CH$_2$)$_{1-5}$—. In one embodiment, $L^5$ is —C(=O)—(CH$_2$)$_3$—. In another embodiment, $L^5$ is —C(=O)—(CH$_2$)$_2$—. In some other embodiments, $L^5$ is a bond.

In some embodiments of the compounds of Formula (II), (IIa), (IIb), (IIc) or (IId), each of $R^{1a}$, $R^{2a}$, $R^{3a}$, $R^{2a}$, $R^{2b}$, $R^{3b}$, $R^{1c}$, $R^{2c}$ and $R^{3c}$ is independently hydrogen, benzyl, or —C(=O)$R^8$, wherein $R^8$ is C$_{1-6}$ alkyl, C$_{1-6}$ haloalkyl, or optionally substituted phenyl. In some embodiments, $R^{1a}$ is C(=O)CH$_3$. In some embodiments, $R^{1a}$ is C(=O)Ph. In some embodiments, $R^{2a}$ is C(=O)CH$_3$. In other embodiments, $R^{2a}$ is C(=O)Ph. In some embodiments, $R^{3a}$ is C(=O)CH$_3$. In other embodiments, $R^{3a}$ is C(=O)Ph. In some embodiments, each of $R^{1a}$, $R^{2a}$ and $R^{3a}$ is C(=O)CH$_3$. In some other embodiments, each of $R^{1a}$, $R^{2a}$ and $R^{3a}$ is H. In some other embodiments, each of $R^{1a}$, $R^{2a}$ and $R^{3a}$ is C(=O)Ph. In some embodiments, $R^{4a}$ is —C(=O)C$_{1-6}$ alkyl. In other embodiments, $R^{4a}$ is —C(=O)C$_{1-6}$ haloalkyl. In one embodiment, $R^{4a}$ is —C(=O)CH$_3$. In another embodiment, $R^{4a}$ is —C(=O)CF$_3$. In some embodiments, $R^{1b}$ is C(=O)CH$_3$. In some embodiments, $R^{1b}$ is C(=O)Ph. In some embodiments, $R^{2b}$ is C(=O)CH$_3$. In other embodiments, $R^{2b}$ is C(=O)Ph. In some embodiments, $R^{3b}$ is C(=O)CH$_3$. In other embodiments, $R^{3b}$ is C(=O)Ph. In some embodiments, each of $R^{1b}$, $R^{2b}$ and $R^{3b}$ is C(=O)CH$_3$. In some other embodiments, each of $R^{1b}$, $R^{2b}$ and $R^{3b}$ is H. In some other embodiments, each of $R^{1b}$, $R^{2b}$ and $R^{3b}$ is C(=O)Ph. In some embodiments, $R^{4b}$ is —C(=O)C$_{1-6}$ alkyl. In other embodiments, $R^{4b}$ is —C(=O)C$_{1-6}$ haloalkyl. In one embodiment, $R^{4b}$ is —C(=O)CH$_3$. In another embodiment, $R^{4b}$ is —C(=O)CF$_3$. In some embodiments, $R^{1c}$ is C(=O)CH$_3$. In some embodiments, $R^{1c}$ C is C(=O)Ph. In some embodiments, $R^{2c}$ is C(=O)CH$_3$. In other embodiments, $R^{2c}$ is C(=O)Ph. In some embodiments, $R^{3c}$ is C(=O)CH$_3$. In other embodiments, $R^3$, is C(=O)Ph. In some embodiments, each of $R^{1c}$, $R^{2c}$ and $R^{3c}$ is C(=O)CH$_3$. In some other embodiments, each of $R^{1c}$, $R^{2c}$ and $R^{3c}$ is H. In some other embodiments, each of $R^{1c}$, $R^{2c}$ and $R^{3c}$ is C(=O)Ph. In some embodiments, $R^{4c}$ is —C(=O)C$_{1-6}$ alkyl. In other embodiments, $R^{4c}$ is —C(=O)C$_{1-6}$ haloalkyl. In one embodiment, $R^{4c}$ is —C(=O)CH$_3$. In another embodiment, $R^{4c}$ is —C(=O)CF$_3$.

In some embodiments of the compounds of Formula (II), (IIa), (IIb), (IIc) or (IId), $R^5$ is a trityl type hydroxy protecting group. In one embodiment, $R^5$ is (4-methoxyphenyl) diphenylmethyl (i.e., monomethoxytrityl (MMTr)). In another embodiment, $R^5$ is bis(4-methoxyphenyl)phenylmethyl (i.e., 4,4'-dimethoxytrityl (DMTr)). In yet another embodiment, $R^5$ is tris(4-methoxyphenyl)methyl (i.e., 4,4',4"-trimethoxytrityl (TMTr)). In further embodiments, $R^5$ is 9-phenylxanthen-9-yl or 9-(4-methoxyphenyl)xanthen-9-yl.

In some embodiments of the compounds of Formula (II), (IIa), (IIb), (IIc) or (IId), $R^6$ is hydrogen. In other embodiments, $R^6$ is a phosphoramidite moiety. In yet other embodiments, $R^6$ is —C(=O)CH$_2$CH$_2$C(=O)$R^{6A}$, wherein $R^{6A}$ is —OH, —$OR^{10}$ or —$NR^{11}R^{12}$. In some embodiments, each of $R^{11}$ and $R^{12}$ is independently H, optionally substituted $C_{1-6}$ alkyl, or an amino protecting group. In other embodiments, $R^6$ is —P(O$R^{6B}$)N$R^{6C}R^{6D}$, wherein each of $R^{6B}$, $R^{6C}$ and $R^{6D}$ is independently H, $C_{1-6}$ haloalkyl, or optionally substituted $C_{1-6}$ alkyl. In one embodiment, $R^6$ is —C(=O) CH$_2$CH$_2$C(=O)OH. In another embodiment, $R^6$ is

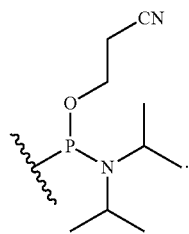 [SMILES: *P(OCCC#N)N(C(C)C)C(C)C]

In some embodiments of the compounds of Formula (II), (IIa), (IIb), (IIc) or (IId), each of $X^1$ and $X^3$ is —NH(=O) CH$_2$CH$_2$—, and $X^2$ is —NHC(=O)CH$_2$—. In other embodiments, each of $X^1$ and $X^3$ is -C(=O)CH$_2$CH$_2$—, and $X^2$ is —C(=O)CH$_2$—. In one embodiment, each of $X^1$, $X^2$ and $X^3$ is —OCH$_2$—. In another embodiment, each of $X^1$, $X^2$ and $X^3$ is —NHCH$_2$—. In another embodiment, each of $X^1$, $X^2$ and $X^3$ is —C(=O)CH$_2$CH$_2$—. In another embodiment, each of $X^1$, $X^2$ and $X^3$ is —C(=O)CH$_2$—. In another embodiment, each of $X^1$, $X^2$ and $X^3$ is —NHC(=O) CH$_2$CH$_2$—. In another embodiment, each of $X^1$, $X^2$ and $X^3$ is —NHC(=O)CH$_2$—.

In some embodiments of the compounds of Formula (II), (IIa), IIb), (IIc) or (IId), each $L^{1a}$, $L^{1b}$, $L^{1c}$, $L^{2a}$, $L^{2b}$, $L^{2c}$, $L^{3a}$, $L^{3b}$, and $L^{3c}$ is independently a bond, —C(=O)—, —C(=S)—, —S(=O)$_2$—, —C(=O)$NR^9$—, —C(=S) $NR^9$—, —C(=O)O—, —C(=S)O—, —$NR^9$C(=O) $NR^9$—, —$NR^9$C(=S)$NR^9$—, —OP(=O)(OH)O—, —OP (=S)(OH)O—, —O—, —S—, —$NR^9$—, optionally substituted $C_{1-10}$ alkylene, or optionally substituted 2 to 15 membered heteroalkylene wherein one or more carbon atoms (together with the hydrogen(s) attached to the carbon) are replaced with C(=O), O, S or N, provided that at least one of $L^{1a}$, $L^{1b}$ and $L^{1c}$ is not a bond, at least one of $L^{2a}$, $L^{2b}$ and $L^{2c}$ is not a bond, and at least one of $L^{3a}$, $L^{3b}$ and $L^{3c}$ is not a bond. In some such embodiments, $R^9$ is H, unsubstituted or substituted $C_{1-6}$ alkyl, for example, methyl or trifluoromethyl. In some further embodiments, each of $L^{1a}$, $L^{1b}$ and $L^{1c}$ is independently a bond, $C_{1-10}$ alkylene, or 2 to 15 membered heteroalkylene, wherein one or more carbon atoms (i.e., CH$_2$) are replaced with C(=O), O or N. In some embodiments, each of $L^{1a}$, $L^{1b}$ and $L^{1c}$ is independently a $C_{1-5}$ alkylene. In other embodiments, each of $L^{1a}$, $L^{1b}$ and $L^{1c}$ is independently 3 to 15 membered heteroalkylene comprising 1-5 units of PEG (i.e., each of $L^{1a}$, $L^{1b}$ and $L^{1c}$ is independently —(CH$_2$CH$_2$O)—$_{1-5}$). In some other embodiments, each of $L^{1a}$, $L^{1b}$ and $L^{1c}$ is independently 2 to 10 or 2 to 6 membered straight heteroalkylene where one, two or three carbon atoms is replaced by N or C(=O). In further embodiments, each of $L^{1a}$, $L^{1b}$ and $L^{1c}$ is independently a 2 to 6 membered heteroalkylene where one carbon is replaced by C(=O) or N. In some embodiments, each of $L^{2a}$, $L^{2b}$ and $L^{2c}$ is independently —C(=O)—, —C(=O) $NR^9$—, —$NR^9$—, or 2 to 15 membered heteroalkylene, wherein one or more carbon atoms are replaced with C(=O), O or N. In some such embodiments, $R^9$ is H or methyl. In other embodiments, each of $L^{2a}$, $L^{2b}$ and $L^{2c}$ is independently 3 to 15 membered heteroalkylene comprising 1-5 units of PEG (i.e., each of $L^{2a}$, $L^{2b}$ and $L^{2c}$ is independently —(CH$_2$CH$_2$O)—$_{1-5}$). In some other embodiments, each of $L^{2a}$, $L^{2b}$ and $L^{2c}$ is independently 2 to 10 or 2 to 6 membered straight heteroalkylene where one, two or three carbon atoms is replaced by N or C(=O). In further embodiments, each of $L^{2a}$, $L^{2b}$ and $L^{2c}$ is independently a 2 to 6 membered heteroalkylene where one carbon is replaced by C(=O) or N. In some further embodiments, each of $L^{3a}$, $L^{3b}$ and $L^{3c}$ is independently a bond, $C_{1-10}$ alkylene, or 2 to 15 membered heteroalkylene, wherein one or more carbon atoms are replaced with C(=O), O or N. In some embodiments, each of $L^{3a}$, $L^{3b}$ and $L^{3c}$ is independently a $C_{1-5}$ alkylene. In other embodiments, each of $L^{3a}$, $L^{3b}$ and $L^{3c}$ is independently 3 to 15 membered heteroalkylene comprising 1-5 units of PEG (i.e., each of $L^{3a}$, $L^{3b}$ and $L^{3c}$ is independently —(CH$_2$CH$_2$O)—$_{1-5}$). In some other embodiments, each of $L^{3a}$, $L^{3b}$ and $L^{3c}$ is independently 2 to 10 or 2 to 6 membered straight heteroalkylene where one, two or three carbon atoms is replaced by nitrogen or C(=O). In further embodiments, each of $L^{3a}$, $L^{3b}$ and $L^{3c}$ is independently a 2 to 6 membered heteroalkylene where one carbon is replaced by C(=O) or N. In some embodiments, only $L^1$ is a bond. In some embodiments, only $L^{2a}$, $L^{2b}$ and $L^{2c}$ are a bond. In some embodiments, only $L^{3a}$, $L^{3b}$ and $L^{3c}$ are a bond. In other embodiments, two of $L^1a$, $L^2a$ and $L^3a$ are each a bond. In other embodiments, two of $L^{1b}$, $L^{2b}$ and $L^{3b}$ are each a bond. In other embodiments, two of $L^{1c}$, $L^{2c}$ and $L^{3c}$ are each a bond. In other embodiments, at least one of $L^{1a}$, $L^{2a}$ and $L^{3a}$, one of $L^{1b}$, $L^{2b}$ and $L^{3b}$, and/or one of $L^{1c}$, $L^{2c}$ and $L^{3c}$ is a ring or ring system including optionally substituted $C_{6-10}$ arylene (e.g., phenylene), optionally substituted $C_{3-10}$ cycloalkylene (e.g., $C_{3-7}$ cycloalkylene), optionally substituted 5-10 membered heteroarylene (e.g., 5 or 6 membered heteroarylene containing one, two or three heteroatoms selected from O, N or S), and optionally substituted 5 to 10 membered heterocyclylene (e.g., five or six membered heterocyclylene such as piperidylene, piperazinylene or morpholinylene). Non-limiting examples of -$L^{1a}$-$L^{2a}$-$L^{3a}$-, -$L^{1b}$-$L^{2b}$-$L^{3b}$- or -$L^{1c}$-$L^{2c}$-$L^{3c}$- include: —(CH$_2$CH$_2$O)—$_{1-10}$, —(CH$_2$)$_{0-6}$—(CH$_2$CH$_2$O)$_{1-8}$—(CH$_2$)$_{0-6}$—, —(CH$_2$CH$_2$O)$_2$—(CH$_2$)$_2$—, —(CH$_2$CH$_2$O)$_3$—(CH$_2$)$_2$—,

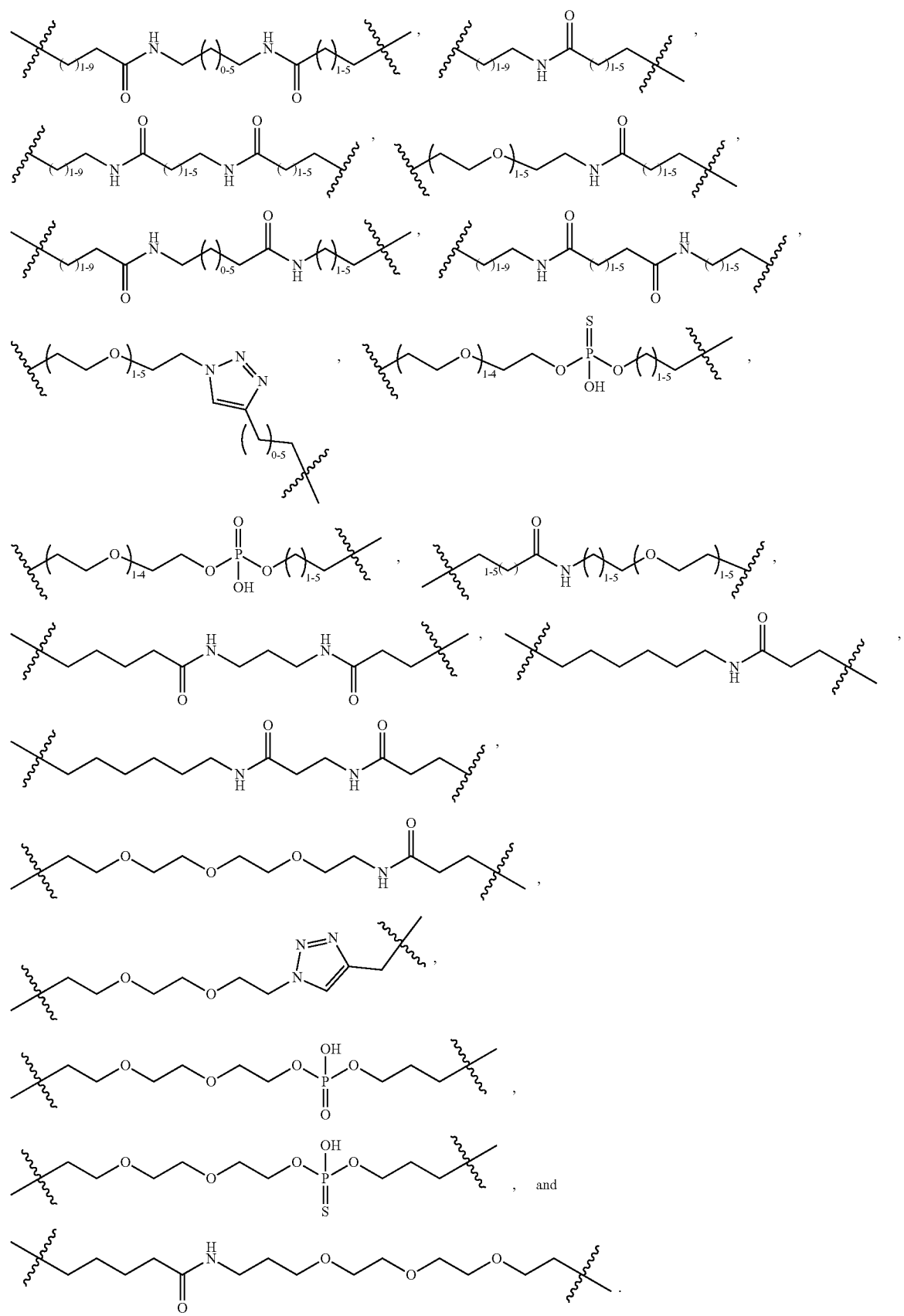

In some embodiments of the compounds of Formula (II), (IIa), (IIb), (IIc) or (IId), m is 1 and n is 2. In other embodiments, m is 2 and n is 1. In other embodiments, both m and n are 1. In other embodiments, both m and n are 2. In other embodiments, both m and n are 3.
Further embodiments of the compounds of Formula (II) have the formula selected from the group consisting of:
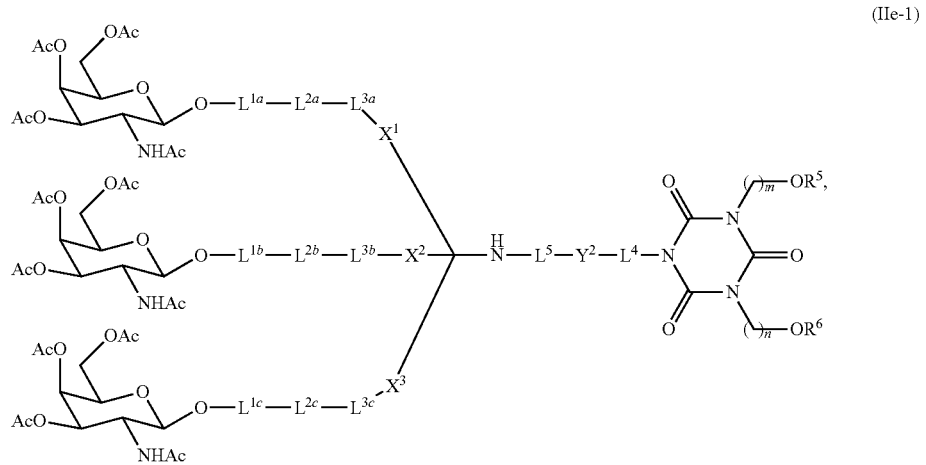
(IIe-1)
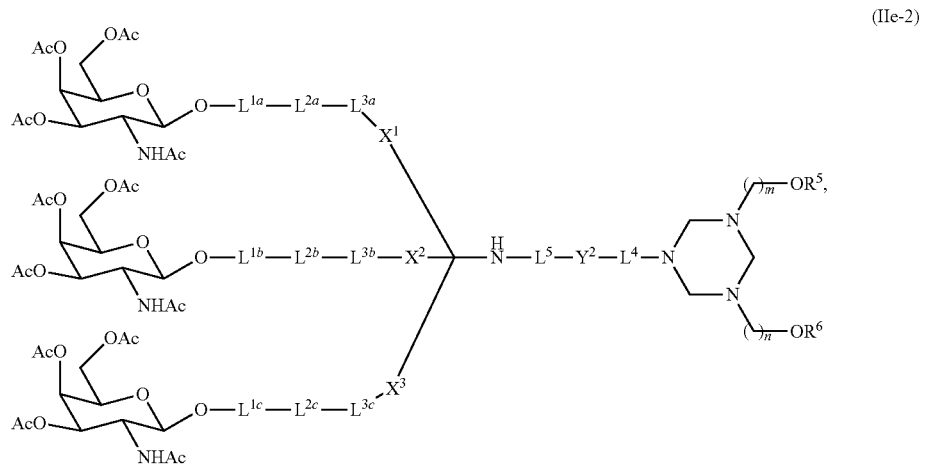
(IIe-2)
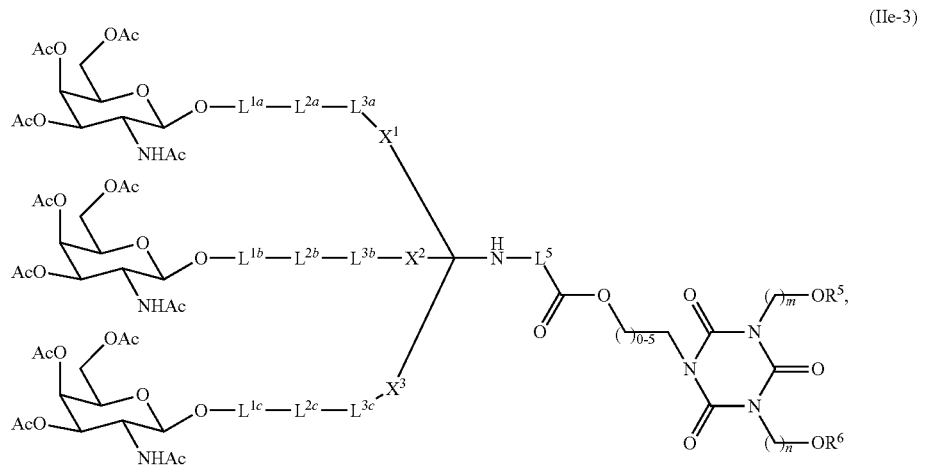
(IIe-3)

(IIe-4)
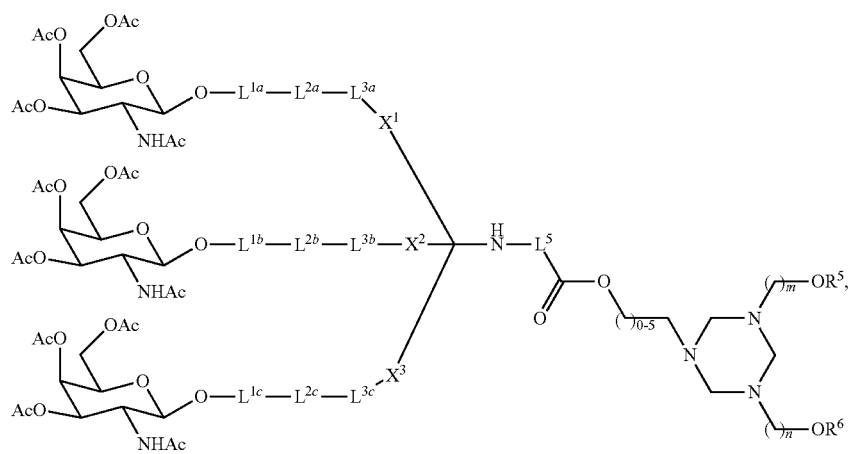
(IIe-5)
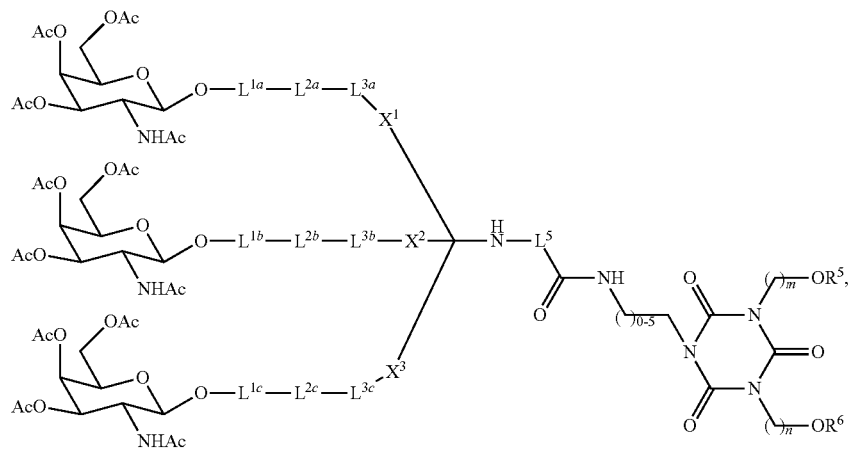
(IIe-6)
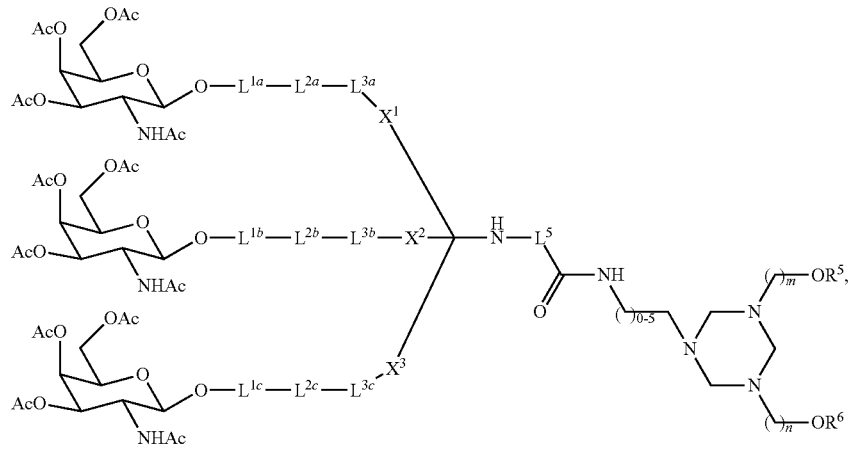

-continued

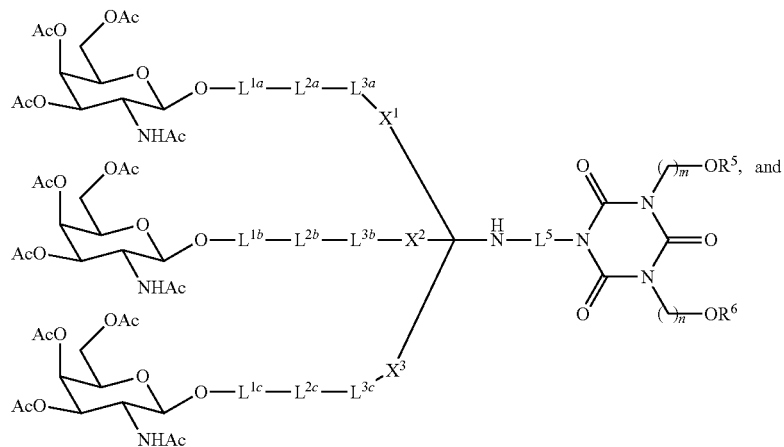

(IIe-7)

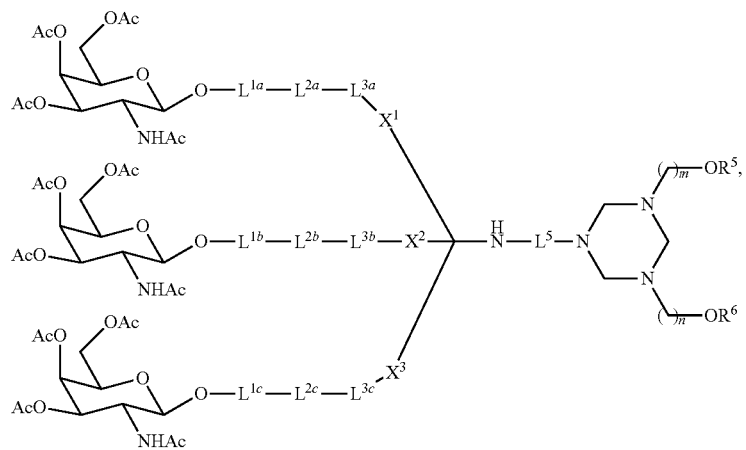

(IIe-8)

or a pharmaceutically acceptable salt thereof, wherein
each of $X^1$, $X^2$ and $X^3$ is —OCH$_2$—, —NHCH$_2$—, —C(=O)CH$_2$CH$_2$—, —C(=O)CH$_2$—, —NHC(=O)CH$_2$CH$_2$— or —NHC(=O)CH$_2$—, or each of $X^1$ and $X^3$ is -C(=O)CH$_2$CH$_2$—, and $X^2$ is —C(=O)CH$_2$—, or each of $X^1$ and $X^3$ is —NHC(=O)CH$_2$CH$_2$—, and $X^2$ is —NHC(=O)CH$_2$—;

Ac is —C(O)CH$_3$;

each of m and n is independently 1 or 2;

$R^5$ is DMTr; and $R^6$ is —C(=O)CH$_2$CH$_2$C(=O)OH or

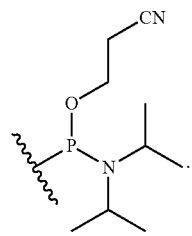 [SMILES: *P(OCCC#N)N(C(C)C)C(C)C]

Additional non-limiting examples of the compounds of Formula (II) include:
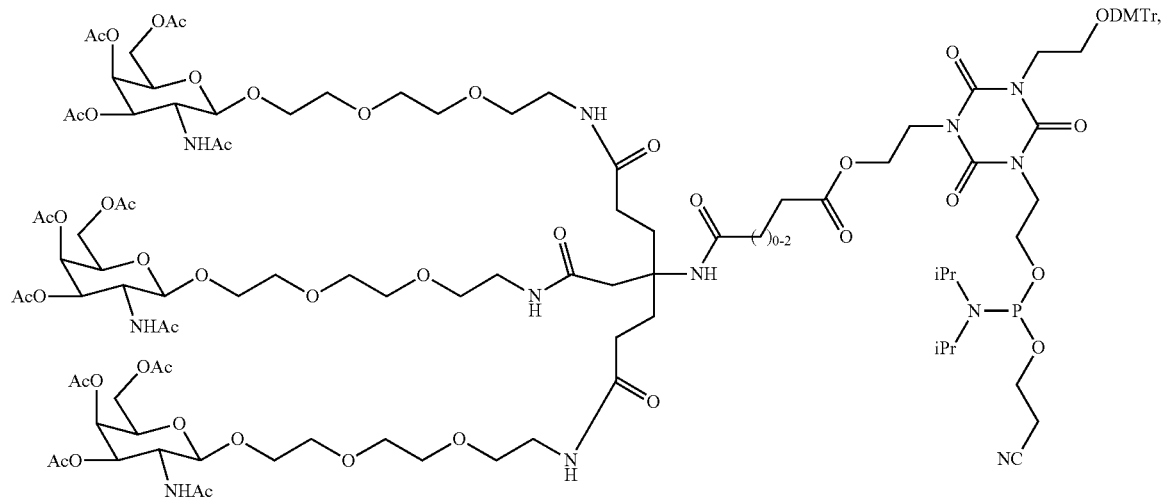
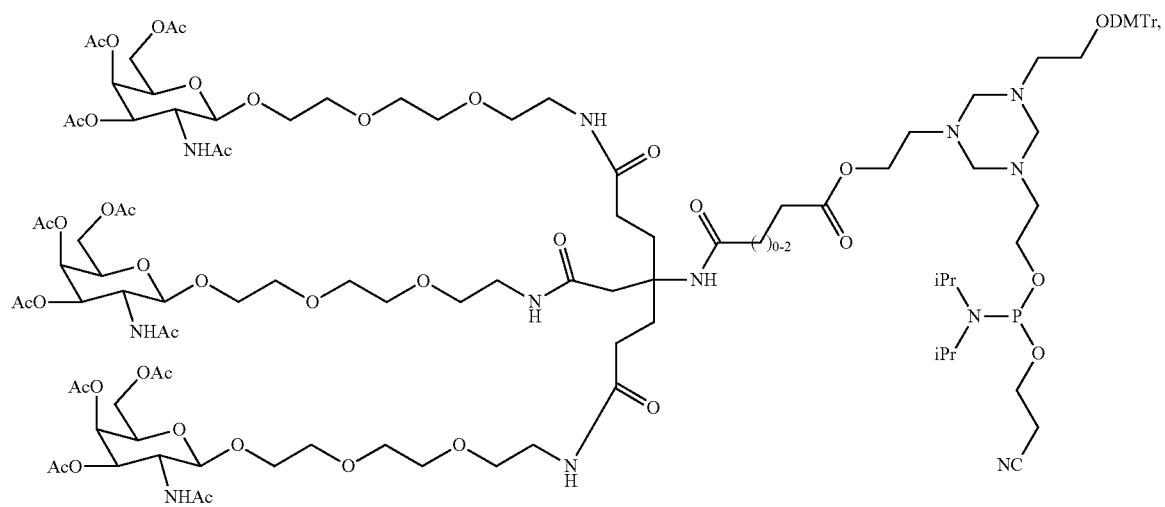
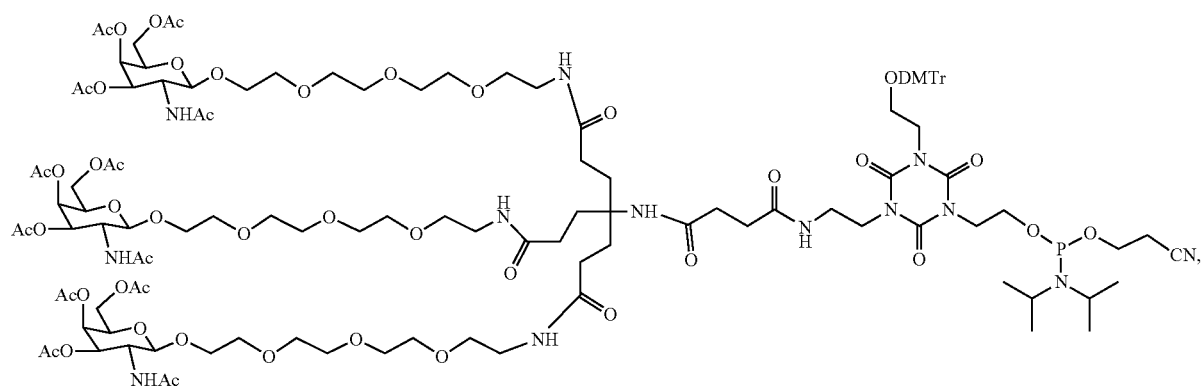

-continued
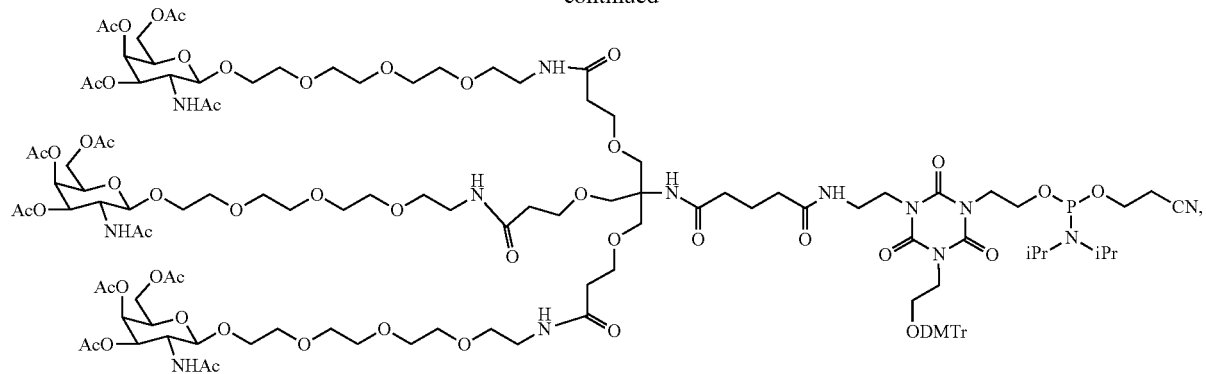
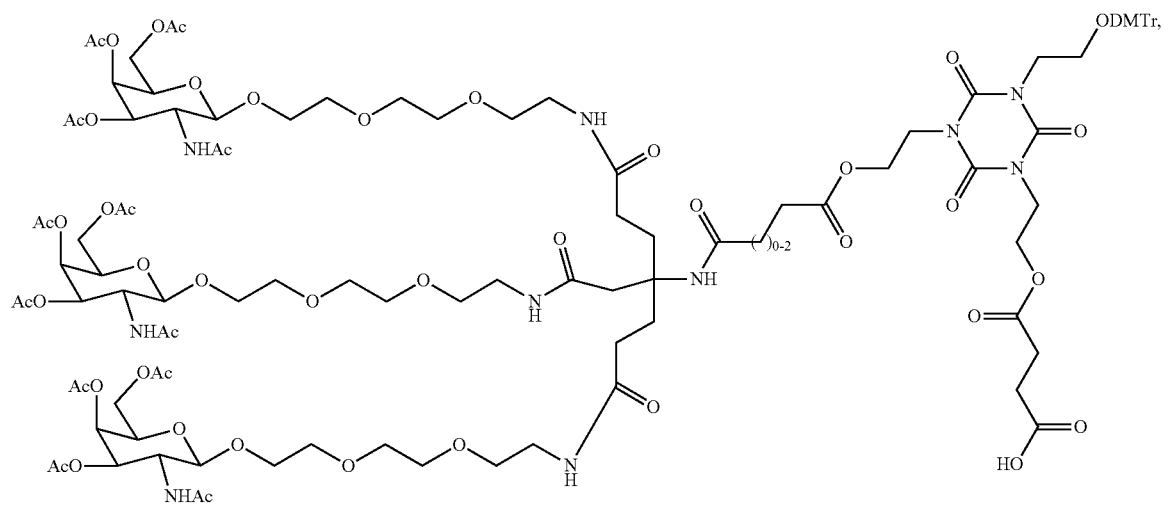
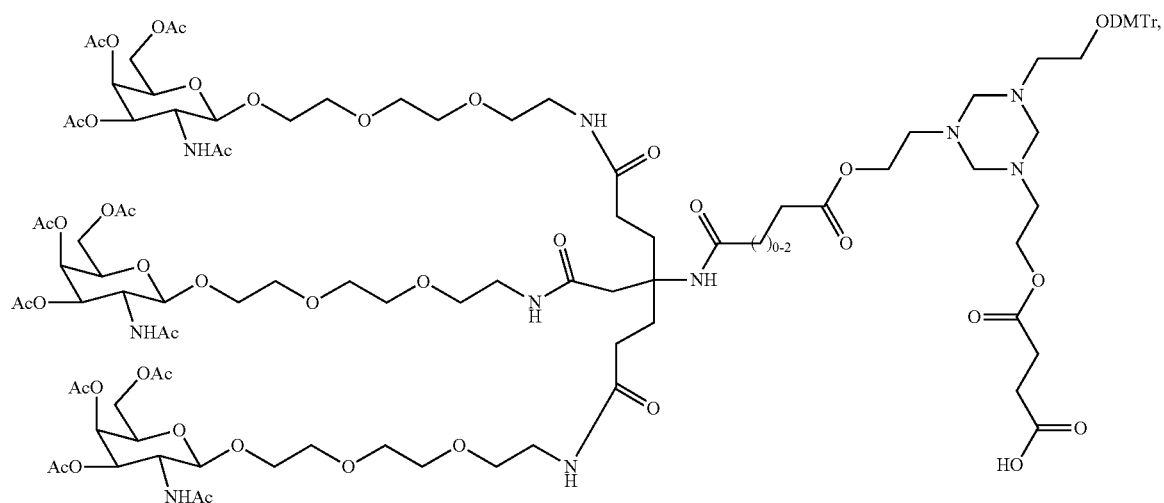

-continued

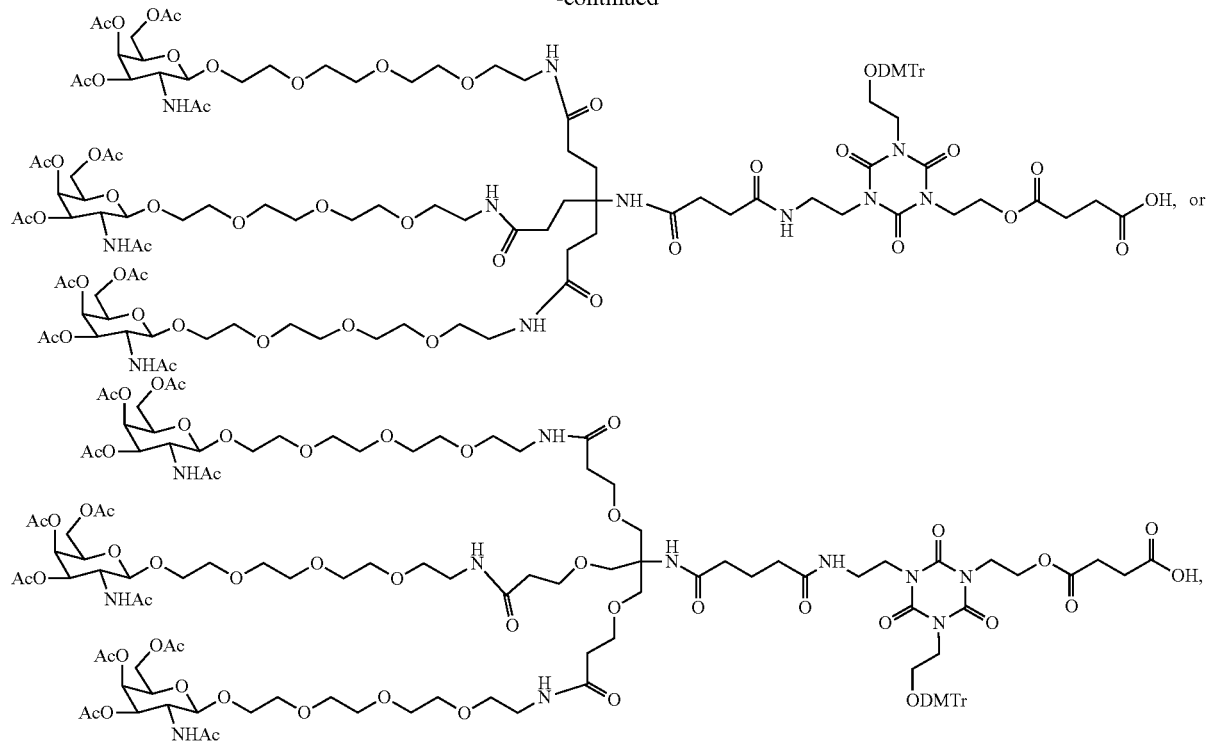

or a pharmaceutically acceptable salt thereof.

In any embodiments of the compounds described herein, when $R^6$ comprises a succinate moiety (—C(O)CH$_2$CH$_2$C(O)OH), the compound may be attached to a solid support through the succinate moiety, optionally via a linker.

In any embodiments of the compounds described herein, when $R^6$ comprises a phosphoramidite moiety such as

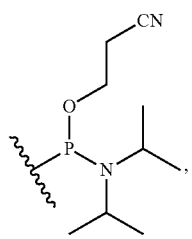 [SMILES: *P(OCCC#N)N(C(C)C)C(C)C]

the compound may be used to react with 5'-OH of another nucleoside or the 5'-OH terminal of an oligonucleotide. Additional embodiments include oligonucleotides prepared by the reaction described herein.

Solid Support Conjugated with GalNAc Compounds

Some embodiments of the present application relate to a solid support comprising the compound of Formula (I) (including (Ia)-(Ic) and (Id-1)-(Id-8)), or Formula (II) (including (IIa)-(IId) and (IIe-1)-(IIe-8)) as described herein covalently attached thereto, for example, via $R^6$ of the compound. In one embodiment, $R^6$ is —C(=O)CH$_2$CH$_2$(=O)OH. In another embodiment, $R^6$ is —C(=O)CH$_2$CH$_2$C(=O)NH$_2$. In further embodiments, the compound is covalently attached to the solid support via a moiety

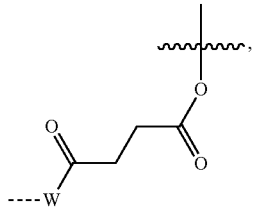

wherein W is O or NH; wherein the dashed line refers to the connection with the solid support, optionally through an additional linker, and the squiggly line refers to the point of the attachment of the oxygen atom (that is covalently attached to $R^6$ of the compound) to the remaining portion of the compound. In further embodiments, the solid support bounded nucleoside may serve as a starting point for solid phase oligo synthesis, through —OR$^5$ functionality of the compound after deprotection to expose the free hydroxy group. In non-limiting embodiments, the solid support may comprise controlled pore glass (CPG) or macroporous polystyrene (MPPS), or SiO$_2$ particles.

Functionalized GalNAc Analogs in Oligonucleotide Synthesis

Some embodiments of the present application relate to a method for preparing a synthetic oligonucleotide, comprising reacting a compound described herein, with an oligonucleotide. In some embodiments, the oligonucleotide comprises 1 to 100 base length, 5 to 50 base length, or 10 to 30 base length. In further embodiments, the reaction is conducted on a solid support.

Step 1: De-Blocking (Detritylation)

The DMTr group is removed with a solution of an acid, such as 2% trichloroacetic acid (TCA) or 3% dichloroacetic acid (DCA), in an inert solvent (dichloromethane or toluene). The orange-colored DMTr cation formed is washed out; the step results in the solid support-bound oligonucleotide precursor bearing a free 5'-terminal hydroxyl group.

Step 2: Coupling

A 0.02-0.2M solution of nucleoside phosphoramidite (or a mixture of several phosphoramidites) in acetonitrile is activated by a 0.2-0.7 M solution of an acidic azole catalyst, 1H-tetrazole, 5-ethylthio-1H-tetrazole, 2-benzylthiotetrazole, 4,5-dicyanoimidazole, or a number of similar compounds. The mixing is usually very brief and occurs in fluid lines of oligonucleotide synthesizers (see below) while the components are being delivered to the reactors containing solid support. The activated phosphoramidite in 1.5-20-fold excess over the support-bound material is then brought in contact with the starting solid support (first coupling) or a support-bound oligonucleotide precursor (following couplings) whose 5'-hydroxy group reacts with the activated phosphoramidite moiety of the incoming nucleoside phosphoramidite to form a phosphite triester linkage. The reaction is also highly sensitive to the presence of water, particularly when dilute solutions of phosphoramidites are used, and is commonly carried out in anhydrous acetonitrile. Upon the completion of the coupling, any unbound reagents and by-products are removed by washing.

Step 3: Capping

The capping step is performed by treating the solid support-bound material with a mixture of acetic anhydride and 1-methylimidazole or, less often, DMAP as catalysts and, in the phosphoramidite method, serves two purposes. After the completion of the coupling reaction, a small percentage of the solid support-bound 5'-OH groups (0.1 to 1%) remains unreacted and needs to be permanently blocked from further chain elongation to prevent the formation of oligonucleotides with an internal base deletion commonly referred to as (n-1) shortmers. The unreacted 5'-hydroxy groups are, to a large extent, acetylated by the capping mixture.

Step 4: Oxidation

The newly formed tricoordinated phosphite triester linkage is not natural and is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. Oxidation may be carried out under anhydrous conditions using tert-Butyl hydroperoxide or (1S)-(+)-(10-camphorsulfonyl)-oxaziridine (CSO). The step of oxidation may be substituted with a sulfurization step to obtain oligonucleotide phosphorothioates. In the latter case, the sulfurization step is best carried out prior to capping.

In solid-phase synthesis, an oligonucleotide being assembled is covalently bound, via its 3'-terminal hydroxy group, to a solid support material and remains attached to it over the entire course of the chain assembly. The solid support is contained in columns whose dimensions depend on the scale of synthesis and may vary between 0.05 mL and several liters. At the end of the chain assembly, the oligonucleotide is released from the solid support and is eluted from the column or the well. The two most often used solid-phase materials are controlled pore glass (CPG) and macroporous polystyrene (MPPS).

In contrast to organic solid-phase synthesis and peptide synthesis, the synthesis of oligonucleotides proceeds best on non-swellable or low-swellable solid supports. The two most often used solid-phase materials are controlled pore glass (CPG) and macroporous polystyrene (MPPS).

CPG is commonly defined by its pore size. In oligonucleotide chemistry, pore sizes of 500, 1000, 1500, 2000, and 3000 Å are used to allow the preparation of about 50, 80, 100, 150, and 200-mer oligonucleotides, respectively. To make native CPG suitable for further processing, the surface of the material is treated with (3-aminopropyl)triethoxysilane to give aminopropyl CPG. The aminopropyl arm may be further extended to result in long chain aminoalkyl (LCAA) CPG. The amino group is then used as an anchoring point for linkers suitable for oligonucleotide synthesis.

MPPS suitable for oligonucleotide synthesis is a low-swellable, highly cross-linked polystyrene obtained by polymerization of divinylbenzene, styrene, and 4-chloromethylstyrene in the presence of a porogeneous agent. The macroporous chloromethyl MPPS obtained is converted to aminomethyl MPPS.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

Example 1. General Procedure for the Preparation of Monovalent GalNAc Analogs

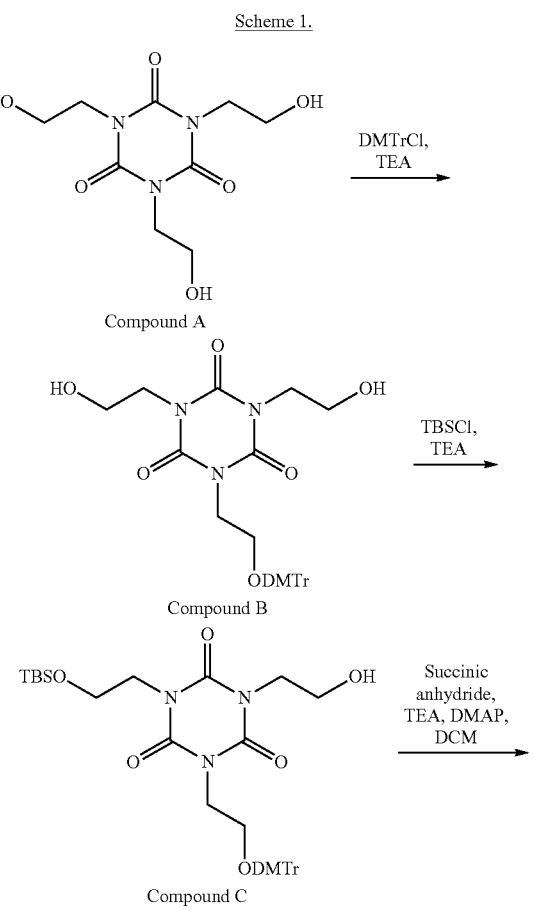

65

-continued

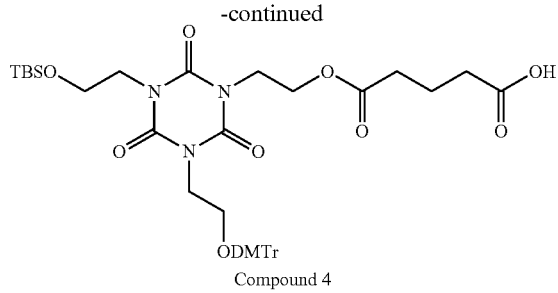
Compound 4

To a solution of 1,3,5-tris(2-hydroxyethyl)-1,3,5-triazinane-2,4,6-trione (26.1 g, 100 mmol) in pyridine (200 mL) was added 4,4'-Dimethoxytriphenylmethyl chloride (33.8 g, 100 mmol), and the mixture was stirred at rt for 18 h. The mixture was then concentrated in vacuo. The residue was purified by column chromatography eluting with DCM/MeOH (0-20% MeOH in DCM) to give Compound B (21.3 g, 38%) as a colorless oil. MS: found: [M+Na]$^+$=586.3; calc: [M+Na]$^+$=586.6.

Step 2: Compound B is dissolved in solvent and TEA is added followed by addition of TBSCL. Completion of the reaction is confirmed and the reaction mixture is purified to obtain Compound C.

66

Step 3: Compound C is dissolved in DCM and TEA is added followed by addition of DMAP and succinic anhydride to obtain Compound 4.

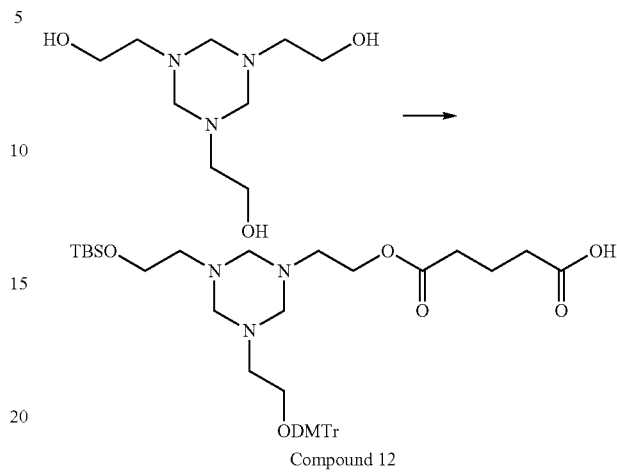
Compound 12

Compound 12 can be prepared following similar procedures described above for the preparation of Compound 4.

Scheme 2.

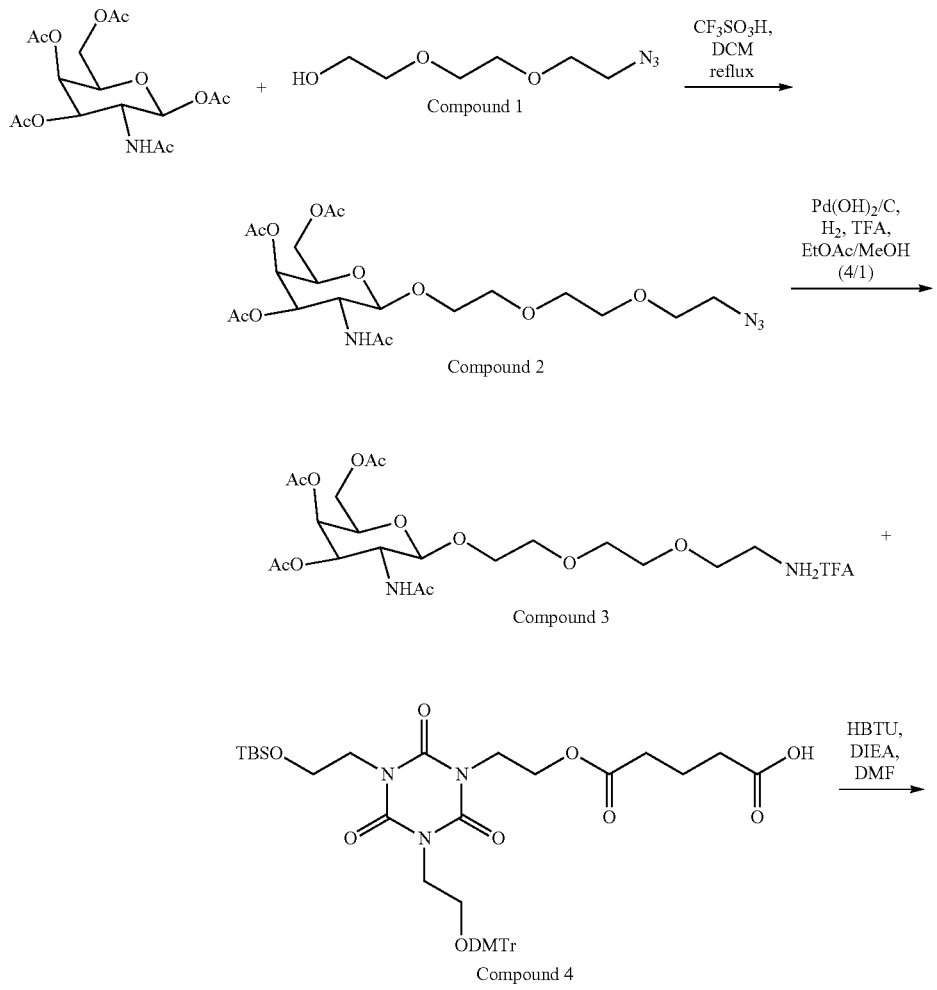

-continued

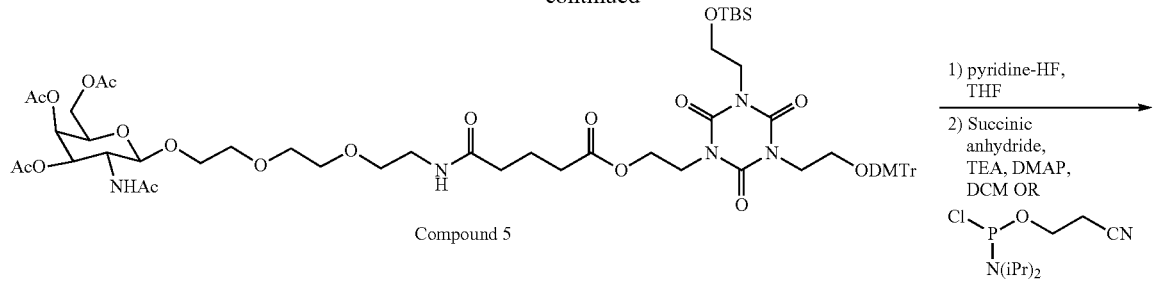
Compound 5

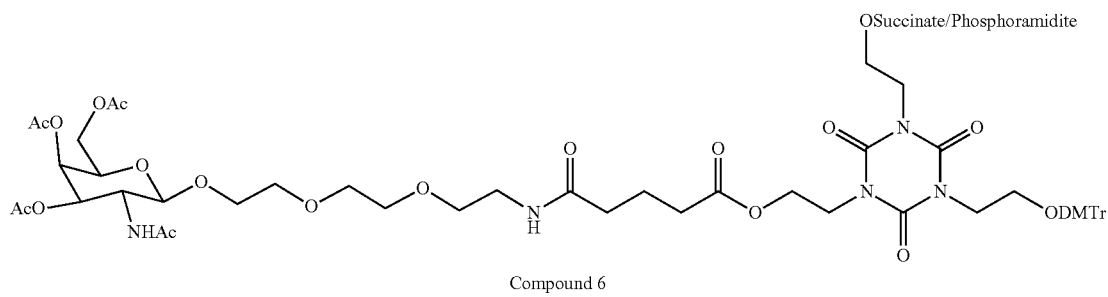
Compound 6

Step 1: GalNAc (10 g, 25.7 mmol) and Compound 1 (15.4 g, 102.7 mmol) were dissolved in DCM (100 mL) and CF$_3$SO$_3$H (0.34 mL, 3.85 mmol) was then added. The reaction mixture was refluxed under argon overnight and then cooled down to rt. This mixture was then poured into 1 M NaHCO$_3$ (51 mL), and the organic layer was separated, washed with water, brine and dried over Na$_2$SO$_4$. After filtration, the organic layer was concentrated to dryness under vacuum. The crude product was purified by column purification using hexanes/ethyl acetate (1/1) to DCM/MeOH (2% to 8% MeOH). The pure fractions were collected and concentrated to dryness under vacuum to obtain Compound 2 in quantitative yields. MS: found: [M+H]= 505.7; calc: [M+H]=505.2.

Step 2: Compound 2 (0.224 g, 0.44 mmol) is in THF (3 mL) and Pd/C (22 mg, 10 wt %) was added. The reaction mixture was flushed with H$_2$ for one minute and the flask is sealed with septum. A balloon filled with hydrogen was inserted to the flask, and it was allowed to stir at rt for 3 h and filtered through celite pad. The pad was washed with ethyl acetate and the combined organic phase was concentrated to dryness under vacuum to Compound 3 in quantitative yields. MS: found: [M+H]=479.6; calc: [M+H]= 479.2. Compound 3 may be without further purification.

Step 3: Compound 3 (0.44 mmol) from above is dissolved in DMF (2.2 mL) and DIEA (0.77 mL, 4.4 mmol) is then added. The mixture is stirred under argon until dissolved. Compound 4 (0.19 g, 0.44 mmol) is added followed by HBTU (0.19 g, 0.49 mmol). The reaction mixture is stirred at r.t overnight and is diluted with EtOAc (20 mL). This mixture is extracted with saturated NaHCO$_3$ (20 mL), brine (20 mL), and the organic phase is dried over Na$_2$SO$_4$. After filtration the solution is concentrated to dryness to afford crude Compound 5.

Step 4: Compound 5 is deprotected with pyridine-HF to remove the TBS group and provide the primary alcohol that is converted to Compound 6 by reacting the unprotected hydroxy group with succinic anhydride or

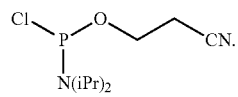

Example 2. General Procedure for the Preparation of Trivalent GalNAc Analogs

Scheme 3.

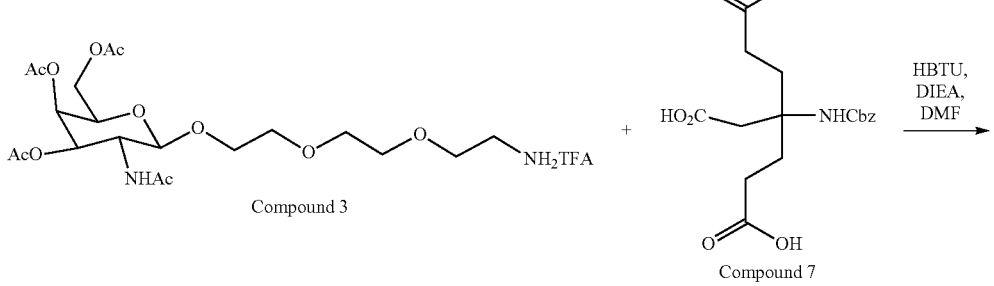

-continued
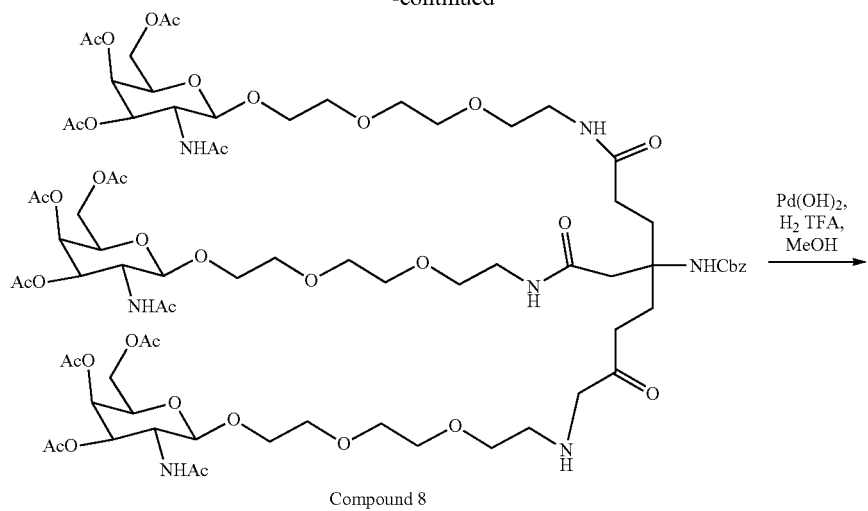
Compound 8
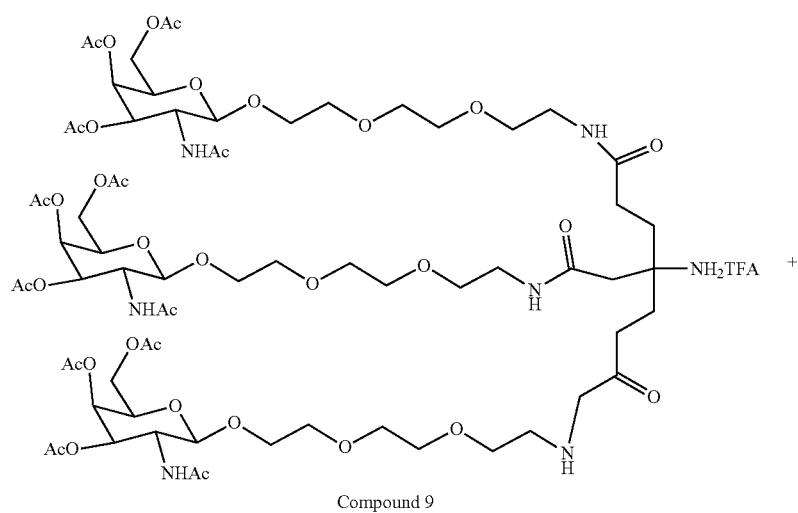
Compound 9
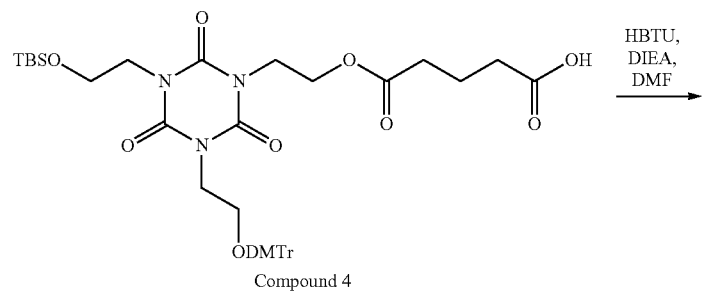
Compound 4

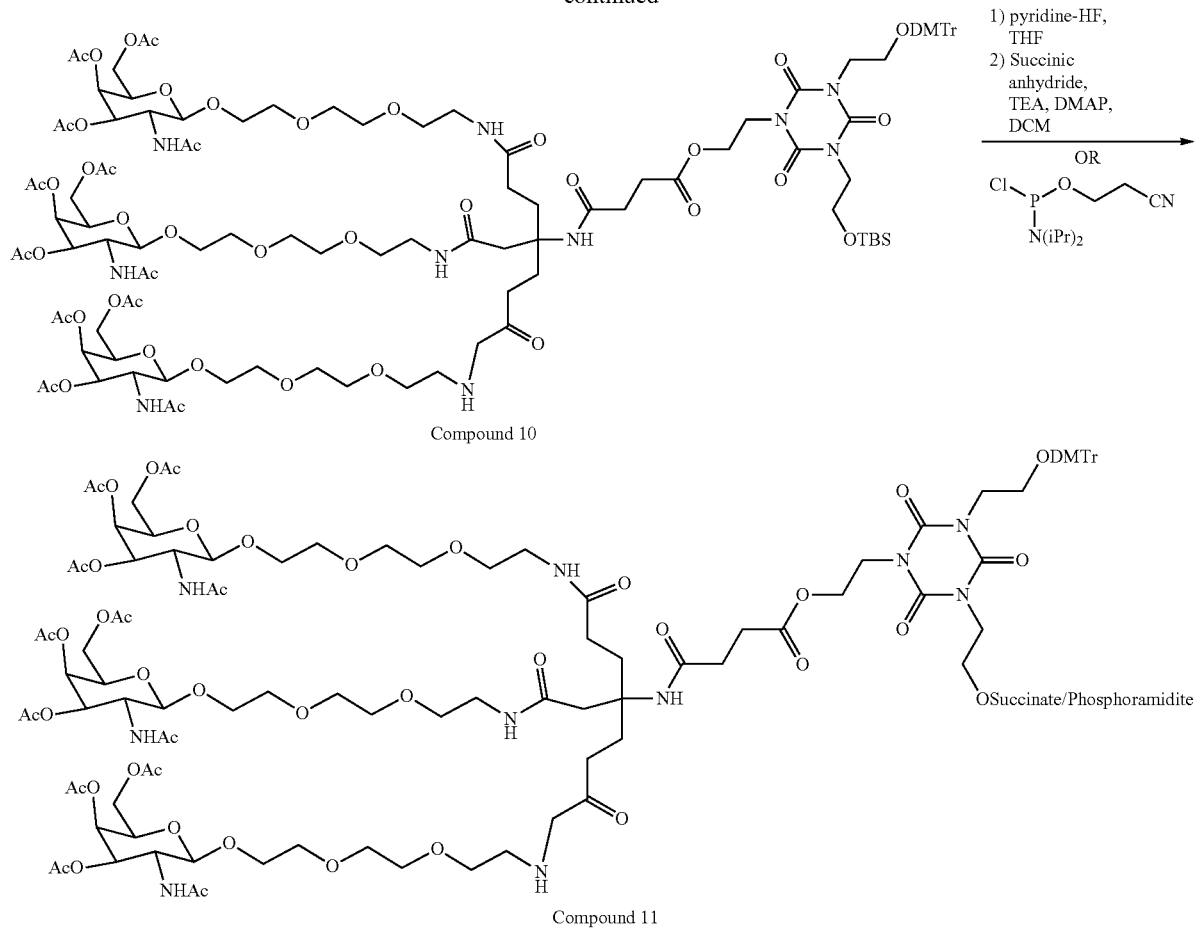

Step 1: Compound 3 is dissolved in DMF then HBTU and DIEA are added followed by addition of Compound 7. Completion of the reaction is confirmed and the reaction mixture is purified to obtain Compound 8.

Step 2: Compound 8 is dissolved in MeOH and TFA then Pd(OH)$_2$ is added and the reaction mixture is hydrogenated. Completion of the reaction is confirmed and the reaction mixture is purified to obtain Compound 9.

Step 3: Compound 9 is dissolved in DMF then HBTU and DIEA are added followed by addition of Compound 4. Completion of the reaction is confirmed and the reaction mixture is purified to obtain Compound 10.

Step 4: Compound 10 is deprotected with pyridine-HF to remove the TBS group and provide the unprotected hydroxy group that is converted to Compound 11 by reacting the primary alcohol with succinic anhydride or

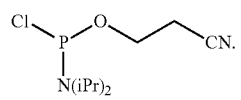

Example 3. General Procedure for the Preparation of Monovalent GalNAc Analogs

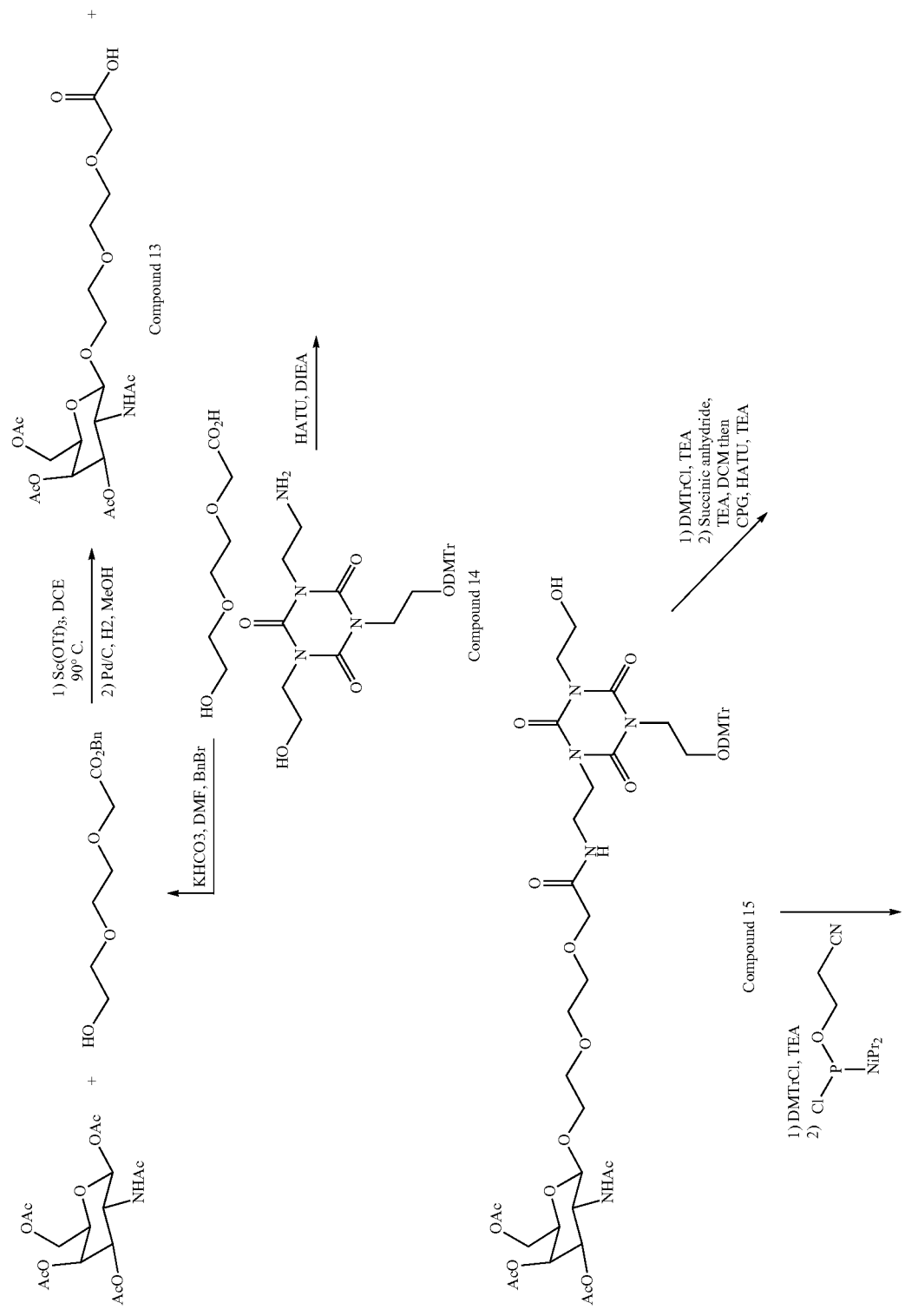

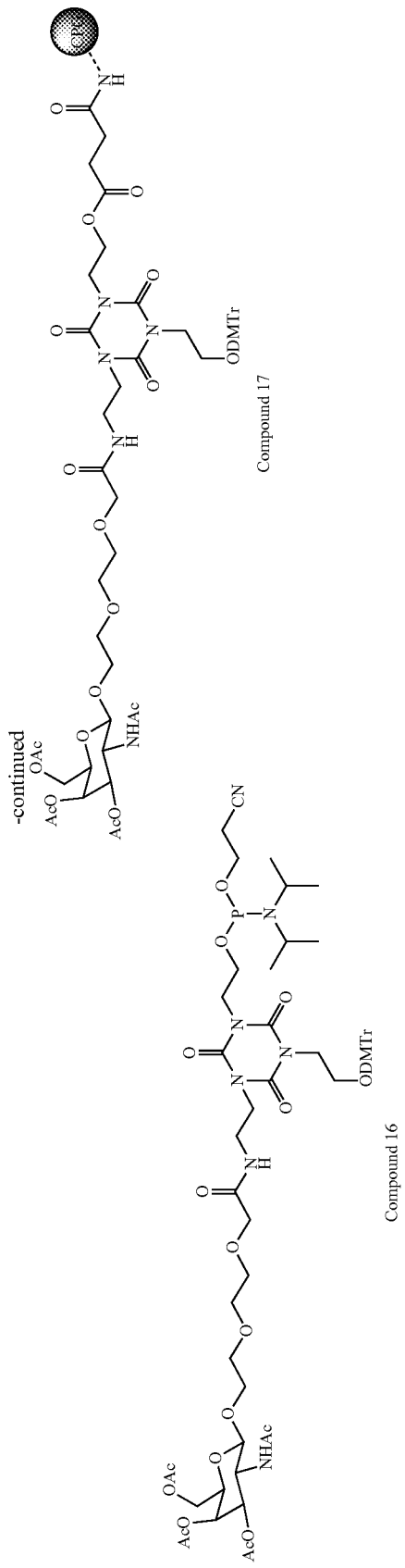
Compound 17
Compound 16
-continued

Compound 13: Step 1: HO-PEG2-CH$_2$CO$_2$H (5.0 g, 30.5 mmol) and KHCO$_3$ (3.65 g, 36.5 mmol) were dissolved in DMF (61.0 mL) in around bottom flask with stirring. Benzyl bromide (4.35 mL, 36.5 mmol) was added dropwise, and the reaction mixture was allowed to stir at room temperature overnight. Volatile was removed in vacuo, and the residual was dissolved in DCM. Precipitates were removed by filtration, and the filtrate was concentrated. The crude material was purified by silica column (eluent: 0-15% MeOH in DCM). Pure fractions were collected and concentrated to dryness under vacuum to obtain an oil (4.02 g, 51.9% yield). MS: found: [M+H]=255.4; calc: [M+H]=255.1.

Step 2: The above oil (4.02 g, 15.8 mmol) and peracylated GalNAc (4.10 g, 10.5 mmol) were dissolved in DCE (40.4 mL). Sc(OTf)$_3$ (0.36 g, 0.74 mmol) was then added. The reaction mixture was heated to 90° C. overnight. The reaction mixture was cooled to room temperature and poured into saturated NaHCO$_3$ (50 mL) with vigorous stirring. The organic layer was separated and the aqueous phase was extracted with DCM (2×50 mL). The combined organic phase was dried over Na$_2$SO$_4$, filtered, and concentrated to dryness. The crude material was purified by normal phase silica column (eluent: 0 to 10% MeOH in DCM). Fractions were collected and concentrated to dryness under vacuum to obtain yellow oil (7.23 g, 118% yield). MS: found: [M+H]= 584.4; calc: [M+H]=584.2.

Step 3: The product from step 2 was dissolved in MeOH (62 mL), and 10% Pd/C (200 mg, 1.86 mmol) under Ar purge. Air was removed under vacuum and H$_2$ balloon was inserted. The reaction mixture was stirred at r.t for 2 h and was filtered through a celite pad. The pad was washed the Compound 16: In a 50 mL RB flask Compound 15 (370 mg, 0.356 mmol) was dissolved in DCM (20 mL). 2-Cyanoethyl N,N-diisopropylchlorophosphoramindite (126 mg, 0.535 mmol) and DIEA (138 mg, 1.07 mmol) were added. The reaction mixture was stirred at room temperature for 2 hours. Completion of the reaction was confirmed by TLC. This mixture was then poured into saturated NaHCO$_3$ (10 mL) and DCM (20 mL) was added. The organic layer was separated, washed with water (30 mL) and brine (30 mL). The organic layer was then dried over Na$_2$SO$_4$. After filtration, the organic layer was concentrated to dryness under vacuum. The crude product was then purified by column purification using DCM/TEA (0% to 10% TEA). The pure fractions were collected and concentrated to dryness under vacuum to obtain Compound 16 (248 mg, 56%). MS: found: [M+NH$_4$]=1255.4; calc: [M+NH$_4$]=1255.5. $^{31}$P-NMR (mixture of diastereomers, DMSO-d$_6$): δ 147.343.

Compound 17: Step 1: In a 100 mL RB flask Compound 15 (406 mg, 0.392 mmol) was dissolved in DCM (20 mL). Succinic anhydride (47 mg, 0.497 mmol) and TEA (118 mg, 1.175 mmol) were added. The reaction mixture was stirred at room temperature for 12 hours. Completion of the reaction was confirmed by TLC. This mixture was then poured into saturated NaHCO$_3$ (40 mL), and DCM (50 mL) was added. The organic layer was separated, washed with water (30 mL) and brine (30 mL) The organic layer was then dried over Na$_2$SO$_4$, filtered, and concentrated to dryness under vacuum. The crude product was purified by column purification using DCM/MeOH (0 to 10% MeOH). The pure fractions were collected and concentrated to dryness under vacuum to obtain the corresponding succinate

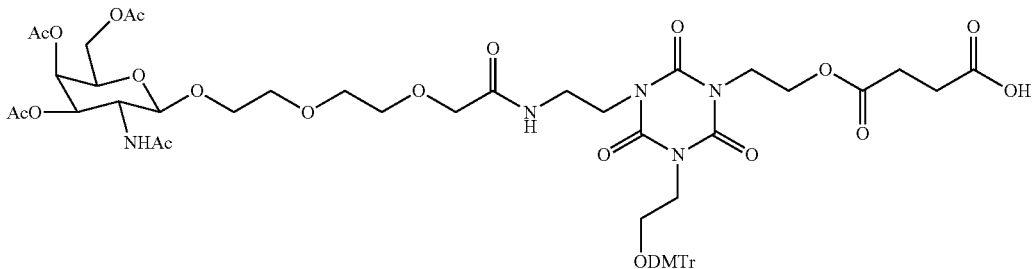

with MeOH twice, and the volatile was removed in vacuo. The crude material was purified by C18 reversed phase column (eluent: 0-90% MeCN in water). The pure fractions were collected and concentrated to dryness under vacuum to obtain Compound 13 as an oil (3.72 g, 71.8% yield). MS: found: [M−H]=492.4; calc: [M−H]=492.2.

Compound 15: Compound 13 (850 mg, 1.724 mmol) was dissolved in DCM (50.0 mL) under argon, and HATU (1.310 mg, 3.448 mmol) followed by DIEA (889 mg, 6.896 mmol). Compound 14 (1.065 g, 1.89 mmol) was then added. The reaction mixture was stirred at room temperature for 12 h and was diluted with dichloromethane (50 mL). Brine (40 mL) was then added to the mixture, and the organic phase was separated. The aqueous phase was extracted with dichloromethane (20 mL×2), and the combined organic phase was dried over Na$_2$SO$_4$, filtered, and concentrated to dryness to obtain yellow solid. The crude product was purified by column purification using DCM/MeOH (0 to 10% MeOH). The pure fractions were collected and concentrated to dryness under vacuum to obtain Compound 15 (865 mg, 48%). MS: found: [M+NH$_4$]=1055.7; calc: [M+NH$_4$]=1055.4.

(128 mg, 29%). MS: found: [M+NH$_4$]=1155.7; calc: [M+NH$_4$]=1155.4.

Step 2: In a 50 mL RB flask succinate from step 1 (41 mg, 0.036 mmol) was dissolved in MeCN (5 mL). HATU (13.7 mg, 0.036 mmol) and DIEA (14 mg, 0.108 mmol) were added. After 5 min, LCAA CPG (1000 Å, 0.5 g) was then added. The reaction mixture was stirred at room temperature for 3 hours. After filtration, this CPG was washed with MeCN (50 mL×3) and THF (50 mL×3), and then dried under vacuum. Cap A reagent: (THF/acetic anhydride/pyridine 80/10/10 v/v/v, 1.25 mL). and Cap B reagent: (1-methylimidazole/THF, 16/84, v/v, 1.25 mL) were added into the flask, and the mixture was stirred at room temperature for 2 hours. After filtration, the capped CPG was washed with EtOH (50 mL×3), EtOH/10% Pyridine (50 mL×3), THF (50 mL×3) and DCM (50 mL×3). This capped CPG Compound 17 was then dried under vacuum. Loading was determined by standard DMTr assay by UV-Vis (498 nm) to be 41 µmol/g.

Example 4. General Procedure for the Preparation of Trivalent GalNAc Analogs

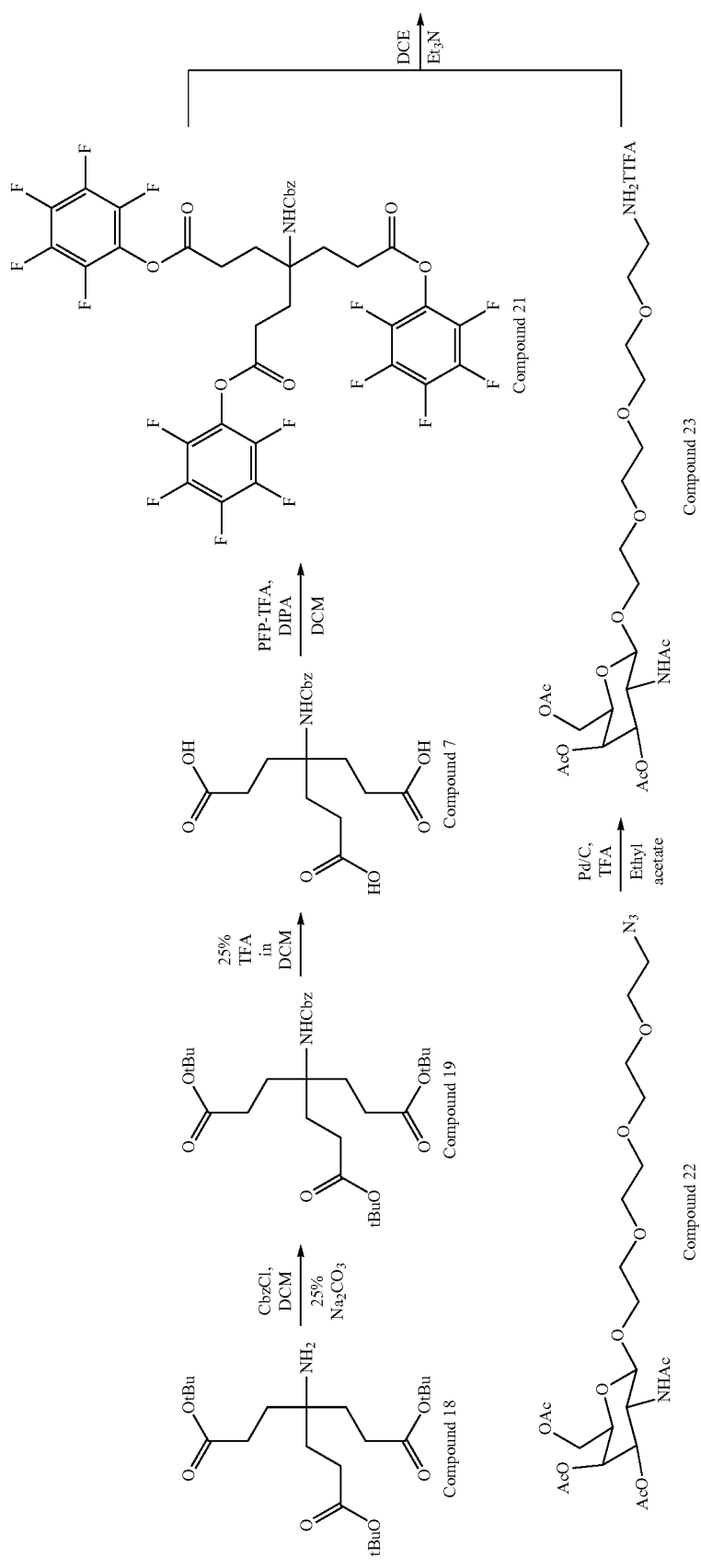

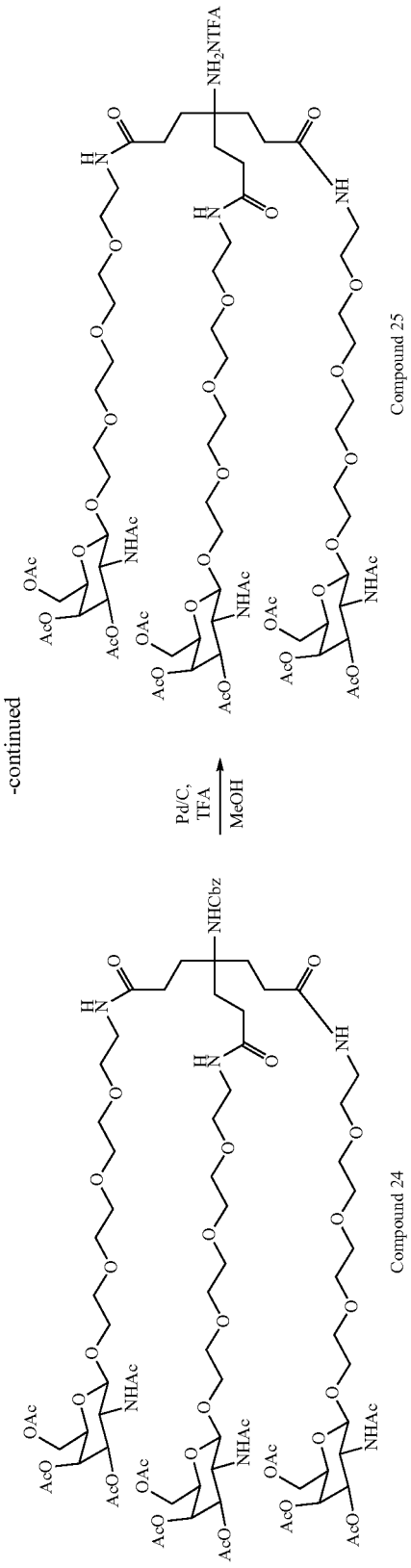
Compound 24
Pd/C, TFA / MeOH
Compound 25

Synthesis of Compound 7: To a solution of Compound 18 (4.46 g, 10.7 mmol) in DCM and 25% aq. $Na_2CO_3$ (50 mL/50 mL) was added CbzCl (5.49 g, 32.1 mmol), and the resulting reaction mixture was stirred at rt for 43 h. TLC indicated completion of the reaction. The mixture was diluted with $H_2O$/DCM (25 mL/25 mL), the aqueous layer was then extracted with DCM (20 mL×2), and the organic phase was washed with $H_2O$/brine (25 mL/25 mL). The combined organic layers were dried over $Na_2SO_4$, filtered and concentrated to give crude Compound 19 (6.0 g) as a white solid and was used without further purification.

Compound 19 (6.0 g, 10.7 mmol) was dissolved in 25% TFA in DCM (60 mL) at rt, the reaction mixture was stirred for 2 h at rt. TLC indicated completion of the reaction. The mixture was concentrated in vacuo, and the residue was recrystallized by EA/Hexane (10 mL/30 mL). Compound 7 (3.62 g, 89% for 2 steps) was obtained as a white solid. MS: found: $[M-H]^-=380.5$; calc: $[M-H]^-=380.4$.

Synthesis of Compound 21: To a solution of Compound 3 (3.62 g, 9.49 mmol) in anhydrous DCM (45 mL) was added pentafluorophenyl trifluoroacetate (13.3 g, 47.4 mmol) and DIPEA (19.8 mL, 113.9 mmol). The reaction mixture was stirred for 2 h at rt. TLC indicated completion of the reaction. The mixture was diluted with $H_2O$/DCM (25 mL/50 mL). The aqueous layer was extracted with DCM (25 mL×2). The combined organic layers were dried over $Na_2SO_4$, filtered and concentrated. The residue was purified by column chromatography (eluting with 0-20% Ethyl acetate in Hexane to provide the Compound 21 (4.46 g, 53%) as a colorless oil. MS: found: $[M+NH_4]^+=897.3$; calc: $[M+NH_4]^+=897.5$.

Synthesis of Compound 23: To a solution of Compound 22 (23 g, 41.9 mmol) in Ethyl acetate (150 mL) was added trifluoroacetic acid (4.78 g, 41.9 mmol) and Pd/C (2.3 g, 10%) under $N_2$ atmosphere. Then the mixture was exchanged with $H_2$ and stirred for 17 h under $H_2$ atmosphere at rt. TLC indicated completion of the reaction. The mixture was filtered by celite and concentrated to give Compound 23 (18 g, 68%) as a brown foam. MS: found: $[M+H]^+=523.7$; calc: $[M+H]^+=523.6$.

Synthesis of Compound 24: To a solution of Compound 23 (4.34 g, 6.82 mmol) and Compound 21 (1.0 g, 1.14 mmol) in anhydrous DCE (34 mL) was added $Et_3N$ (1.38 g, 13.6 mmol). The reaction mixture was stirred for 21 h at rt. TLC indicated completion of the reaction. The mixture was diluted with $H_2O$/DCM (15 mL/15 mL). The aqueous layer was extracted with DCM (25 mL×2). The combined organic layer was washed by aq. $NaHCO_3$ (15 mL×2) and brine (15 mL×2), dried over $Na_2SO_4$, filtered and concentrated. The residue was purified by column chromatography eluting with DCM/MeOH (0-15% MeOH in DCM) to provide Compound 24 (803 mg, 37%) as a light brown foam. MS: found: $[M+2H/2]^+=948.5$; calc: $[M+2H/2]^+=948.49$.

Synthesis of Compound 25: To a solution of Compound 24 (5.6 g, 3.0 mmol) in MeOH (150 mL) was added trifluoroacetic acid (342 mg, 3.0 mmol) and Pd/C (560 mg, 10%) under $N_2$ atmosphere. The mixture was then exchanged with $H_2$ and stirred for 18 h under $H_2$ atmosphere at rt. TLC indicated completion of the reaction. The mixture was filtered by celite and concentrated to give Compound 25 (5.41 g, 97%) as a brown foam. MS: found: $[M+H]^+=1761.4$; calc: $[M+H]^+=1761.9$.

Example 5. General Procedure for the Preparation of Triazinanes

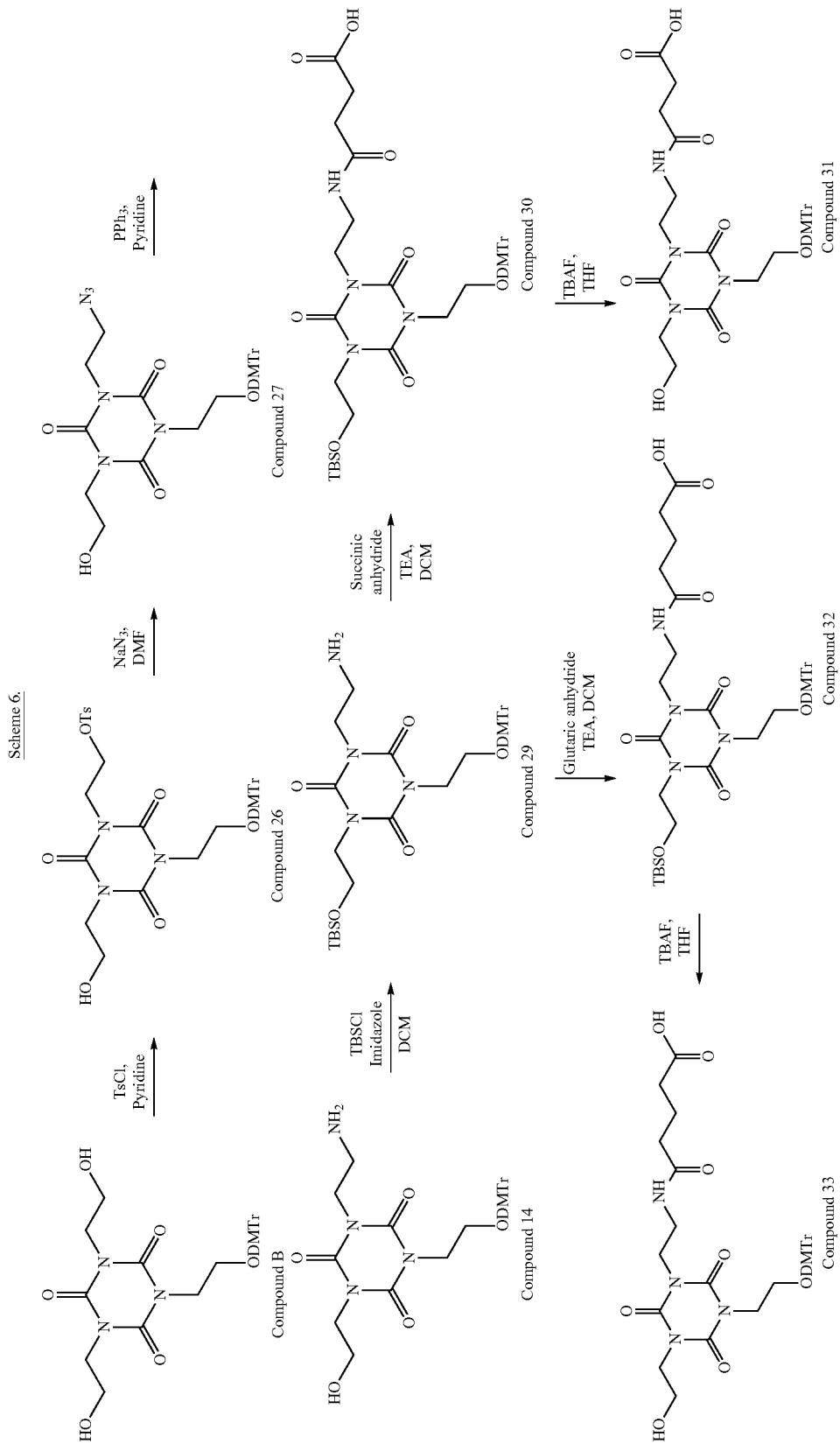

Synthesis of Compound 26: To a solution of Compound B (21.3 g, 38 mmol) in pyridine (100 mL) was added p-toluenesulfonyl chloride (7.2 g, 38 mmol), and the mixture was stirred at rt for 18 h. The mixture was concentrated in vacuo. The residue was purified by column chromatography eluting with DCM/MeOH (0-15% MeOH in DCM) to give Compound 26 (15.8 g, 57%) as a yellow oil. MS: found: $[M+Na]^+$=740.6; calc: $[M+Na]^+$=740.8.

Synthesis of Compound 27: To a solution of Compound 26 (15.8 g, 21.6 mmol) in DMF (200 mL) was added $NaN_3$ (4.2 g, 64.8 mmol), and the mixture was heated to 75° C. and stirred for 6 h. TLC revealed completion of the reaction. The mixture was diluted with $H_2O$/EA (75 mL/75 mL), and the aqueous layer was extracted with EA (50 mL×2). The combined organic layer was washed by $H_2O$ (50 mL×2) and brine (50 mL×2), dried over $Na_2SO_4$, filtered and concentrated. The residue was purified by column chromatography eluting with DCM/MeOH (0-15% MeOH in DCM) to give Compound 27 (6.88 g, 54%) as a white foam. MS: found: $[M2+NH_4]^+$=1194.7; calc: $[M2+NH_4]^+$=1194.5.

Synthesis of Compound 14: To a solution of Compound 27 (6.88 g, 11.7 mmol) in pyridine (100 mL) was added $PPh_3$ (4.6 g, 18 mmol), and the mixture was stirred at rt for 6 h. TLC revealed completion of the reaction, then 30-33% $NH_3$ in $H_2O$ (30 mL) was added. The mixture was stirred for additional 3 h, then the mixture was concentrated. The residue was purified by column chromatography (eluting with 0-10% MeOH in DCM to give Compound 14 (5.10 g, 77%) as a white foam. MS: found: $[M2+H]^+$=1125.8; calc: $[M2+H]^+$=1125.5.

Synthesis of Compound 29: To a solution of Compound 14 (2.0 g, 3.56 mmol) in DCM (40 mL) was added Imidazole (728 mg, 10.7 mmol) and TBSCl (804 mg, 5.36 mmol), and the mixture was stirred at rt for 17 h. TLC revealed completion of the reaction. The mixture was concentrated in vacuo. The residue was purified by column chromatography (eluting with 0-5% MeOH in DCM to give Compound 29 (2.35 g, 98%) as a colorless oil. MS: found: $[2M+H]^+$=1354.0; calc: $[2M+H]^+$=1354.7.

Synthesis of Compound 30: To a solution of Compound 29 (1.2 g, 1.77 mmol) in DCM (35 mL) was added $Et_3N$ (536 mg, 5.31 mmol) and succinic anhydride (230 mg, 2.30 mmol), and the mixture was stirred at rt for 1.5 h. TLC revealed completion of the reaction. The mixture was diluted with $H_2O$/DCM (15 mL/15 mL). The aqueous layer was extracted with DCM (15 mL×2). The combined organic layer was washed by $H_2O$ (10 mL×2) and brine (10 mL×2), dried over $Na_2SO_4$, filtered and concentrated. The residue was purified by column chromatography (eluting with 0-5% MeOH in DCM to give Compound 30 (1.23 g, 89%) as a white foam. MS: found: $[M-H]^-$=775.5; calc: $[M-H]^-$= 775.3.

Synthesis of Compound 31: To a solution of Compound 30 (1.23 g, 1.58 mmol) in THF (35 mL) was added 1.0 M TBAF in THF (1.58 mL, 1.58 mmol), the mixture was stirred at rt for 2.5 h. TLC revealed completion of the reaction. The mixture was concentrated. The residue was purified by column chromatography (eluting with 0-10% MeOH in DCM to give Compound 31 (740 mg, 71%) as a white foam. MS: found: $[M+NH_4]^+$=680.6; calc: $[M+NH_4]^+$= 680.3.

Synthesis of Compound 32: To a solution of Compound 29 (1.2 g, 1.77 mmol) in DCM (35 mL) was added $Et_3N$ (536 mg, 5.31 mmol) and glutaric anhydride (262 mg, 2.30 mmol), and the mixture was stirred at rt for 1.5 h. TLC revealed completion of the reaction. The mixture was diluted with $H_2O$/DCM (15 mL/15 mL). The aqueous layer was extracted with DCM (15 mL×2). The combined organic layer was washed by $H_2O$ (10 mL×2) and brine (10 mL×2), dried over $Na_2SO_4$, filtered and concentrated. The residue was purified by column chromatography (eluting with 0-5% MeOH in DCM to give Compound 32 (1.40 g, 99%) as a white foam. MS: found: $[M+NH_4]^+$=808.9; calc: $[M+NH_4]^+$= 808.4.

Synthesis of Compound 33: To a solution of Compound 32 (1.4 g, 1.76 mmol) in THF (35 mL) was added 1.0 M TBAF in THF (1.76 mL, 1.76 mmol), the mixture was stirred at rt for 2 h. TLC revealed completion of the reaction. The mixture was concentrated. The residue was purified by column chromatography (eluting with 0-10% MeOH in DCM to give Compound 33 (710 mg, 53%) as a white foam. MS: found: $[M+NH_4]^+$=694.6; calc: $[M+NH_4]^+$=694.3.

Example 6. General Procedure for the Preparation of Trivalent GalNAc Analogs
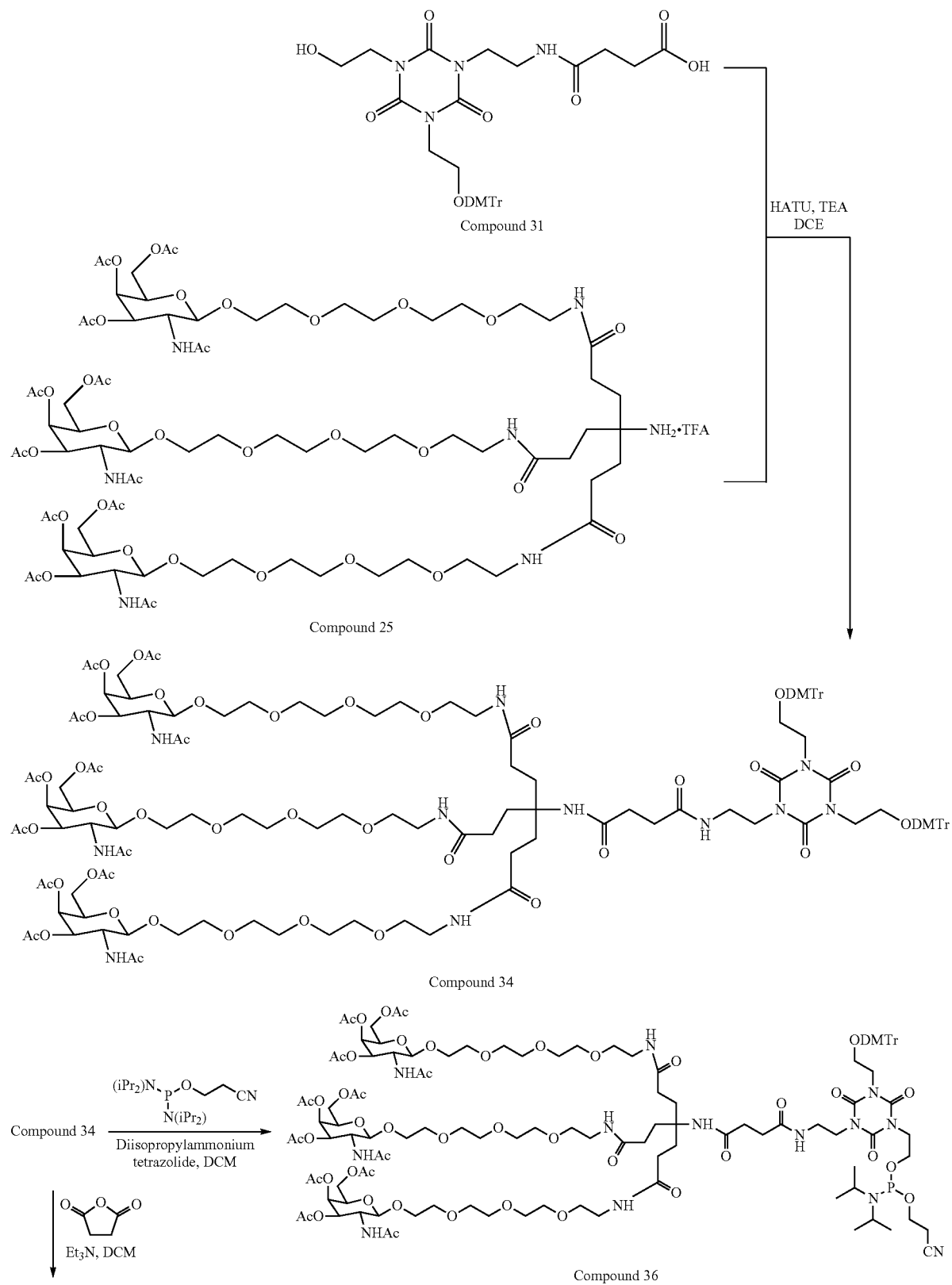

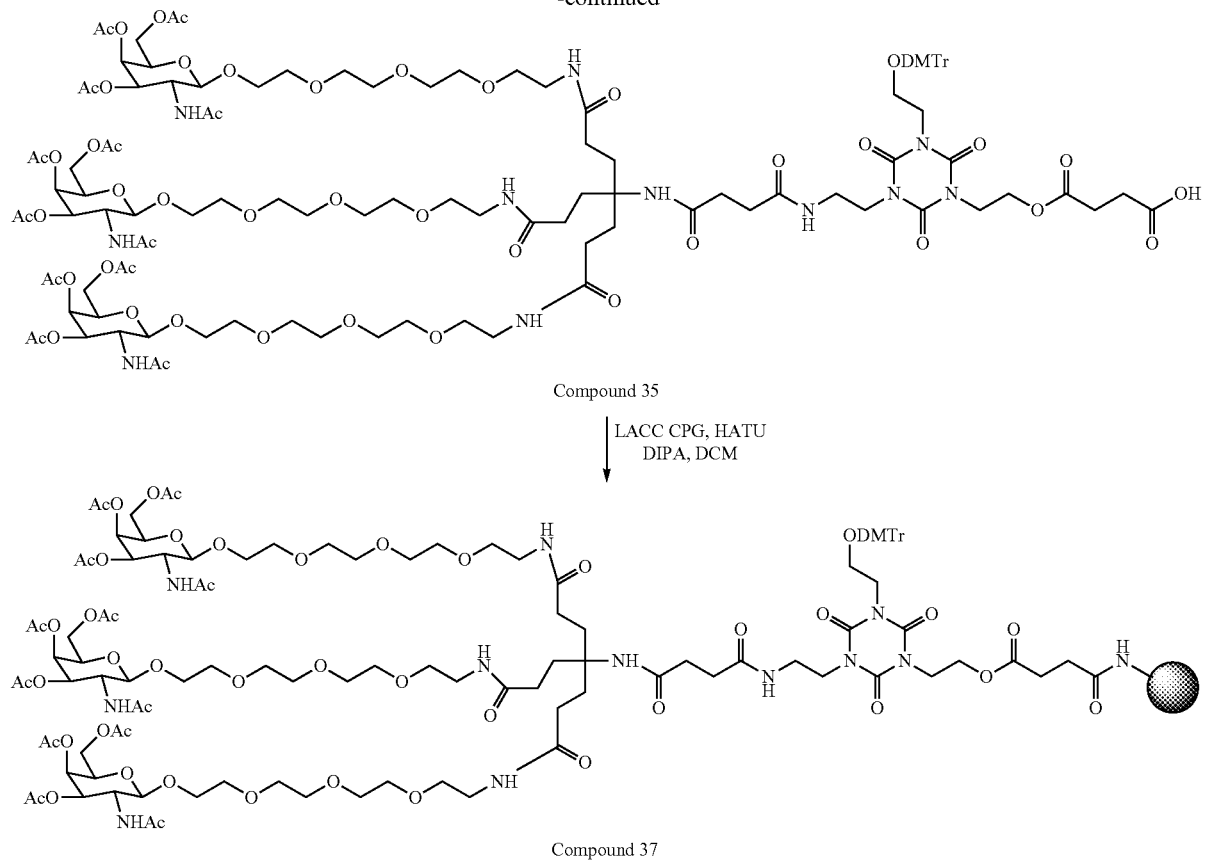

Compound 35

Compound 37

Synthesis of Compound 34: To a solution of Compound 31 (226 mg, 0.34 mmol) and Compound 25 (533 mg, 0.28 mmol) in anhydrous DCE (15 mL) was added Et$_3$N (113 mg, 1.12 mmol) and HATU (213 mg, 0.56 mmol). The reaction mixture was stirred for 71 h at rt. TLC indicated completion of the reaction. The mixture was diluted with H$_2$O/DCM (15 mL/15 mL). The aqueous layer was extracted with DCM (10 mL×2). The combined organic layer was washed by aq. NaHCO$_3$ (10 mL×2) and brine (10 mL×2), dried over Na$_2$SO$_4$, filtered and concentrated. The residue was purified by column chromatography (eluting with 0-15% MeOH in DCM to provide Compound 34 (323 mg, 48%) as a light brown foam. MS: found: $[M+2H/2+NH_4]^{2+}=1221.0$; calc: $[M+2H/2+NH_4]^{2+}=1221.7$.

Synthesis of Compound 35: To a solution of Compound 34 (323 mg, 0.13 mmol) in DCM (13 mL) was added Et$_3$N (60 mg, 0.65 mmol) and succinic anhydride (35 mg, 0.35 mmol), and the mixture was stirred at rt for 17 h. TLC revealed completion of the reaction. The mixture was diluted with H$_2$O/DCM (10 mL/10 mL). The aqueous layer was extracted with DCM (10 mL×2). The combined organic layer was washed by H$_2$O (10 mL×2) and brine (10 mL×2), dried over Na$_2$SO$_4$, filtered and concentrated to give Compound 35 (280 mg, 86%) as a white foam. MS: found: $[M+2H/2+NH_4]^{2+}=1270.8$; calc: $[M+2H/2+NH_4]^{2+}=1271.0$.

Synthesis of Compound 37: To a solution of TriGalNAc succinate Compound 35 (280 mg, 0.105 mmol) in anhydrous acetonitrile (7 mL) was added HATU (40 mg, 0.105 mmol) and DIPEA (41 mg, 0.315 mmol). The mixture was stirred at rt for 10 min. Pretreated LCAA CPG 500Å (1.40 g, loading: 75 μmol/g) was added. The resulting mixture was slowly agitated at 25° C. for 3 h. The mixture was then filtered, the CPG was washed with acetonitrile (7 mL×3) and THF (7 mL×3) successively. The CPG was dried under reduced pressure for 3 h. Loading was determined by standard DMTr assay by UV-Vis (498 nm) to be 48 μmol/g.

To the CPG was added a mixture of Ac$_2$O (0.7 mL) and pyridine (0.7 mL) in anhydrous THF (5.6 mL). The resulting mixture was slowly agitated at 25° C. for 30 min. The mixture was then filtered, and this CPG was washed with THF (7 mL×3), 10% pyridine in MeOH (7 mL×3), MeOH (7 mL×3), acetonitrile (7 mL×2) and DCM (7 mL×1) successively. The capped CPG was dried under reduced pressure for 3 h to give Compound 37 (1.61 g, Loading was determined by standard DMTr assay by UV-Vis (498 nm) to be 49 μmol/g). Ninhydrin test: negative.

Synthesis of Compound 36: To a solution of Compound 34 (728 mg, 0.30 mmol) in anhydrous DCM (15 mL) was added diisopropylammonium tetrazolide (13 mg, 0.075 mmol) and Bis(diisopropylamino)(2-cyanoethoxy)phosphine (181 mg, 0.60 mmol). The reaction mixture was stirred for 21 h at rt. TLC indicated completion of the reaction. The mixture was diluted with aq. NaHCO$_3$/DCM (10 mL/10 mL). The aqueous layer was extracted with DCM (10 mL×2). The combined organic layer was washed by aq. NaHCO$_3$ (10 mL×2), dried over Na$_2$SO$_4$, filtered and concentrated. The residue was dissolved in CH$_3$CN (35 mL) and extracted with Hexane (10 mL×2), the CH$_3$CN phase was concentrated. The residue was purified by column chromatography (eluting with 0-5% MeOH in (1% Et$_3$N in DCM) to provide the TriGalNAc amidite Compound 36 (548 mg, 70%) as a light-yellow foam. MS: found: $[M+2H/2+NH_4]^{2+}=1320.8$; calc: $[M+2H/2+NH_4]^{2+}=1321.1$. $^{31}$PNMR (mixture of diastereomers, broad singlet, DMSO-d$_6$): δ 147.35.

Example 7. General Procedure for the Preparation of Trivalent GalNAc Analogs
Scheme 8.
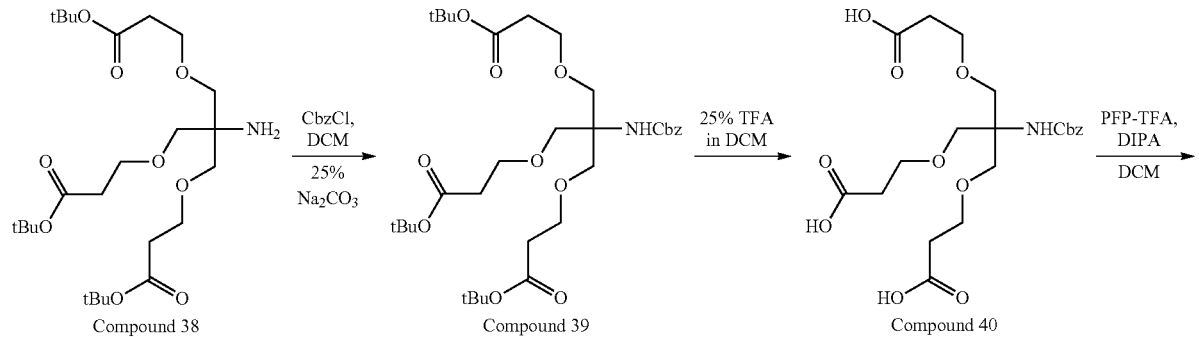
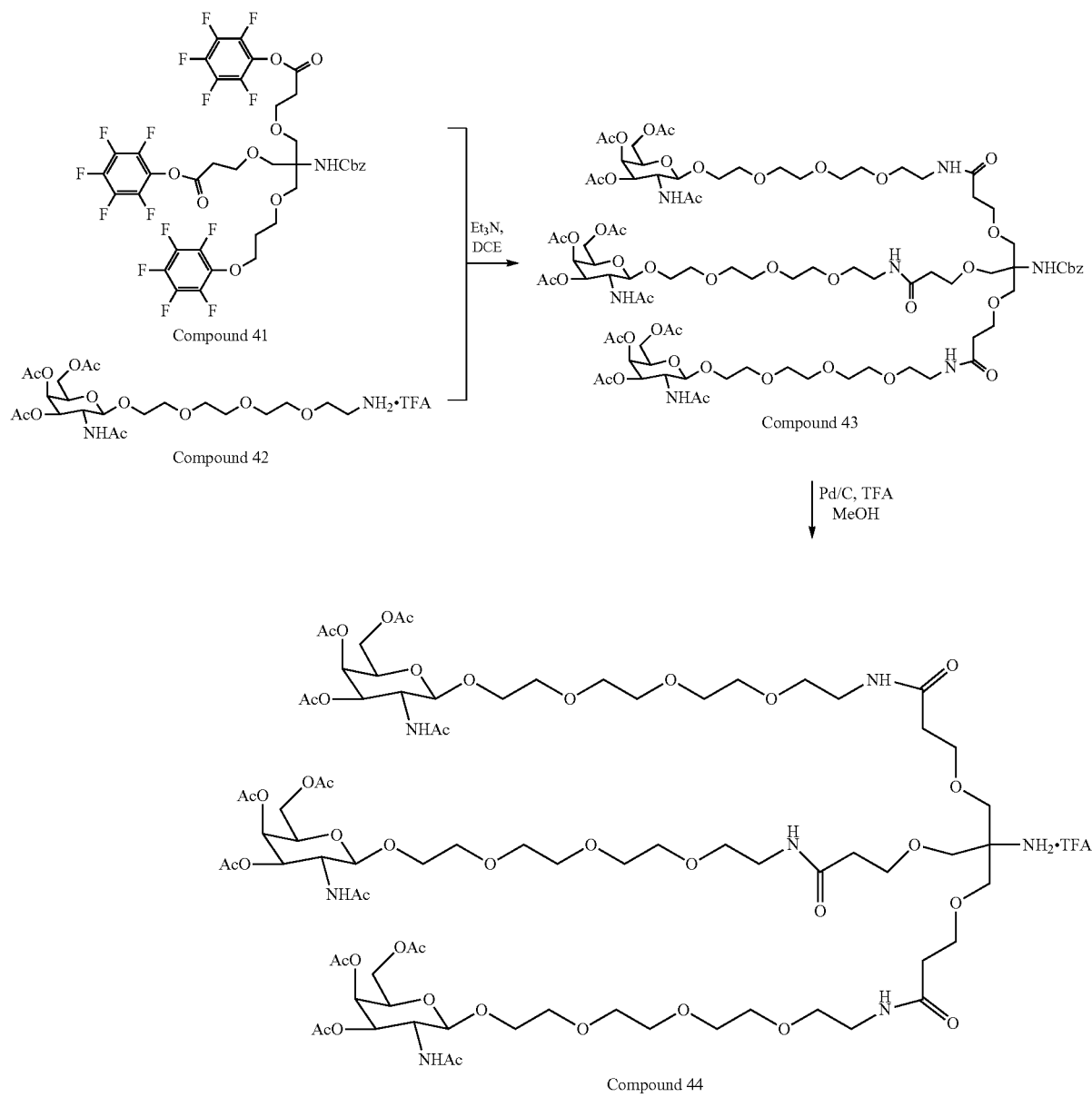

-continued
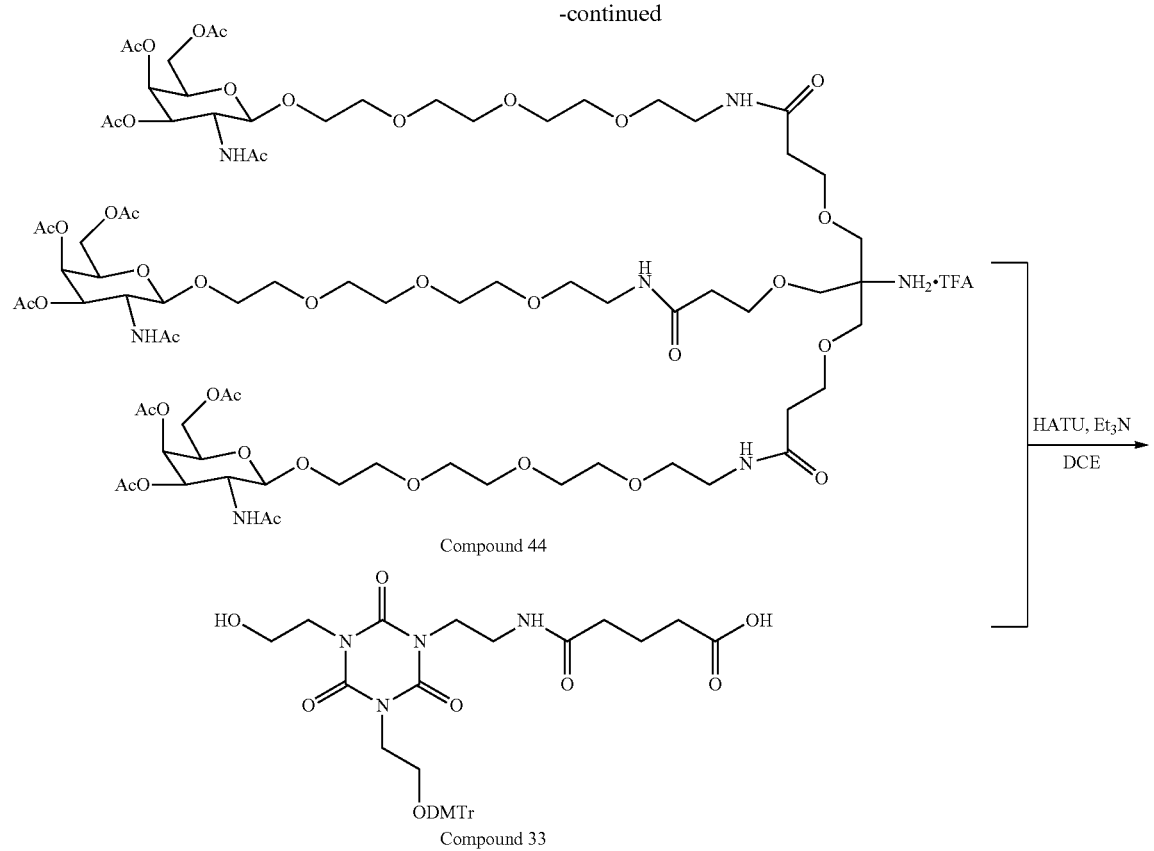
Compound 44
Compound 33
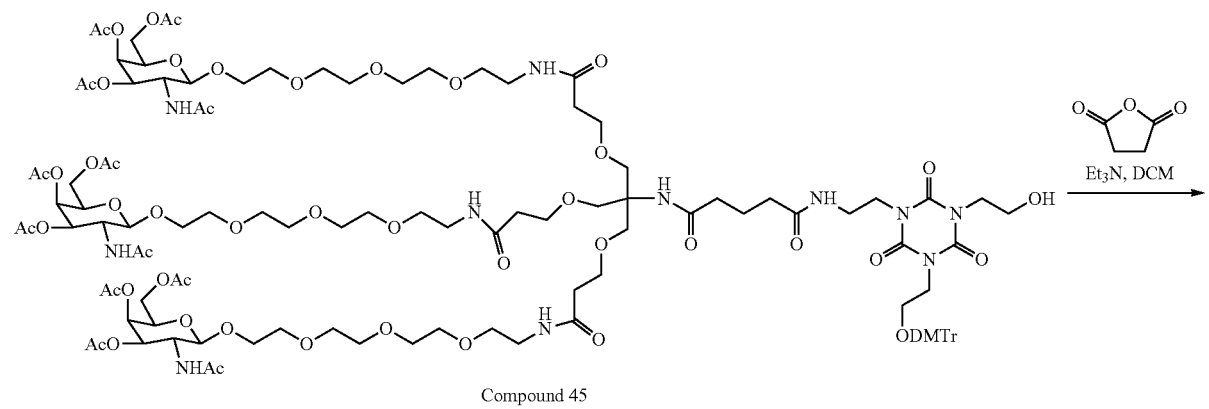
Compound 45
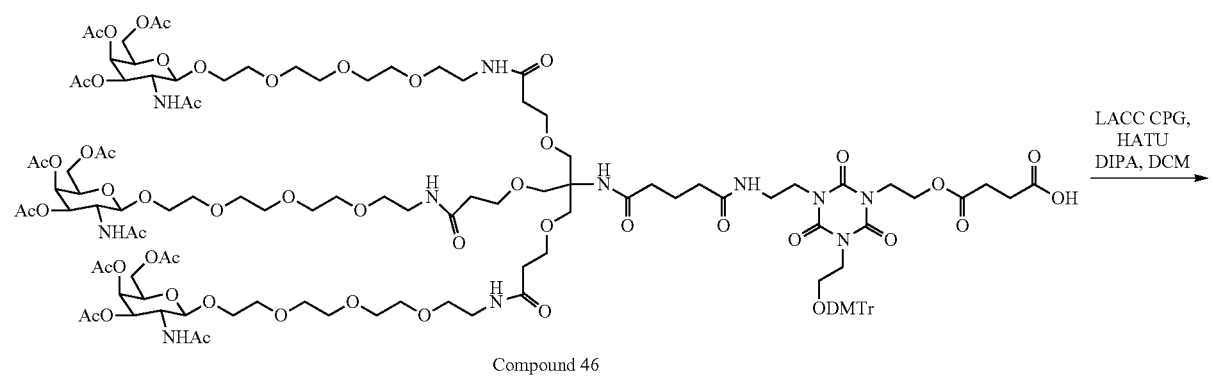
Compound 46

-continued
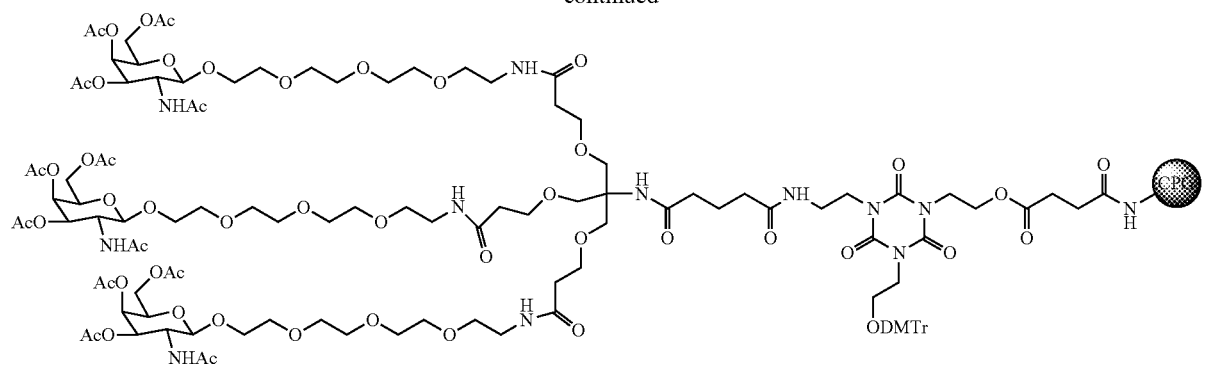
Compound 48
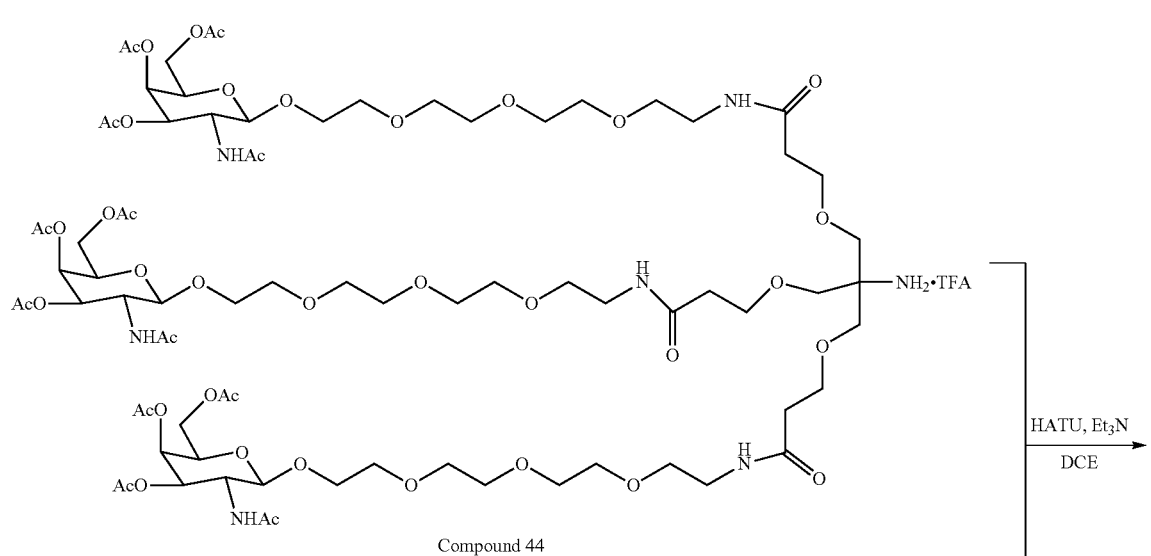
Compound 44
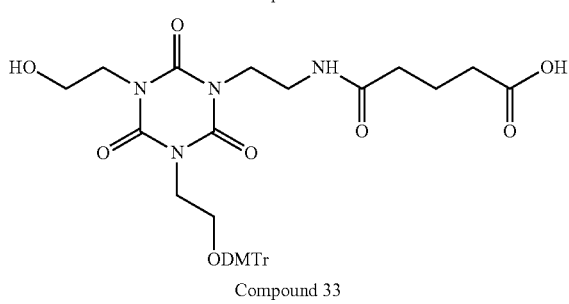
Compound 33
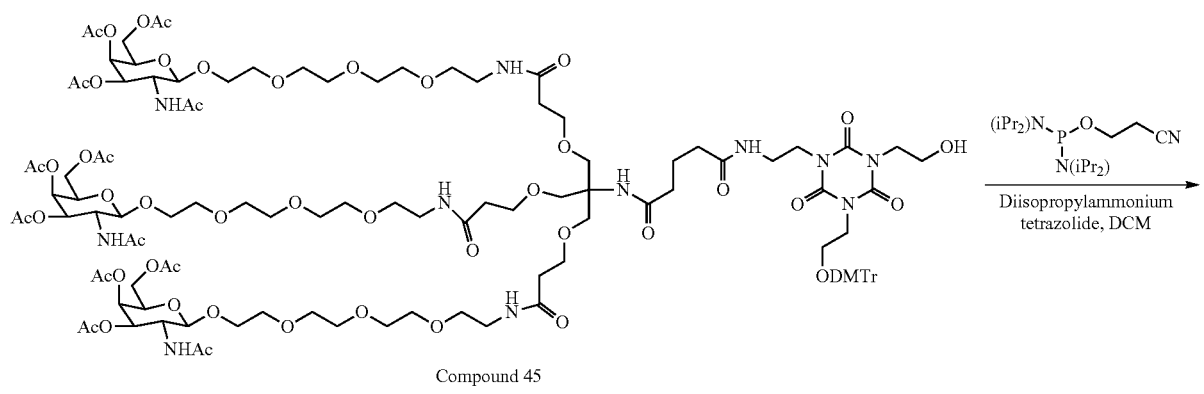
Compound 45

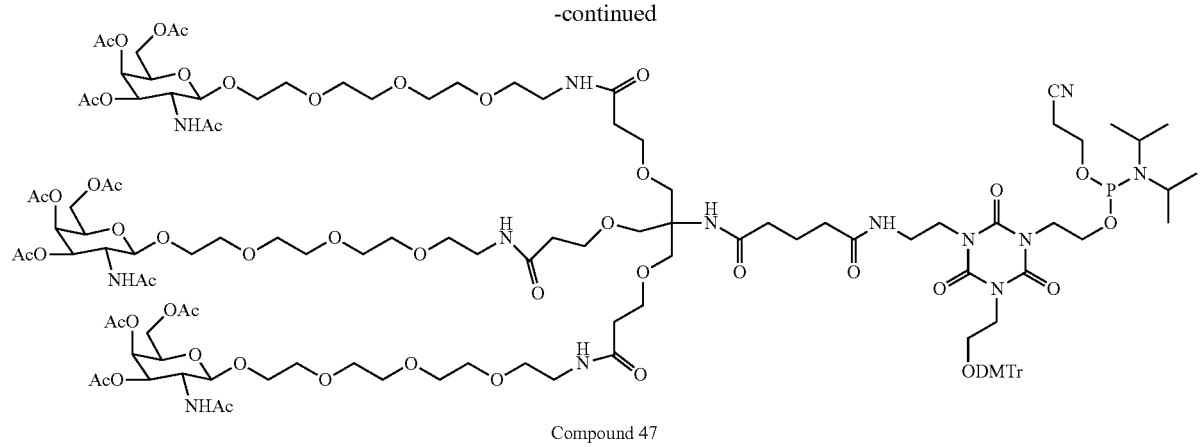

Compound 47

Synthesis of Compound 40: To a solution of Compound 38 (16.87 g, 33.3 mmol) in DCM and 25% aq Na$_2$CO$_3$ (200 mL/200 mL) was added CbzCl (17.04 g, 100 mmol), and the resulting reaction mixture was stirred at rt for 20 h. TLC indicated completion of the reaction. The mixture was diluted with H$_2$O/DCM (100 mL/100 mL), the aqueous layer was then extracted with DCM (50 mL×2), and the organic phase was washed with H$_2$O/brine (50 mL/50 mL). The combined organic layers were dried over Na$_2$SO$_4$, filtered and concentrated. The residue was purified by column chromatography eluting with ethyl Acetate/hexanes (5-20% ethyl acetate in hexanes) to give the Compound 39 (20.57 g) as a colorless oil. Compound 39 (20.57 g, 32.15 mmol) was then dissolved in 25% TFA in DCM (150 mL) at rt, then the reaction mixture was stirred for 3 h at rt. TLC indicated completion of the reaction. The mixture was concentrated to give Compound 40 (15.2 g, 97% for 2 steps) as a white solid. MS: found: [M−H]$^−$=470.5; calc: [M−H]$^−$=470.5.

Synthesis of Compound 41: To a solution of Compound 39 (12.62 g, 26.72 mmol) in anhydrous DCM (130 mL) was added pentafluorophenyl trifluoroacetate (37.43 g, 133.6 mmol) and DIPEA (55 mL, 317.04 mmol). The reaction mixture was stirred for 1 h at rt. TLC indicated completion of the reaction. The mixture was diluted with H$_2$O/DCM (25 mL/50 mL). The aqueous layer was extracted with DCM (25 mL×2). The combined organic layers were dried over Na$_2$SO$_4$, filtered and concentrated. The residue was purified by column chromatography eluting with ethyl acetate/hexanes (0-20% ethyl acetate in hexanes) to provide Compound 41 (4.61 g, 18%) as a colorless oil. MS: found: [M+H]$^+$=970.4; calc: [M+H]$^+$=970.6.

Synthesis of Compound 43: To a solution of Compound 42 (10 g, 15.72 mmol) and Compound 41 (2.5 g, 2.58 mmol) in anhydrous DCE (50 mL) was added Et$_3$N (3.2 g, 13.6 mmol). The reaction mixture was stirred for 45 h at rt. TLC indicated completion of the reaction. The mixture was diluted with H$_2$O/DCM (15 mL/15 mL). The aqueous layer was extracted with DCM (20 mL×2). The combined organic layer was washed by aq. NaHCO$_3$ (15 mL×2) and brine (15 mL×2), dried over Na$_2$SO$_4$, filtered and concentrated. The residue was purified by column chromatography eluting with DCM/MeOH (0-15% MeOH in DCM) to provide Compound 43 (2.5 g, 48%) as a light brown foam. MS: found: [M+2H/2]$^+$=993.6; calc: [M+2H/2]$^+$=993.5.

Synthesis of Compound 44: To a solution of Compound 43 (3.1 g, 1.56 mmol) in MeOH (120 mL) was added trifluoroacetic acid (178 mg, 3.0 mmol) and Pd/C (310 mg, 10%) under N$_2$ atmosphere. The mixture was then exchanged with H$_2$ and stirred for 6 h under H$_2$ atmosphere at rt. TLC indicated completion of the reaction. The mixture was filtered by celite and concentrated to give Compound 44 (3.0 g, 98%) as a brown oil. MS: found: [M+2H/2]$^{2+}$=926.6; calc: [M+2H/2]$^{2+}$=926.5.

Synthesis of Compound 45: To a solution of Compound 33 (1.28 g, 1.89 mmol) and Compound 44 (3.0 g, 1.52 mmol) in anhydrous DCE (60 mL) was added Et$_3$N (640 mg, 6.32 mmol) and HATU (1.2 g, 3.16 mmol). The reaction mixture was stirred for 26 h at rt. TLC indicated completion of the reaction. The mixture was diluted with H$_2$O/DCM (25 mL/25 mL), and the aqueous layer was extracted with DCM (20 mL×2). The combined organic layer was washed by aq. NaHCO$_3$ (20 mL×2) and brine (20 mL×2), dried over Na$_2$SO$_4$, filtered and concentrated. The residue was purified by column chromatography eluting with DCM/MeOH (0-10% MeOH in DCM) to provide Compound 45 (2.79 g, 73%) as a white foam. MS: found: [M+2H/2+NH$_4$]$^{2+}$=1272.8; calc: [M+2H/2+NH$_4$]$^{2+}$=1273.1.

Synthesis of Compound 46: To a solution of Compound 45 (790 mg, 0.31 mmol) in DCM (15 mL) was added Et$_3$N (157 mg, 1.55 mmol) and succinic anhydride (81.8 mg, 0.82 mmol), and the mixture was stirred at rt for 5 h. TLC revealed completion of the reaction. The mixture was diluted with H$_2$O/DCM (10 mL/10 mL). The aqueous layer was extracted with DCM (10 mL×2). The combined organic layer was washed by H$_2$O (10 mL×2) and brine (10 mL×2), dried over Na$_2$SO$_4$, filtered and concentrated to give Compound 46 (744 mg, 92%) as a white foam. MS: found: [M+2H/2+NH$_4$]$^{2+}$=1322.9; calc: [M+2H/2+NH$_4$]$^{2+}$=1323.1.

Synthesis of Compound 48: To a solution of TriGalNAc succinate Compound 46 (744 mg, 0.258 mmol) in anhydrous acetonitrile (17.35 mL) was added HATU (98 mg, 0.258 mmol) and DIPEA (100 mg, 0.776 mmol). The mixture was stirred at rt for 10 min. Pretreated LCAA CPG 500 Å (3.45 g, loading: 75 µmol/g) was added. The resulting mixture was slowly agitated at 25° C. for 3 h. The mixture was then filtered, the CPG was washed with acetonitrile (17 mL×3) and THF (17 mL×3) successively. The CPG was dried under reduced pressure for 3 h. Loading was determined by standard DMTr assay by UV-Vis (498 nm) to be 53 µmol/g.

To the CPG was added a mixture of Ac$_2$O (1.725 mL) and pyridine (1.725 mL) in anhydrous THF (13.8 mL). The resulting mixture was slowly agitated at 25° C. for 30 min.

The mixture was then filtered, and the CPG was washed with THF (17 mL×3), 10% pyridine in MeOH (17 mL×3), MeOH (17 mL×3), acetonitrile (17 mL×2) and DCM (17 mL×1) successively. The capped CPG was dried under reduced pressure for 3 h to give the TriGalNAc CPG product Compound 48 (3.73 g, Loading was determined by standard DMTr assay by UV-Vis (498 nm) to be 53 μmol/g). Ninhydrin test: negative.

Synthesis of Compound 47: To a solution of Compound 45 (1.0 g, 0.398 mmol) in anhydrous DCM (20 mL) was added diisopropylammonium tetrazolide (17.1 mg, 0.10 mmol) and Bis(diisopropylamino)(2-cyanoethoxy)phosphine (240 mg, 0.797 mmol). The reaction mixture was stirred for 21 h at rt. TLC indicated completion of the reaction. The mixture was diluted with aq $NaHCO_3$/DCM (10 mL/10 mL). The aqueous layer was extracted with DCM (10 mL×2). The combined organic layer was washed by aq. $NaHCO_3$ (10 mL×2), dried over $Na_2SO_4$, filtered and concentrated. The residue was dissolved in $CH_3CN$ (35 mL) and extracted with Hexane (10 mL×2), the $CH_3CN$ phase was concentrated. The residue was purified by column chromatography (eluting with 0-5% MeOH in (1% $Et_3N$ in DCM) to provide the TriGalNAc amidite Compound 47 (745 mg, 70%) as a white foam. MS: found: $[M+2H/2+NH_4]^{2+}$=1373.1; calc: $[M+2H/2+NH_4]^{2+}$=1373.9. $^{31}$PNMR (mixture of diastereomers, singlet, DMSO-$d_6$): δ 148.05.

Example 8. General Procedure for the Preparation of Monovalent GalNAc Analogs

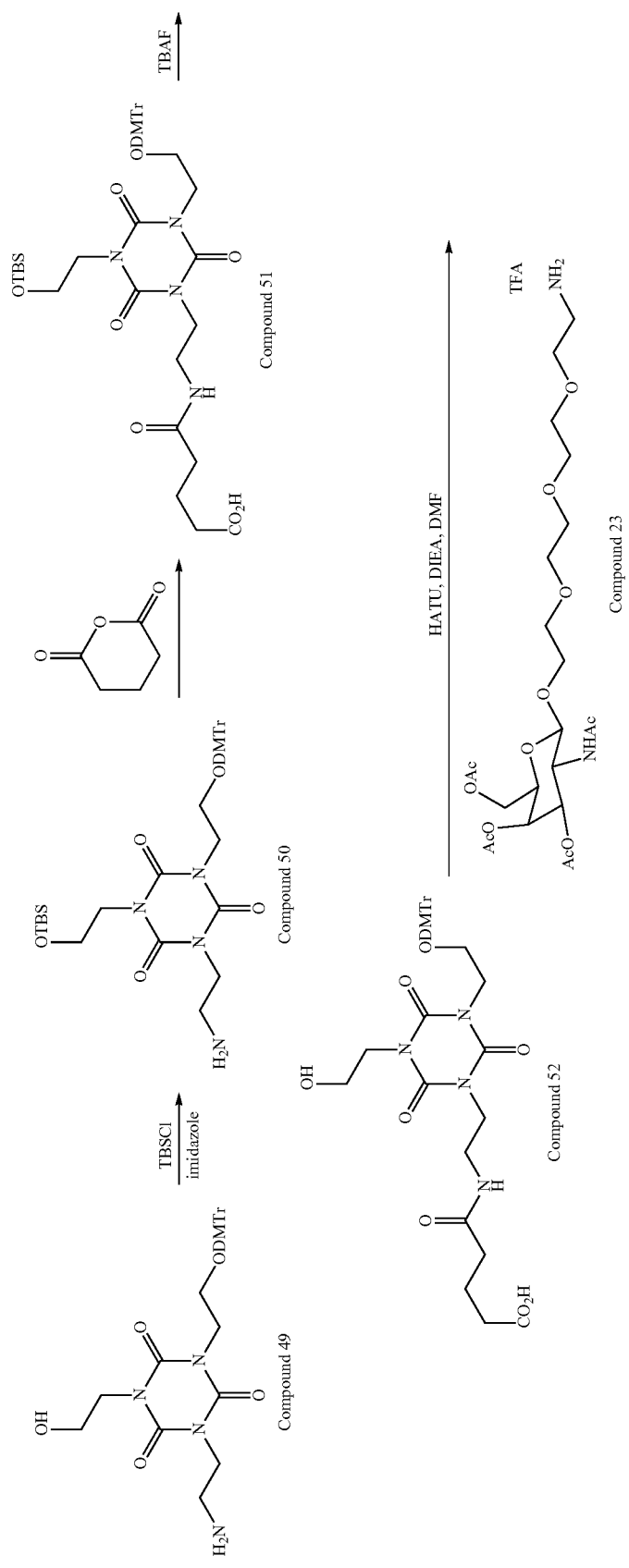

-continued
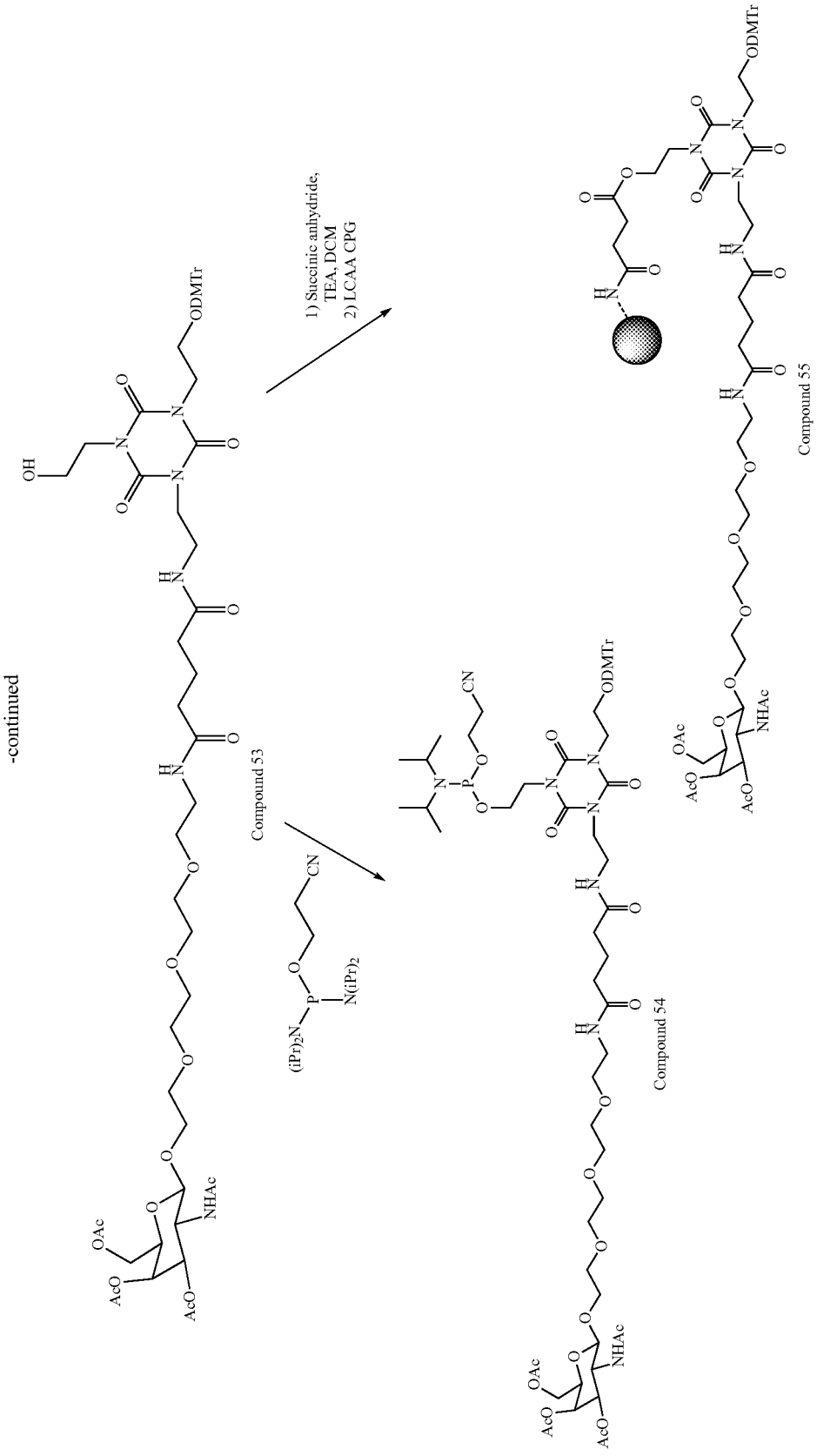

Compound 50: Compound 49 (1.6 g, 2.85 mmol), TBDMSCl (889 mg, 5.89 mmol), and imidazole (580 mg, 8.54 mmol) were dissolved in DCM (20 mL). The reaction mixture was stirred at room temperature overnight and monitored by TLC. Solvents were removed, and the residual was subjected to FCC with DCM/MeOH (10% MeOH) to afford Compound 50 (1.42 g, 74%) as a white solid. MS: found: [M+H]=677.7; calc: [M+H]=677.3.

Compound 51: To a solution of Compound 50 (1.42 g, 2.1 mmol) in DCM (20 mL) was added glutaric anhydride (287 mg, 2.52 mmol) and triethylamine (424 mg, 4.2 mmol). The reaction was monitored by LCMS. Upon completion, the mixture was evaporated to form crude Compound 51 which was used directly for the next step. MS: found: [M−H]= 789.6; calc: [M−H]=789.4.

Compound 52: To a solution of Compound 51 (2.1 mmol) in THF (20 mL) was added TBAF (2.3 mmol). The reaction was monitored by TLC. Upon completion, the mixture was concentrated, and subjected to FCC using EA/TEA (100/1) to EA/TEA/MeOH (100/1/10) to afford Compound 52 (1.1 g, 77%) as a colorless oil. MS: found: [M−H]=675.5; calc: [M−H]=675.3.

Compound 53: To a solution of Compound 52 (1.0 g, 1.5 mmol) in DMF (10 mL) was added HATU (855 mg, 2.3 mmol) and TEA (417 μL, 3.0 mmol). The reaction mixture was stirred at room temperature for 30 minutes, after which Compound 23 (1.24 g, 1.95 mmol) was added. The reaction mixture was stirred at r.t. overnight and monitored by TLC. Upon completion, the reaction was quenched by the addition of water (100 mL). The mixture was extracted with DCM (100 mL), and the organic layer was washed with water (100 ml×3) and brine (100 mL). The organic phase was dried over sodium sulfate, filtered, and concentrated to dryness, which was then subjected to FCC using DCM to DCM/MeOH (0 to 10% MeOH) to afford Compound 53 (240 mg, 20%) as a pale-yellow solid. MS: found: [M+H]=1181.8; calc: [M+H]=1181.5.

Compound 54: Compound 53 (190 mg, 0.17 mmol) and diisopropylammonium tetrazolide (7.3 mg, 0.043 mmol) were dissolved in DCM (2 mL), followed by the addition of 3-((bis(diisopropylamino)phosphanyl)oxy)propanenitrile (102 mg, 0.34 mmol). The reaction was stirred at rt. and monitored by LCMS. Upon completion, the reaction was quenched by saturate sodium bicarbonate (3 mL), and washed with saturate sodium bicarbonate (3×3 mL) and brine (3 mL). The organic layer was dried over sodium sulfate, filtered, and concentrated. The residual was dissolved in acetonitrile (3 mL), and washed with heptane (3×3 mL). The acetonitrile layer was concentrated and subjected to FCC using DCM/TEA (0.5% TEA in DCM) to TEA/ DCM/MeOH (0.5/100/10) to afford Compound 54 (52 mg, 20%) as a white solid. MS: found: [M+H]=1382.1; calc: [M+H]=1382.5. $^{31}$PNMR (mixture of diastereomers, broad singlet): $\delta$=147.320.

Compound 55: Step 1: To a solution of Compound 53 (50 mg, 0.042 mmol) in DCM (1 mL) was added succinic anhydride (6.3 mg, 0.06 mmol) and triethylamine (8.6 mg, 0.085 mmol). The reaction mixture was stirred overnight and monitored by LCMS. Upon completion, the mixture was concentrated, and the crude succinate product was used directly for the next step. MS: found: [M+H]=1281.9; calc: [M+H]=1281.5.

Step 2: The crude succinate from step 1, LCAA CPG (0.3 g 1000 Å), TBTU (20 mg, 1.5 eq.), TEA (8.5 mg, 2 eq.) were dispersed in acetonitrile (3.5 mL). This mixture was placed on a rotovap and stirred for 2 h at 25 degrees Celsius. The mixture was filtered, and the CPG was washed with acetonitrile (3×3 mL), THF (3×3 mL), and MTBE (3×3 mL), and then dried to afford uncapped CPG. The uncapped CPG was then dispersed in THF (3.5 mL) with acetic anhydride (0.14 mL), pyridine (0.14 mL) and NMI (0.14 mL). The mixture was placed on a rotovap and stirred for 1 h at 25 degrees Celsius. The mixture was then filtered, and the capped CPG was washed with pyridine/10% ethanol (3×3 mL), ethanol (3×3 mL), MeCN (3×3 mL), THF (3×3 mL), and MTBE (3×3 mL), and dried to afford desired CPG Compound 55. Loading was determined by standard DMTr assay by UV-Vis (498 nm) to be 23 μmol/g.

Example 9. Preparation of GalNAc-Conjugated Oligonucleotides

GalNAc-conjugated oligonucleotides are synthesized on a DNA/RNA synthesizer starting with a commercial DMTr-nucleoside-succinyl-CPG (1000 Å, Glen Research, Sterling, Va.). The standard synthetic cycle useful in assembling oligonucleotides comprise the steps of: (a) detritylation of the solid phase-bound material; (b) coupling of nucleoside phosphoramidite building block required by the sequence to the solid support-bound material in the presence of coupling agent; (c) capping of unreacted solid support-bound hydroxy groups with a mixture of acetic anhydride and N-methyl imidazole and (d) oxidation of the solid support-bound phosphite triester groups. The cycle appropriate for the assembly of the desired oligonucleotide was repeated as required by the sequence in preparation.

The final release of GalNAc-conjugated oligonucleotides from the solid support, deprotection of internucleosidic phosphates, and monosaccharide residues is carried out by treatment under the following standard condition. Upon completion of the deprotection under the conditions above, the liquid phase is collected and evaporated in vacuo to dryness. The residue is dissolved in water (1 mL) and analyzed by reverse-phase HPLC and by ES MS.

To demonstrate the usage of novel linker designs for mono- and tri-GalNAc-conjugated phosphoramidites in oligonucleotide synthesis, a sequence was designed for trails: 5'-X-TTTTTTTTTT (SEQ ID NO:1)-3', where X represents a GalNAc-conjugated phosphoramidite described herein. The following compounds were generated: Compound X1, Compound X2, and Compound X3.

Oligonucleotides (Compounds X1-X3) were synthesized by a solid-phase phosphoramidite method from a MerMade 6 synthesizer (LGC, Biosearch Technologies). A DMT-dT solid support was packed in an empty column and the column was placed into the synthesizer. The synthetic scale is 200 nmol. The oligonucleotide synthesis cycle included the following steps: (1) detritylation with 3% trichloroacetic acid in dichloromethane for 45 seconds two times, followed by acetonitrile washing; (2) coupling with 0.1 M DMT-dT-CE-Phosphoramidite (5'-O-(4, 4'-Dimethoxytrityl)-thymidine-3'-cyanoethyl Phosphoramidite) in acetonitrile and 0.5 M activator (tetrazole in acetonitrile) for 1 minute two times, followed by acetonitrile washing; (3) oxidation with iodine (0.015 M iodine in water/pyridine/THF 2/20/78) for 45 seconds, followed by acetonitrile washing; and (4) capping with a mixture of acetic anhydride, pyridine, and THF for 45 seconds, followed by acetonitrile washing. Steps (1)-(4) were repeated 9 times for synthesizing a T10 elongated from the solid support. The final cycle to couple the novel mono- or tri-GalNAc-conjugated phosphoramidites includes the sample detritylation, oxidation, and capping step, while the coupling uses a mixture of 0.1 M phosphoramidites in acetonitrile and 0.5 M activator for 3 minutes two times for mono-GalNAc and 6 minutes two times for tri-GalNAc, followed by acetonitrile washing.

After synthesis, the oligonucleotide-bounded solid supports were treated with a 1:1 mixture of aqueous ammonia hydroxide and methylamine at 55° C. for 2 hours for cleavage and deprotection. Upon completion, the liquid phase was collected and heat dried in a vacuum concentrator. The dried residue was dissolved in water and analyzed by reverse-phase HPLC (Agilent 1260) and LC-MS (Applied Biosystems 4000 Q-Trap). For Seq X1, the HPLC gradient was 20-60% B in 20 minutes, with Buffer A: 50 mM triethylammonium acetate in water and Buffer B: 80% 50 mM triethylammonium acetate in water and 20% acetonitrile. For Seq X2 and X3 with tri-GalNAc, the HPLC gradient was 30-70% B in 20 minutes. The retention time (RT), MS calculated, MS found, and full-length product purity (FLP) for each sequence (Compound X1-X3) are listed in Tables 1 and 2.

TABLE 1

Usage tests of mono-GalNAc-conjugated phosphoramidites in oligonucleotides with 20-60% B HPLC gradient

| Compound | X (Phosphoramidite) | Conc. | RT (min) | MS Calculated | MS Found | FT (%) |
|---|---|---|---|---|---|---|
| Compound X1 | Compound 16 | 0.1M | 16.864 | 3651.5 | 3652.5 | 31.9 |

TABLE 2

Usage tests of tri-GalNAc-conjugated phosphoramidites in oligonucleotides with 30-70% B HPLC gradient

| Compound | X (Phosphoramidite) | Conc. | RT (min) | MS Calculated | MS Found | FT (%) |
|---|---|---|---|---|---|---|
| Compound X2 | Compound 36 | 0.1M | 15.594 | 4766.8 | 4765.4 | 2.6 |
| Compound X3 | Compound 47 | 0.1M | 15.824 | 4870.9 | 4872.9 | 20.7 |

Example 10. Preparation of GalNAc-Conjugated Oligonucleotides on Solid Supports To demonstrate the usage of novel linker designs for mono- and tri-GalNAc-conjugated solid supports in oligonucleotide synthesis, a sequence was designed for trials: 5'-TTTTTTTTTT (SEQ ID NO: 1)-Y-3', where Y represents mono- or tri-GalNAc-conjugated solid support. The following support bound compounds were generated: Compound Y1, Compound Y2, Compound Y3, and Compound Y4.

Oligonucleotides (Compounds Y1-Y4) were synthesized by a solid-phase phosphoramidite method. A novel DMT-mono/tri-GalNAc-conjugated solid support (Y) was packed in an empty column and put into the MerMade 6 synthesizer. The synthetic scale is 0.5-1 μmol. The oligonucleotide synthesis cycle includes the following steps: (1) detritylation with 3% trichloroacetic acid in dichloromethane for 45 seconds two times, followed by acetonitrile washing; (2) coupling with 0.1 M DMT-dT-CE-Phosphoramidite (5'-O-(4, 4'-Dimethoxytrityl)-thymidine-3'-cyanoethyl Phosphoramidite) in acetonitrile and 0.5 M activator (tetrazole in acetonitrile) for 1 minute two times, followed by acetonitrile washing; (3) oxidation with iodine (0.015 M iodine in water/pyridine/THF 2/20/78) for 45 seconds, followed by acetonitrile washing; and (4) capping with a mixture of acetic anhydride, pyridine, and THF for 45 seconds, followed by acetonitrile washing. Steps (1)-(4) were repeated 10 times for synthesizing a T10 elongated from the GalNAc conjugated solid support and were finished by the final detritylation with acetonitrile washing.

After synthesis, the oligonucleotide-bounded solid supports were treated with a 1:1 mixture of aqueous ammonia hydroxide and methylamine at 55° C. for 2 hours for cleavage and deprotection. Upon completion, the liquid phase was collected and heat dried in a vacuum concentrator. The dried residue was dissolved in water and analyzed by reverse-phase HPLC (Agilent 1260) and LC-MS (Applied Biosystems 4000 Q-Trap). For Y1 and Y2, the HPLC gradient was 20-60% B in 20 minutes, with Buffer A: 50 mM triethylammonium acetate in water and Buffer B: 80% 50 mM triethylammonium acetate in water and 20% acetonitrile. For Y3 and Y4 with tri-GalNAc, the HPLC gradient was 30-70% B in 20 minutes. The retention time (RT), MS calculated, MS found, and full-length product purity (FLP) for each sequence (Compounds Y1-Y4) are listed in Tables 3 and 4.

TABLE 3

Usage tests of mono-GalNAc-conjugated CPG in oligonucleotides with 20-60% B HPLCgradient

| Compound | Y (CPG) | loading | RT (min) | MS Calculated | MS Found | FT (%) |
|---|---|---|---|---|---|---|
| Compound Y1 | Compound 55 | 23 | 17.747 | 3794.7 | 3795.5 | 38.8 |
| Compound Y2 | Compound 17 | 41 | 16.842 | 3651.5 | 3650.7 | 27.2 |

TABLE 4

Usage tests of tri-GalNAc-conjugated CPG in oligonucleotides with 30-70% B HPLC gradient

| Compound | Y (CPG) | loading | RT (min) | MS Calculated | MS Found | FT (%) |
|---|---|---|---|---|---|---|
| Compound Y3 | Compound 37 | 49 | 17.354 | 4766.8 | 4766.5 | 54.5 |
| Compound Y4 | Compound 48 | 53 | 18.053 | 4870.9 | 4871.4 | 62.1 |

While the present application has been described with reference to the specific embodiments thereof, it should be understood by those skilled in the art that various changes may be made and equivalents may be substituted without departing from the true spirit and scope of the present application. In addition, many modifications may be made to adapt a particular situation, material, composition of matter, process, process step or steps, to the objective, spirit and scope of the present application. All such modifications are intended to be within the scope of the claims appended hereto.

What is claimed is:

1. A compound of Formula (II):

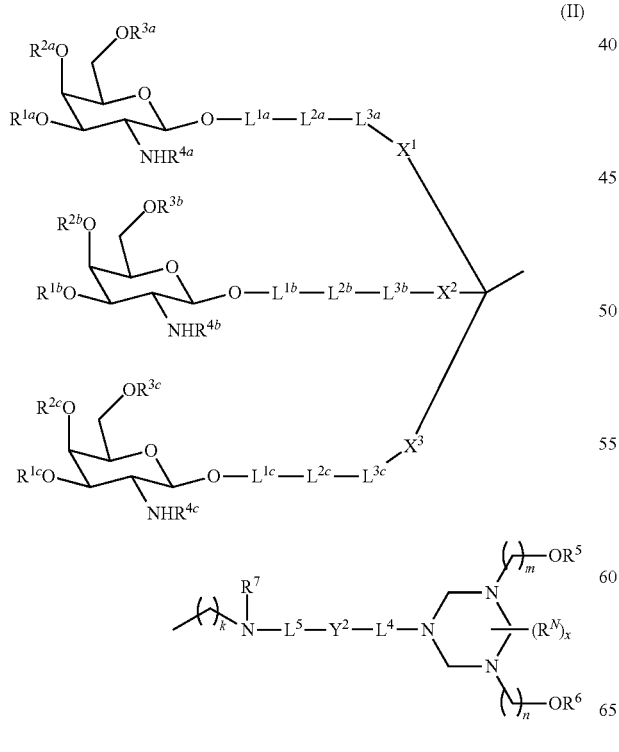

(II)

or a pharmaceutically acceptable salt thereof, wherein each of $R^{1a}$, $R^{1b}$, $R^{1c}$, $R^{2a}$, $R^{2b}$, $R^{2c}$, $R^{3a}$, $R^{3b}$, and $R^{3c}$ is independently hydrogen, benzyl, or —C(=O)$R^8$;

each of $R^{4a}$, $R^{4b}$ and $R^{4c}$ is independently —C(=O)$C_{1-6}$ alkyl or —C(=O)$C_{1-6}$ haloalkyl;

$R^5$ is a hydroxy protecting group;

$R^6$ is hydrogen, a phosphoramidite moiety, —C(=O)CH$_2$CH$_2$C(=O)$R^{6A}$, or —P(O$R^{6B}$)N$R^{6C}R^{6D}$;

$Y^2$ is a bond, N$R^7$, N$R^7$C(=O), C(=O)O, or O;

each of $X^1$, $X^2$ and $X^3$ is independently —O(CH$_2$)$_{1-3}$—, —NH(CH$_2$)$_{1-3}$—, —C(=O)(CH$_2$)$_{1-3}$— or —NHC(=O)(CH$_2$)$_{1-3}$—;

each of $L^{1a}$, $L^{1b}$, $L^{1c}$, $L^{2a}$, $L^{2b}$, $L^{2c}$, $L^{3a}$, $L^{3b}$, and $L^{3c}$ is independently a bond, —C(=O)—, —C(=S)—, —S(=O)$_2$—, —C(=O)N$R^9$—, —C(=S)N$R^9$—, —C(=O)O—, —C(=S)O—, —N$R^9$C(=O)N$R^9$—, —N$R^9$C(=S)N$R^9$—, —OP(=O)(OH)O—, —OP(=S)(OH)O—, —O—, —S—, —N$R^9$—, optionally substituted $C_{1-10}$ alkylene, optionally substituted $C_{6-10}$ arylene, optionally substituted $C_{3-10}$ cycloalkylene, optionally substituted 5-10 membered hetetroarylene, optionally substituted 5 to 10 membered heterocyclylene, or optionally substituted 2 to 15 membered heteroalkylene wherein one or more carbon atoms are replaced with C(=O), O, S or N, provided that at least one of $L^{1a}$, $L^{1b}$ and $L^{1c}$ is not a bond, at least one of $L^{2a}$, $L^{2b}$ and $L^{2c}$ is not a bond, and at least one of $L^{3a}$, $L^{3b}$ and $L^{3c}$ is not a bond;

$L^4$ is a bond, optionally substituted $C_{1-8}$ alkylene or —(CH$_2$)$_{1-3}$(OCH$_2$CH$_2$)$_{1-5}$OCH$_2$—;

$L^5$ is a bond, optionally substituted $C_{1-10}$ alkylene, or optionally substituted 2 to 15 membered heteroalkylene wherein one or more carbon atoms are replaced with C(=O), O, S or N;

each of $R^7$ and $R^9$ is independently hydrogen, unsubstituted $C_{1-6}$ alkyl, or substituted $C_{1-6}$ alkyl;

each $R^8$ is independently $C_{1-6}$ alkyl, $C_{1-6}$ haloalkyl, or optionally substituted phenyl;

$R^{6A}$ is —OH, —O$R^{10}$ or —N$R^{11}R^{12}$;

each of $R^{6B}$, $R^{6C}$, $R^{6D}$ is independently H, $C_{1-6}$ haloalkyl, or unsubstituted or substituted $C_{1-6}$ alkyl;

$R^{10}$ is unsubstituted or substituted $C_{1-6}$ alkyl, or a hydroxy protecting group;

each of $R^{11}$ and $R^{12}$ is independently H, unsubstituted or substituted $C_{1-6}$ alkyl, or an amino protecting group;

each of m and n is independently 1, 2, 3, 4, 5 or 6;

k is 0 or 1;

x is 0, 1, 2, 3, 4, 5 or 6; and each $R^N$ is independently halo, cyano, hydroxy, amino, unsubstituted $C_{1-6}$ alkyl, substituted $C_1$-$C_6$ alkyl, $C_1$-$C_6$ haloalkyl, hydroxy($C_1$-$C_6$ alkyl), amino($C_1$-$C_6$ alkyl), ($C_1$-$C_6$ alkyl)amino, $C_1$-$C_6$ alkoxy, $C_1$-$C_6$ haloalkoxy, ($C_1$-$C_6$ alkoxy)$C_1$-$C_6$ alkyl, or —O($C_1$-$C_6$ alkoxy)$C_1$-$C_6$ alkyl, or two adjacent $R^N$ attached to the same carbon atom form oxo (=O).

2. The compound of claim 1, wherein k is 0, $R^7$ is H, and the compound is also represented by Formula (IIa):

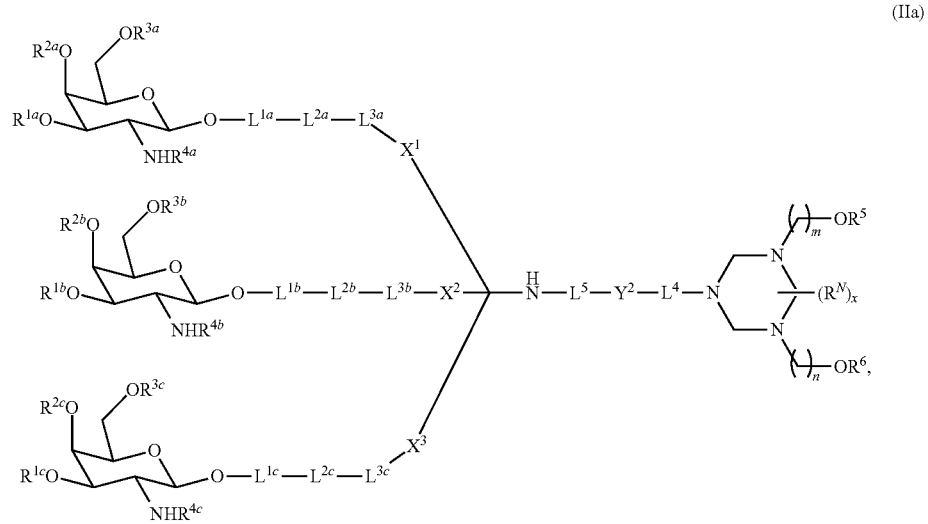

or a pharmaceutically acceptable salt thereof.

3. The compound of claim 1, wherein x is 0.

4. The compound of claim 1, wherein the compound is also represented by Formula (IIb):

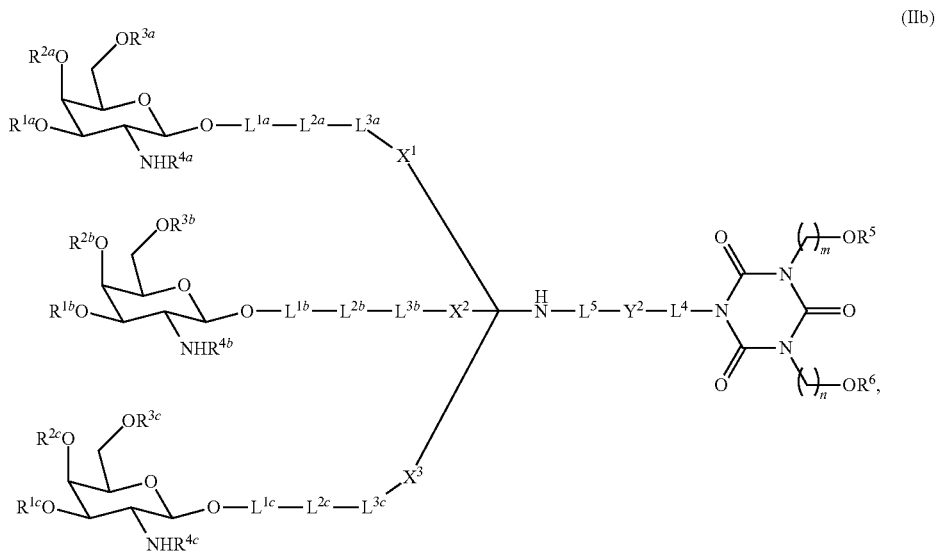

or a pharmaceutically acceptable salt thereof.

5. The compound of claim 1, wherein $L^4$ is a $C_{1-6}$ alkylene.

6. The compound of claim 1, wherein $Y^2$ is C(O)O and the compound is also represented by Formula (IIc):

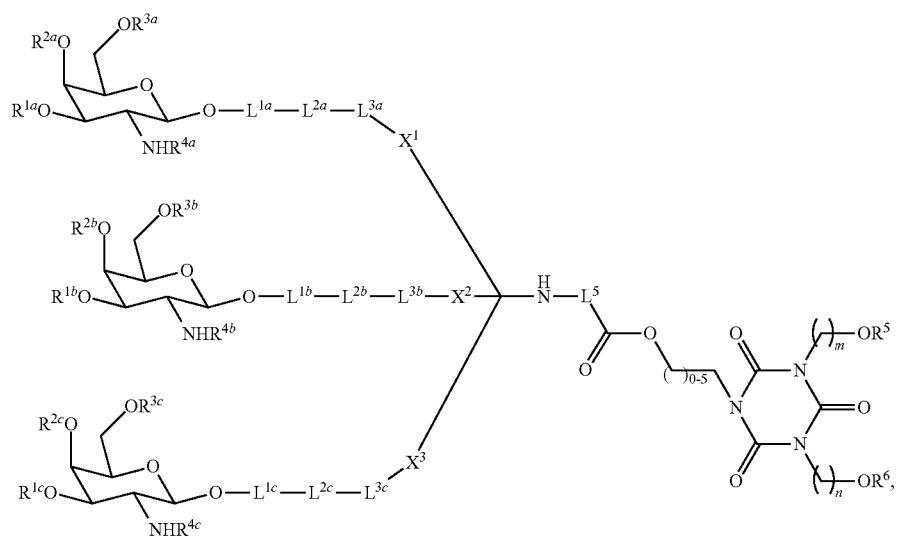

(IIc)

or a pharmaceutically acceptable salt thereof.

7. The compound of claim 1, wherein $Y^2$ is NHC(O) and the compound is also represented by Formula (IId):

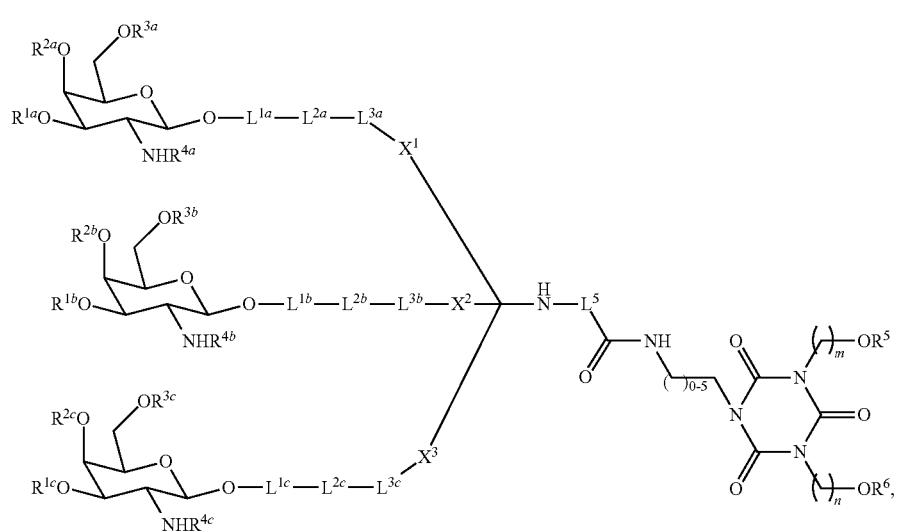

(IId)

or a pharmaceutically acceptable salt thereof.

8. The compound of claim 1, wherein $L^4$ is a bond.

9. The compound of claim 1, wherein $Y^2$ is a bond.

10. The compound of claim 1, wherein $L^5$ is 2 to 15 membered heteroalkylene where one or more carbon atoms are replaced with C(=O), O or N.

11. The compound of claim 10, wherein $L^5$ is —C(=O)—$(CH_2)_{1-5}$.

12. The compound of claim 1, wherein $L^5$ is a bond.

13. The compound of claim 1, wherein each of $X^1$ and $X^3$ is —C(=O)CH$_2$CH$_2$—, and $X^2$ is —C(=O)CH$_2$-.

14. The compound of claim 1, wherein each of $X^1$ and $X^3$ is —NHC(=O)CH$_2$CH$_2$—, and $X^2$ is -NHC(=O)CH$_2$-.

15. The compound of claim 1, wherein each of $X^1$, $X^2$ and $X^3$ is —OCH$_2$—, —NHCH$_2$—, —C(=O)CH$_2$CH$_2$—, —C(=O)CH$_2$—, —NHC(=O)CH$_2$CH$_2$— or —NHC(=O)CH$_2$-.

16. The compound of claim 1, wherein each of $L^{1a}$, $L^{1b}$, $L^{1c}$, $L^{2a}$ $L^{2b}$, $L^{2c}$, $L^{3a}$, $L^{3b}$, and $L^{3c}$ is independently a bond, $C_{1-10}$ alkylene, or 3 to 15 membered heteroalkylene where one or more carbon atoms are replaced with C(=O), O or N.

17. The compound of claim 16, wherein the 3 to 15 membered heteroalkylene is a PEG linker comprising one to five —OCH$_2$CH$_2$— repeating unit.

18. The compound of claim 1, wherein each of $R^{1a}$, $R^{1b}$, $R^{1c}$, $R^{2a}$, $R^{2b}$, $R^{2c}$, $R^{3a}$, $R^{3b}$, and $R^{3c}$ is independently H, —C(=O)CH$_3$ or —C(=O)Ph.

19. The compound of claim 18, wherein each of $R^{1a}$, $R^{1b}$, $R^{1c}$, $R^{2a}$, $R^{2b}$, $R^{2c}$, $R^{3a}$, $R^{3b}$, and $R^{3c}$ is —C(=O)CH$_3$.

20. The compound of claim 1, wherein each of $R^{4a}$, $R^{4b}$ and $R^{4c}$ is —C(=O)CH$_3$ or —C(=O)CF$_3$.

21. The compound of claim 1, wherein both m and n are 1, 2 or 3.

22. The compound of claim 1, wherein $R^5$ is a trityl type of hydroxy protecting group selected from (4-methoxyphenyl)diphenylmethyl, bis(4-methoxyphenyl)phenylmethyl (DMTr), tris(4-methoxyphenyl)methyl, 9-phenylxanthen-9-yl, or 9-(4-methoxyphenyl)xanthen-9-yl.

23. The compound of claim 1, wherein $R^6$ is —C(=O)CH$_2$CH$_2$C(=O)OH or

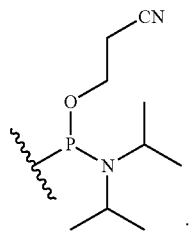 [SMILES: *P(OCCC#N)N(C(C)C)C(C)C]

24. The compound of claim 1, selected from the group consisting of:

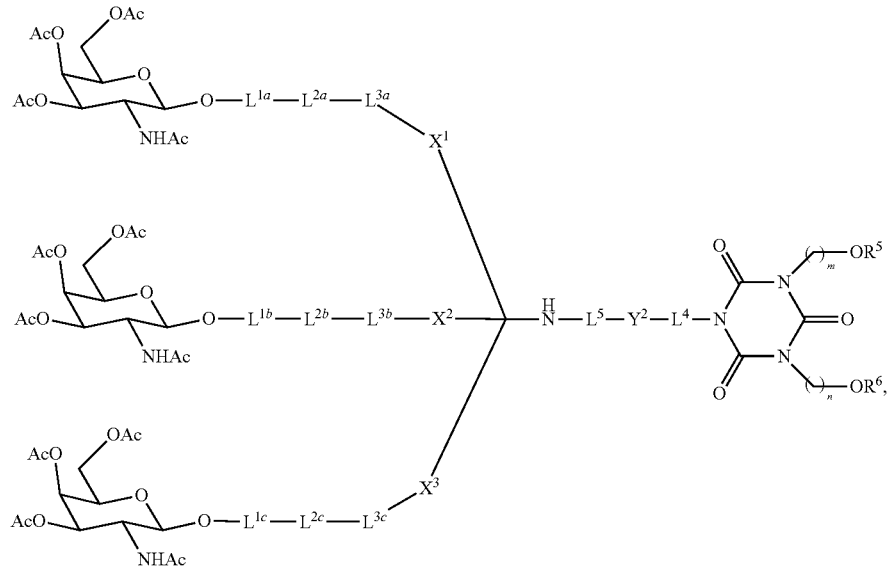

(IIe-1)

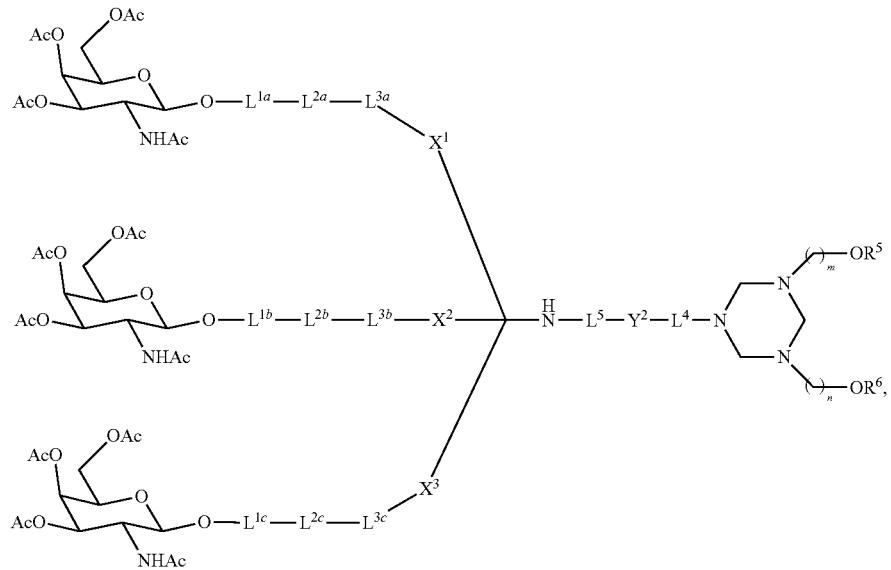

(IIe-2)

-continued
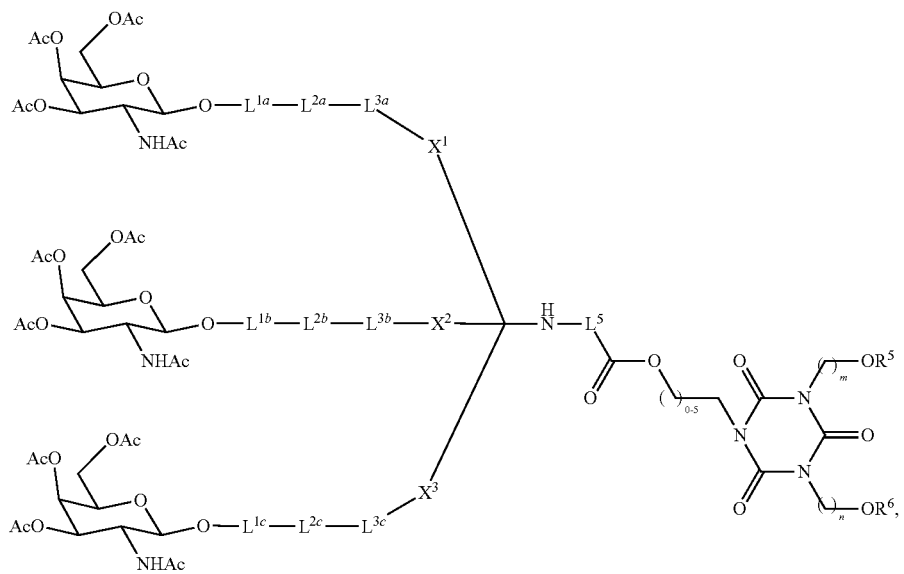
(IIe-3)
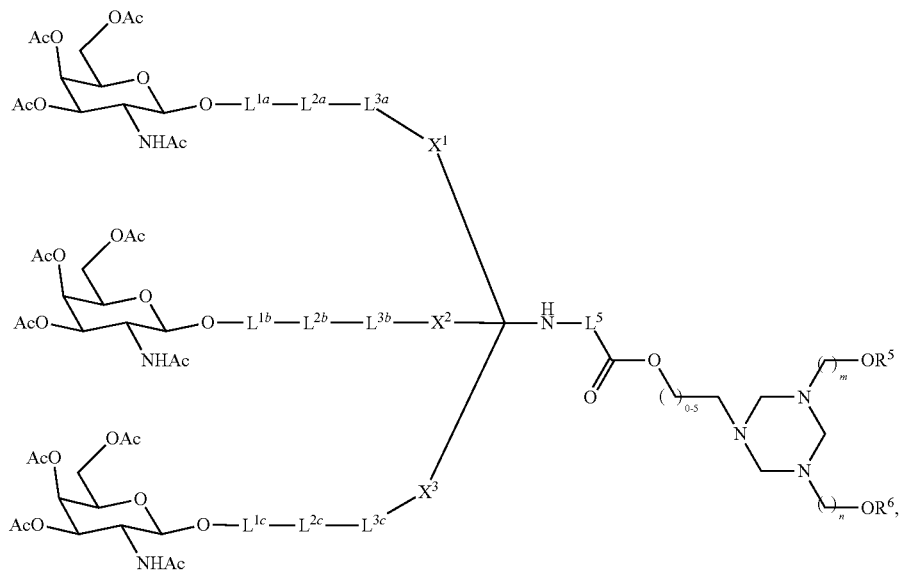
(IIe-4)

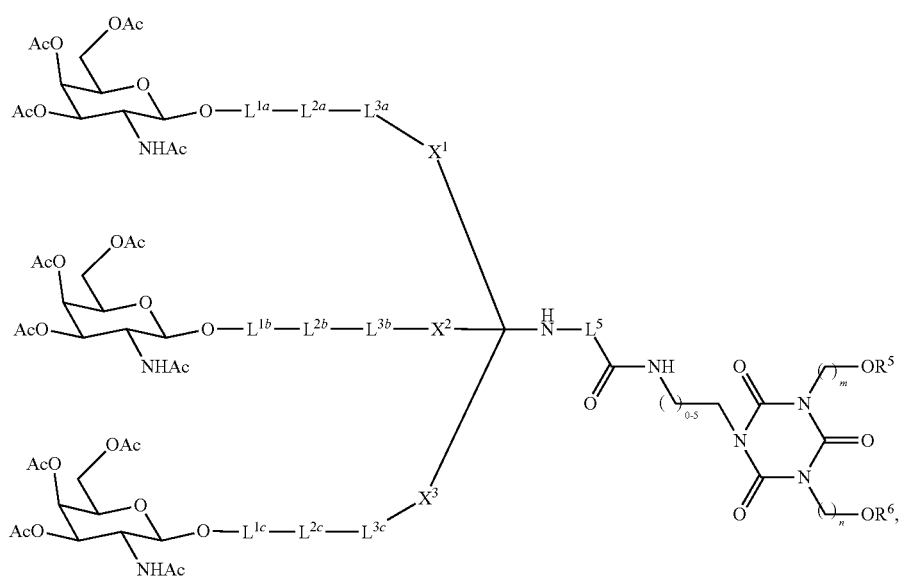
(IIe-5)
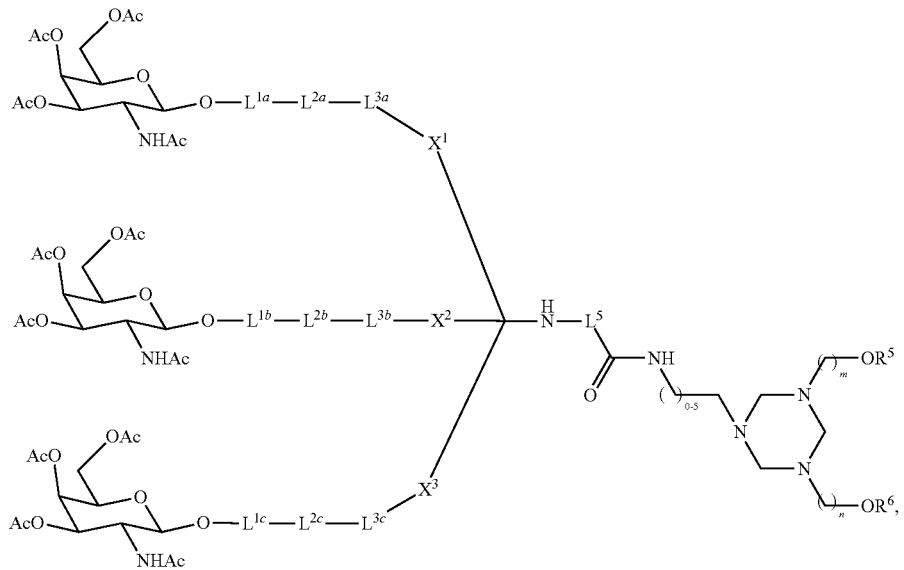
(IIe-6)

(IIe-7)

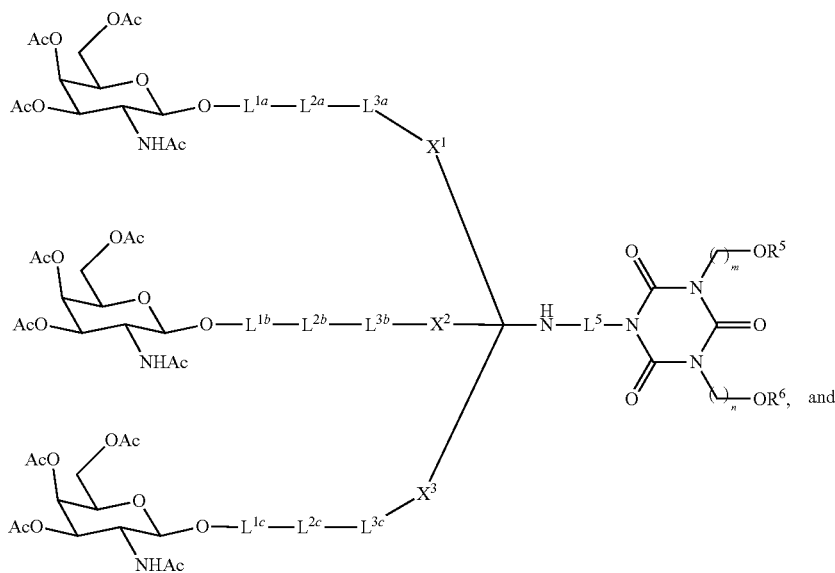

(IIe-8)

and pharmaceutically acceptable salts thereof, wherein each of $X^1$, $X^2$ and $X^3$ is —OCH$_2$—, —NHCH$_2$—, —C(=O)CH$_2$CH$_2$—, —C(=O)CH$_2$—, —NHC(=O)CH$_2$CH$_2$— or —NHC(=O)CH$_2$—, or each of $X^1$ and $X^3$ is —C(=O)CH$_2$CH$_2$—, and $X^2$ is —C(=O)CH$_2$—, or each of $X^1$ and $X^3$ is —NHC(=O)CH$_2$CH$_2$—, and $X^2$ is —NHC(=O)CH$_2$-;

Ac is —C(O)CH$_3$;

each of m and n is independently 1, 2, or 3;

$R^5$ is DMTr; and $R^6$ is —C(=O)CH$_2$CH$_2$C(=O)OH or

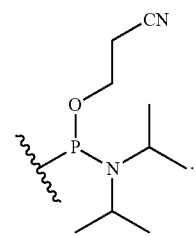 [SMILES: *P(OCCC#N)N(C(C)C)C(C)C]

25. The compound of claim 24, having the structure:
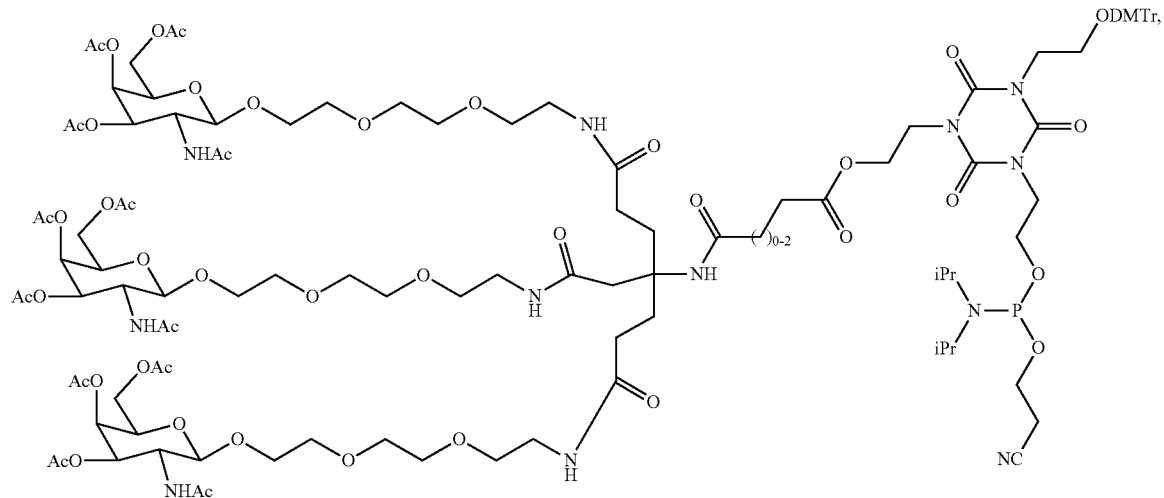
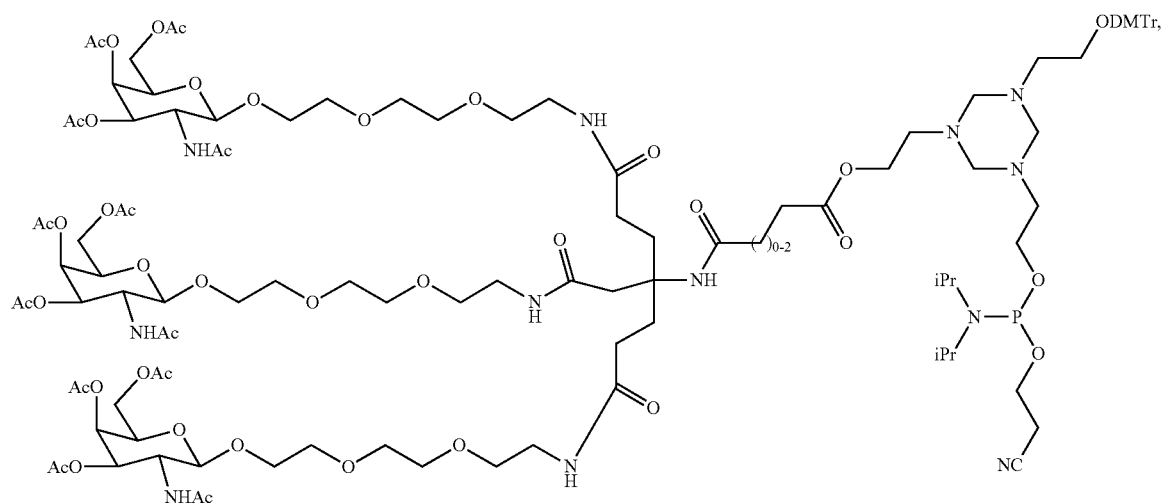
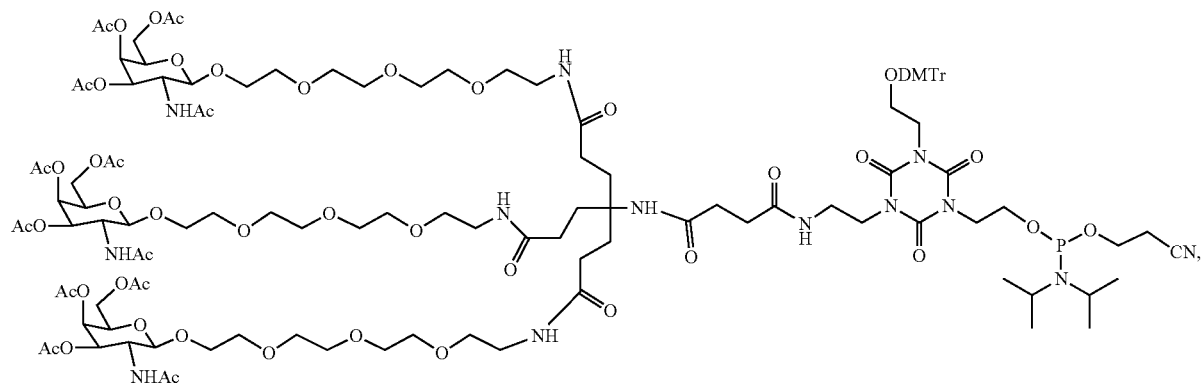

-continued
127
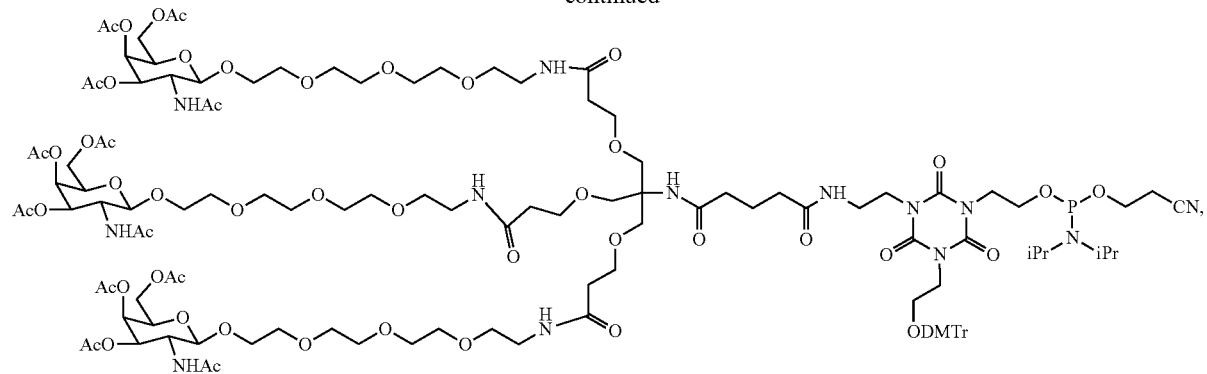
128
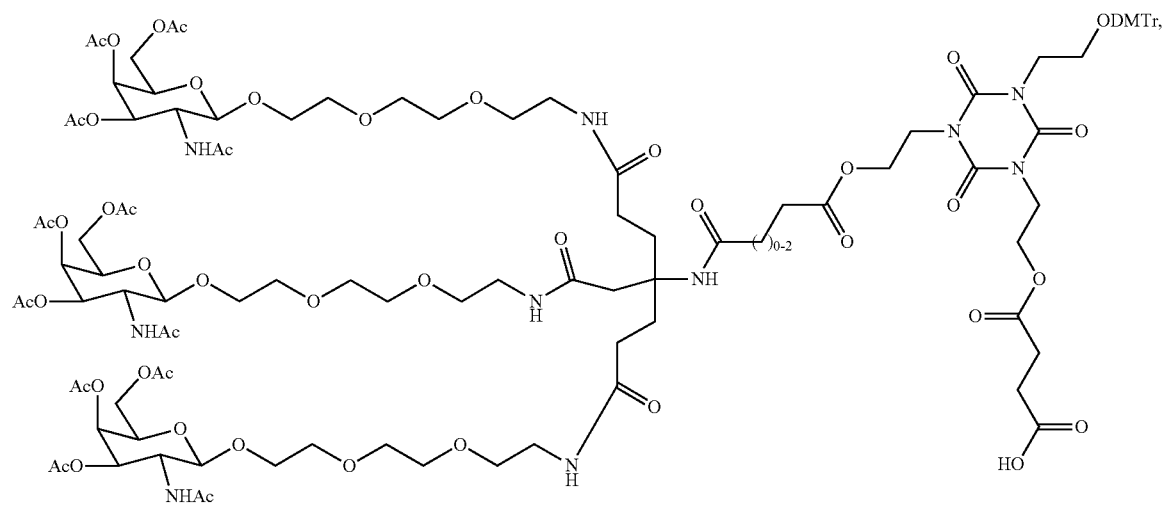
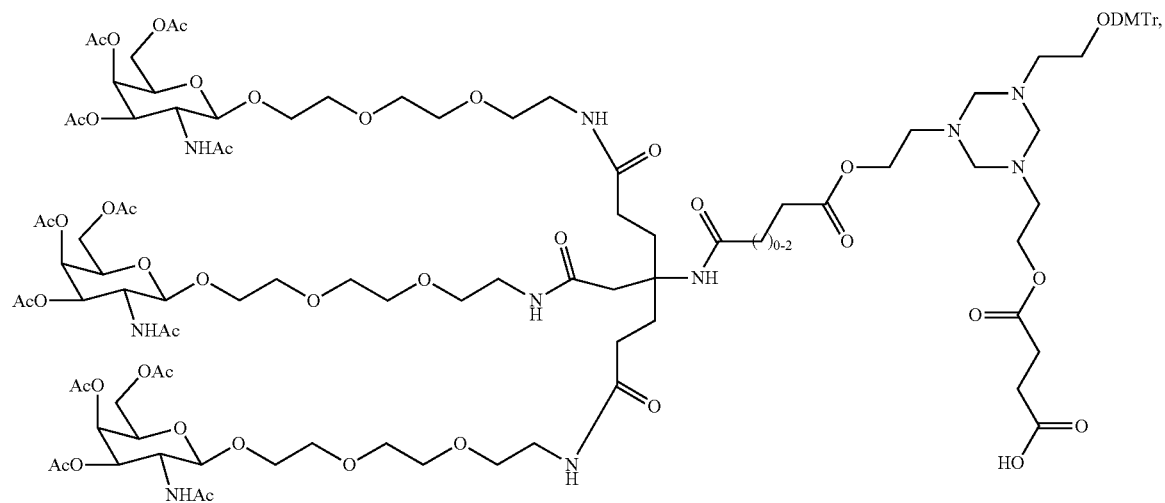

-continued

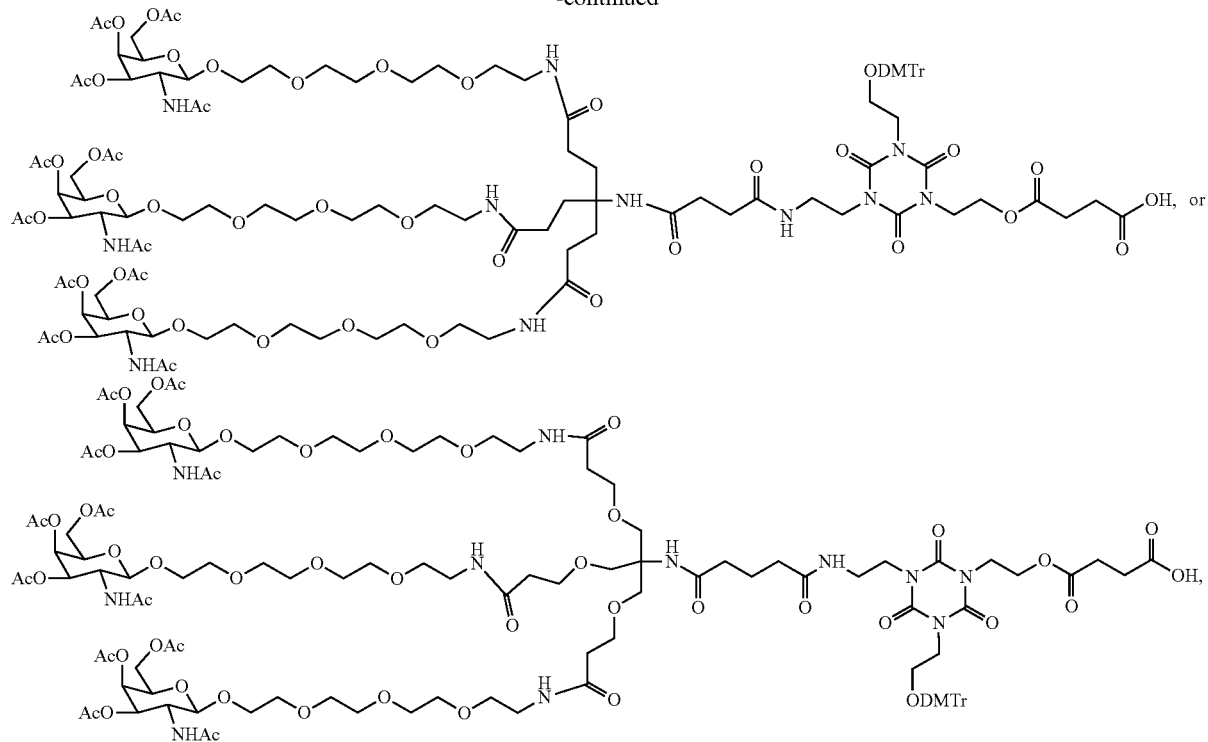

or a pharmaceutically acceptable salt thereof.

26. A method of preparing a synthetic oligonucleotide, comprising reacting a compound of claim 1, with an oligonucleotide.

27. An oligonucleotide prepared by the method of claim 26.

28. A solid support comprising the compound of claim 1 covalently attached thereto via $R^6$ of the compound of Formula (II).

29. The solid support of claim 28, wherein the compound is covalently attached to the solid support via a moiety:

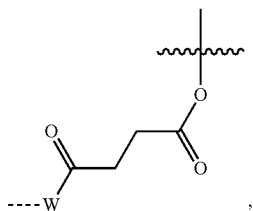

wherein W is O or NH; the dashed line refers to the connection with the solid support, optionally through an additional linker, and wherein the squiggly line refers to the point of the attachment of the oxygen atom that covalently attached to $R^6$ of the compound, to the remaining portion of the compound.

30. The compound of claim 24, wherein each of $L^{1a}$, Lib, $L^{1c}$, $L^{2a}$, $L^{2b}$, $L^{2c}$, $L^{3a}$, $L^{3b}$, and $L^{3c}$ is independently a bond, $C_{1-10}$ alkylene, 3 to 15 membered heteroalkylene where one or more carbon atoms are replaced with C(=O), O or N, or a PEG linker comprising one to five —OCH$_2$CH$_2$— repeating unit.

31. The compound of claim 30, wherein $L^5$ is a bond or C(=O)—(CH$_2$)$_{1-5}$.

* * * * *

UNITED STATES PATENT AND TRADEMARK OFFICE
CERTIFICATE OF CORRECTION

PATENT NO. : 11,993,626 B2
APPLICATION NO. : 18/065503
DATED : May 28, 2024
INVENTOR(S) : Wing C. Poon It is certified that error appears in the above-identified patent and that said Letters Patent is hereby corrected as shown below:

In the Specification

In Column 2, Line 37 (approx.), delete "hetetroarylene," and insert -- heteroarylene, --.

In Column 6, Line 13 (approx.), delete "hetetroarylene," and insert -- heteroarylene, --.

In Column 22, Line 53, delete "2-thienylallyl," and insert -- 2-thienylalkyl, --.

In Column 30, Line 12 (approx.), delete "hetetroarylene," and insert -- heteroarylene, --.

In Column 30, Line 15 (Approx.), delete "0, S" and insert -- O, S --.

In Column 41, Line 55, delete "hetetroarylene," and insert -- heteroarylene, --.

In Column 45, Line 55 (approx.), delete "$R^{2a}$, $R^{2b}$" and insert -- $R^{1b}$, $R^{2b}$ --.

In Column 46, Line 55 (approx.), delete "$R_{1c}$" and insert -- $R^{1c}$ --.

In Column 46, Line 58 (approx.), delete "$R^3$," and insert -- $R^{3c}$ --.

In Column 78, Line 3, delete "N,N-diisopropylchlorophosphoramindite" and insert -- N,N-diisopropylchlorophosphoramidite --.

In the Claims

In Column 112, Claim 1, Line 46, delete "hetetroarylene," and insert -- heteroarylene, --.

In Column 114, Claim 1, Line 1, delete "RN" and insert -- $R^N$ --.

Signed and Sealed this
Eighth Day of October, 2024

Katherine Kelly Vidal
*Director of the United States Patent and Trademark Office*

CERTIFICATE OF CORRECTION (continued)
U.S. Pat. No. 11,993,626 B2

In Column 116, Claim 16, Line 35 (approx.), delete "$L^{2a}L^{2b}$," and insert -- $L^{2a}$, $L^{2b}$, --.

In Column 130, Claim 30, Line 41 (approx.), delete "Lib," and insert -- $L^{1b}$, --.

In Column 130, Claim 30, Line 42 (approx.), delete "$L^{26}$," and insert -- $L^{2b}$, --.